United States Patent
Shin et al.

(10) Patent No.: US 12,256,630 B2
(45) Date of Patent: Mar. 18, 2025

(54) LIGHT-EMITTING DEVICE

(71) Applicant: Samsung Display Co., Ltd., Yongin-si (KR)

(72) Inventors: Hyosup Shin, Yongin-si (KR); Soobyung Ko, Yongin-si (KR); Tsuyoshi Naijo, Yongin-si (KR); Jiyoung Lee, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 738 days.

(21) Appl. No.: 17/522,855

(22) Filed: Nov. 9, 2021

(65) Prior Publication Data

US 2022/0310921 A1    Sep. 29, 2022

(30) Foreign Application Priority Data

Mar. 22, 2021 (KR) .................. 10-2021-0036754

(51) Int. Cl.
*H01L 51/50* (2006.01)
*H10K 85/30* (2023.01)
(Continued)

(52) U.S. Cl.
CPC ......... *H10K 85/322* (2023.02); *H10K 85/622* (2023.02); *H10K 85/626* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/11* (2023.02);
(Continued)

(58) Field of Classification Search
None
See application file for complete search history.

(56) References Cited

U.S. PATENT DOCUMENTS

| 6,515,298 B2 | 2/2003 | Forrest et al. |
| 10,290,816 B2 | 5/2019 | Forrest et al. |

(Continued)

FOREIGN PATENT DOCUMENTS

| EP | 3168893 | 5/2017 |
| KR | 20120004018 | 1/2012 |

(Continued)

OTHER PUBLICATIONS

Lee et. al., Simple heteroatom engineering for tuning the triplet energy of organometallic host materials for red, green and blue phosphorescent organic light-emitting diodes†; Chem. Commun., 2013, 49, 3875--3877 (Year: 2013).*

(Continued)

*Primary Examiner* — Gregory D Clark
(74) *Attorney, Agent, or Firm* — KILE PARK REED & HOUTTEMAN PLLC

(57) ABSTRACT

A light-emitting device includes: a first electrode; a second electrode facing the first electrode; and an interlayer between the first electrode and the second electrode and including an emission layer, wherein the emission layer includes: a first host, a second host, and a dopant, at least one of the first host and the second host is an organometallic compound, and the first host, the second host, and the dopant satisfy the following Equation (1):

|LUMO energy of $H2$−HOMO energy of $H1$|≥0.9× $T_1$ energy of $D$.

20 Claims, 2 Drawing Sheets

(51) Int. Cl.
*H10K 85/60* (2023.01)
*H10K 50/11* (2023.01)
*H10K 50/12* (2023.01)
*H10K 50/15* (2023.01)
*H10K 50/16* (2023.01)
*H10K 101/00* (2023.01)
*H10K 101/10* (2023.01)
*H10K 101/40* (2023.01)

(52) U.S. Cl.
CPC ............ *H10K 50/12* (2023.02); *H10K 50/15* (2023.02); *H10K 50/16* (2023.02); *H10K 2101/10* (2023.02); *H10K 2101/40* (2023.02); *H10K 2101/90* (2023.02)

(56) References Cited

U.S. PATENT DOCUMENTS

| | | | |
|---|---|---|---|
| 10,998,516 | B2 | 5/2021 | Ishisone et al. |
| 11,165,035 | B2 | 11/2021 | Liaptsis et al. |
| 11,723,270 | B2 | 8/2023 | Jang et al. |
| 11,895,915 | B2 | 2/2024 | Choi et al. |
| 2020/0194704 | A1 | 6/2020 | Seo et al. |
| 2020/0343469 | A1 | 10/2020 | Ohsawa et al. |
| 2020/0350503 | A1 | 11/2020 | Seo et al. |
| 2020/0395557 | A1 | 12/2020 | Ko et al. |
| 2021/0043840 | A1 | 2/2021 | Seo et al. |

FOREIGN PATENT DOCUMENTS

| | | |
|---|---|---|
| KR | 20180017077 | 2/2018 |
| KR | 10-2019-0010350 | 1/2019 |
| KR | 10-2019-0127581 | 11/2019 |
| KR | 10-2020-0045292 | 5/2020 |
| KR | 20200072124 | 6/2020 |
| KR | 20200130348 | 11/2020 |
| WO | 2017/191526 | 11/2017 |
| WO | 2019/087003 | 5/2019 |

OTHER PUBLICATIONS

Heimel, Paul, et al. "Unicolored Phosphor-Sensitized Fluorescence for Efficient and Stable Blue Oleds." Nature Communications, vol. 9, No. 1, 2018, https://doi.org/10.1038/s41467-018-07432-2.

Jeong Changyeong et al: "Understanding molecular fragmentation in blue phosphorescent organic light-emitting devices", Organic Electronics, vol. 64, Jan. 1, 2019, pp. 15-21, XP055944484, Amsterdam, NL.

Yun Bo-Sun et al: "Phosphysical properties of structural isomers of homoleptic Ir-complexes derived from xylenyl-substituted N-heterocyclic carbene ligands", Physical Chemistry Chemical Physics, vol. 21, No. 13, Mar. 27, 2019, pp. 7155-7164.

Karunathilaka Buddhika S. B. et al: "Suppression of external quantum efficiency rolloff in organic light emitting diodes by scavenging triplet excitons", Nature Communications, vol. 11, No. 1, Dec. 1, 2020.

\* cited by examiner

LIGHT-EMITTING DEVICE

CROSS-REFERENCE TO RELATED APPLICATION

This application claims priority from and the benefit of Korean Patent Application No. 10-2021-0036754, filed on Mar. 22, 2021, which is hereby incorporated by reference for all purposes as if fully set forth herein.

BACKGROUND

Field

Embodiments of the invention relate generally to display devices, and more particularly to light-emitting devices that may be used in display devices.

Discussion of the Background

Organic light-emitting devices (OLEDs) are self-emissive devices that have wide viewing angles, high contrast ratios, short response times, and excellent characteristics in terms of luminance, driving voltage, and response speed, compared to devices in the art.

Organic light-emitting devices may include a first electrode located on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

The above information disclosed in this Background section is only for understanding of the background of the inventive concepts, and, therefore, it may contain information that does not constitute prior art.

SUMMARY

Light-emitting devices constructed according to the principles and illustrative implementations of the invention have a novel structure providing for a low driving voltage and excellent lifespan. For example, Applicant discovered that when a light-emitting device made according to the principles and embodiments of the invention satisfies a one or more equations disclosed herein, energy of excitons composed of a first host and a second host may be efficiently transferred to a first host or a second host not participating in exciton formation and/or charges may be smoothly transferred to a host, and thus, an increase in driving voltage may be suppressed. Also, the energy transferred to the first host or the second host may be efficiently transferred to a dopant.

Additional features of the inventive concepts will be set forth in the description which follows, and in part will be apparent from the description, or may be learned by practice of the inventive concepts.

According to one aspect of the invention, a light-emitting device includes: a first electrode; a second electrode facing the first electrode; and an interlayer between the first electrode and the second electrode and including an emission layer, wherein the emission layer includes: a first host, a second host, and a dopant, at least one of the first host and the second host is an organometallic compound, and the first host, the second host, and the dopant satisfy the following Equation (1):

$$|\text{LUMO energy of } H2 - \text{HOMO energy of } H1| \geq 0.9 \times T_1 \text{ energy of } D.$$

The first electrode may include an anode, the second electrode may include a cathode, and the light-emitting device may further include a hole transport region between the first electrode and the emission layer and including an electron-blocking layer; and a hole injection layer, a hole transport layer, or any combination thereof.

The electron-blocking layer may include an electron-blocking material, and the first host and the electron-blocking material satisfy the following Equation (2):

$$|\text{HOMO energy of electron-blocking material} - \text{HOMO energy of } H1| \leq 0.2 \text{ eV}.$$

The electron-blocking layer may include an electron-blocking material, and an absolute value of LUMO energy of the electron-blocking material may be equal to or less than an absolute value of LUMO energy of the first host.

The first electrode may include an anode, the second electrode may include a cathode, and the light-emitting device may further include an electron transport region between the second electrode and the emission layer and including a hole-blocking layer; and an electron transport layer, an electron injection layer, or any combination thereof.

The hole-blocking layer may include a hole-blocking material, and the second host and the hole-blocking material satisfy the following Equation (3):

$$|\text{LUMO energy of hole-blocking material} - \text{LUMO energy of } H2| \leq 0.2 \text{ eV}.$$

The hole-blocking layer may include a hole-blocking material, and an absolute value of HOMO energy of the hole-blocking material may be greater than an absolute value of HOMO energy of the second host.

The first host may include a hole-transporting host.

The second host may include an electron-transporting host.

The first host may have an absolute value of LUMO energy less than an absolute value of LUMO energy of the second host.

The second host may have an absolute value of HOMO energy greater than an absolute value of HOMO energy of the first host.

The first host and the second host may have a weight ratio of about 1:9 to about 9:1.

The dopant may be a fluorescent dopant.

The light-emitting device may include a plurality of the first hosts and a plurality of the second hosts, at least one of the first hosts and at least one of the second hosts form excitons, and others of the first hosts or others of the second hosts that may not form excitons capable of transferring energy of the excitons to the dopant.

The organometallic compound may be a compound of Formula 401 or Formula 402, as described herein.

Each of the first host and the second host may not be the organometallic compound, wherein the first host may be a compound of Formula 1, and the second host may be a compound of Formula 2, as described herein.

The dopant may be one of the following compounds DF8, DF9, and FD1 to FD8, as described herein.

An electronic apparatus may include the light-emitting device as described above.

The electronic apparatus may further include a thin-film transistor, wherein the thin-film transistor may include a source electrode and a drain electrode, and the first electrode of the light-emitting device may be electrically connected to at least one of the source electrode and the drain electrode of the thin-film transistor.

The electronic apparatus may further include a color filter, a color conversion layer, a touch screen layer, a polarizing layer, or any combination thereof.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
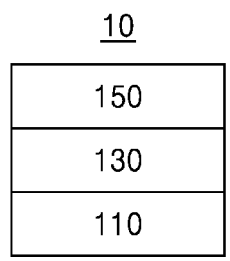
FIG. 1 is a schematic cross-sectional view of an embodiment of a light-emitting device constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements, and repetitive explanations are omitted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

In the related art, it is known to use two hosts and two dopants with one of the dopants functioning as a sensitizer. In a radiative path of such related art, two hosts form excitons (the first step), energy of the excitons is transferred to a sensitizer which is one of two dopants (the second step), and the energy is transferred from the sensitizer to the remaining other dopant of the two dopants which emits light (the third step).

To transfer charges to an emission layer, it is required to cross a certain energy barrier, and thus, there may be an increase in driving voltage. Regarding this issue, for example, it is required to align highest occupied molecular orbital (HOMO) energy of a hole transport region material with HOMO energy of a hole-transporting host in the emission layer. To this end, a HOMO of the hole-transporting host in the emission layer needs to be shallow, in which case exciton energy of the host may be lowered, so that energy transfer to the sensitizer may be difficult.

Charge trapping by the dopant that emits light may adversely affect a device lifespan. To reduce the charge trapping, for example, a hole-transporting host having shallow HOMO energy needs to be used in the emission layer. However, Applicant discovered that when a shallow hole-transporting host is used for the above-mentioned reasons, exciton energy of the host may be lowered, so that energy transfer to the sensitizer may be difficult.

According to one aspect of the invention, an embodiment of a light-emitting device may include: a first electrode; a second electrode facing the first electrode; and an interlayer located between the first electrode and the second electrode and including an emission layer, wherein the emission layer may include a first host (H1), a second host (H2), and a dopant (D), at least one of the first host and the second host may be an organometallic compound, and the first host, the second host, and the dopant may satisfy the following Equation (1):

$$|\text{LUMO energy of } H2 - \text{HOMO energy of } H1| \geq 0.9 \times T_1 \text{ energy of } D \quad (1).$$

Because the light-emitting device according to an embodiment of the invention is satisfies Equation (1), energy of excitons composed of a first host and a second host may be efficiently transferred to a first host or a second host not participating in exciton formation. Also, the energy transferred to the first host or the second host may be efficiently transferred to a dopant.

In an embodiment, the organometallic compound may be a phosphorescent emitter. In an embodiment, the first electrode may be an anode, the second electrode may be a cathode, and a hole transport region located between the first electrode and the emission layer and including an electron-blocking layer; and a hole injection layer, a hole transport layer, or any combination thereof may be further included. In an embodiment, the electron-blocking layer may include an electron-blocking material, and the first host and the electron-blocking material may satisfy the following Equation (2):

$$|\text{HOMO energy of electron-blocking material} - \text{HOMO energy of } H1| \leq 0.2 \text{ eV} \quad (2).$$

Because the light-emitting device according to an embodiment satisfies Equation (2), charges may be smoothly transferred to a host, and thus, an increase in driving voltage may be suppressed. In an embodiment, the charges may be holes. In an embodiment, the electron-blocking layer may include an electron-blocking material, and an absolute value of lowest unoccupied molecular orbital (LUMO) energy of the electron-blocking material may be equal to or less than an absolute value of LUMO energy of the first host. In an embodiment, the first electrode may be an anode, the second electrode may be a cathode, and an electron transport region located between the second electrode and the emission layer and including a hole-blocking layer; and an electron transport layer, an electron injection layer, or any combination thereof may be further included.

In an embodiment, the hole-blocking layer may include a hole-blocking material, and the second host and the hole-blocking material may satisfy the following Equation (3):

$$|\text{LUMO energy of hole-blocking material} - \text{LUMO energy of } H2| \leq 0.2 \text{ eV} \quad (3).$$

Because the light-emitting device according to an embodiment satisfies Equation (3), charges may be smoothly transferred to a host, and thus, an increase in driving voltage may be suppressed. In an embodiment, the charges may be electrons. In an embodiment, the hole-blocking layer may include a hole-blocking material, and an absolute value of HOMO energy of the hole-blocking material may be greater than an absolute value of HOMO energy of the second host.

In an embodiment, the first host may be a hole-transporting host. In an embodiment, the second host may be an electron-transporting host. In an embodiment, an absolute value of LUMO energy of the first host may be less than an absolute value of LUMO energy of the second host. In an embodiment, an absolute value of HOMO energy of the second host may be greater than an absolute value of HOMO energy of the first host.

In an embodiment, a weight ratio of the first host to the second host may be from about 1:9 to about 9:1. In an embodiment, the weight ratio of the first host to the second host may be from about 3:7 to about 7:3. When the weight ratio of the first host to the second host is within the above range, transport of holes and transport of electrons may be in a desirable balance. In an embodiment, the dopant may be a fluorescent dopant. In an embodiment, the dopant may be a thermally activated delayed fluorescence dopant.

In an embodiment, the light-emitting device may include a plurality of the first hosts (H1s) and a plurality of the second hosts (H2s), at least one of the first hosts and at least one of the second hosts may form excitons, and others of the first hosts or others of the second hosts that do not form excitons may transfer energy of the excitons to the dopant. In an embodiment, the first host may be a hole-transporting host. In an embodiment, the second host may be an electron-transporting host.

In an embodiment, when the light-emitting device according to an embodiment includes an electron-blocking layer, wherein the electron-blocking layer includes an electron-blocking material, first hosts, second hosts, and a dopant satisfy Equation (1), and the first hosts and the electron-blocking material satisfy Equation (2), holes may be smoothly transferred to the host (the first host and the second host), thereby suppressing an increase in driving voltage, at least one of the first hosts and at least one of the second hosts may form excitons, and the others of the first hosts that do not form excitons may efficiently transfer energy of the excitons to the dopant.

In this case, the first host may be an organometallic compound and may act as a phosphorescent emitter and a sensitizer at the same time, the second host may be a pure organic compound (not including a metal), and the dopant may be a fluorescent dopant.

In an embodiment, when the light-emitting device according to an embodiment includes a hole-blocking layer, wherein the hole-blocking layer includes a hole-blocking material, first hosts, second hosts, and a dopant satisfy Equation (1), and the second hosts and the hole-blocking material satisfy Equation (3), electrons may be smoothly transferred to the host (the first host and the second host), thereby suppressing an increase in driving voltage, at least one of the first hosts and at least one of the second hosts may form excitons, and the others of the second hosts that do not form excitons may efficiently transfer energy of the excitons to the dopant.

In this case, the second host may be an organometallic compound and may act as a phosphorescent emitter and a sensitizer at the same time, the first host may be a pure organic compound (not including a metal), and the dopant may be a fluorescent dopant. In an embodiment, when the light-emitting device includes an electron-blocking layer and a hole-blocking layer, wherein the electron-blocking layer includes an electron-blocking material, and the hole-blocking layer includes a hole-blocking material, a first host, a second host, and a dopant satisfy Equation (1), the first host and the electron-blocking material satisfy Equation (2), and the second host and the hole-blocking material satisfy Equation (3), holes and electrons may be smoothly transferred to the host (the first host and the second host), thereby suppressing an increase in driving voltage, at least one of the first hosts and at least one of the second hosts may form excitons, and the others of the first hosts and/or the others of the second hosts that do not form excitons may efficiently transfer energy of the excitons to the dopant.

In this case, each of the first host and the second host may be an organometallic compound and may act as a phosphorescent emitter and a sensitizer at the same time, and the dopant may be a fluorescent dopant. The first host and the second host as organometallic compounds may be different organometallic compounds from each other.

Although an organometallic compound which is a phosphorescent emitter is generally a hole-transporting compound, a ligand or a substituent of a ligand of the organometallic compound may adjusted to lower a HOMO level, so that the organometallic compound which is a phosphorescent emitter may become an electron-transporting compound.

According to another aspect of the invention an electronic apparatus may include the light-emitting device. As an example, an electronic apparatus includes a thin-film transistor and the light-emitting device, wherein the thin-film transistor may include a source electrode, a drain electrode, an activation layer, and a gate electrode, and the first electrode of the light-emitting device may be electrically connected to one of the source electrode and the drain electrode of the thin-film transistor.

Description of FIG. 1

FIG. 1 is a schematic cross-sectional view of an embodiment of a light-emitting device constructed according to the principles of the invention. Particularly, FIG. 1 is a schematic cross-sectional view of a light-emitting device 10 according to an embodiment of the present disclosure. The light-emitting device 10 includes a first electrode 110, an interlayer 130, and a second electrode 150.

Hereinafter, the structure of the light-emitting device 10 constructed according to the principles and an illustrative embodiment and an illustrative method of manufacturing the light-emitting device 10 will be described in connection with FIG. 1.

First Electrode 110

In FIG. 1, a substrate may be additionally located under the first electrode 110 or above the second electrode 150. As the substrate, a glass substrate or a plastic substrate may be used. In one or more embodiments, the substrate may be a flexible substrate, and may include plastics with excellent heat resistance and durability, such as a polyimide, a polyethylene terephthalate (PET), a polycarbonate, a polyethylene naphthalate, a polyarylate (PAR), a polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include an indium tin oxide (ITO), an indium zinc oxide (IZO), a tin oxide ($SnO_2$), a zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode.

The first electrode 110 may have a single-layered structure consisting of a single layer or a multi-layered structure including a plurality of layers. In an embodiment, the first electrode 110 may have a three-layered structure of an ITO/Ag/ITO.

Interlayer 130

The interlayer 130 may be located on the first electrode 110. The interlayer 130 may include an emission layer. The interlayer 130 may further include a hole transport region located between the first electrode 110 and the emission layer and an electron transport region located between the emission layer and the second electrode 150. The interlayer 130 may further include, in addition to various organic materials, metal-containing compounds such as organometallic compounds, inorganic materials such as quantum dots, and the like.

In one or more embodiments, the interlayer 130 may include, i) two or more light-emitting units sequentially stacked between the first electrode 110 and the second electrode 150 and ii) a charge generation layer located between the two or more emitting units. When the interlayer 130 includes the emitting unit and the charge generation layer as described above, the light-emitting device 10 may be a tandem light-emitting device 10.

Hole Transport Region in Interlayer 130

The hole transport region may have: i) a single-layered structure consisting of a single layer consisting of a single material, ii) a single-layered structure consisting of a single layer consisting of a plurality of different materials, or iii) a multi-layered structure including a plurality of layers including different materials. The hole transport region may include an electron-blocking layer; and a hole injection layer, a hole transport layer, an emission auxiliary layer, or any combination thereof.

In an embodiment, the hole transport region may have a multi-layered structure including a hole injection layer/hole transport layer/electron-blocking layer structure, a hole injection layer/hole transport layer/emission auxiliary layer/electron-blocking layer structure, a hole injection layer/emission auxiliary layer/electron-blocking layer structure, or a hole transport layer/emission auxiliary layer/electron-blocking layer structure, wherein, in each structure, layers are stacked sequentially from the first electrode 110, but embodiments are not limited thereto.

The hole transport region may include a compound represented by Formula 201, a compound represented by Formula 202, or any combination thereof:

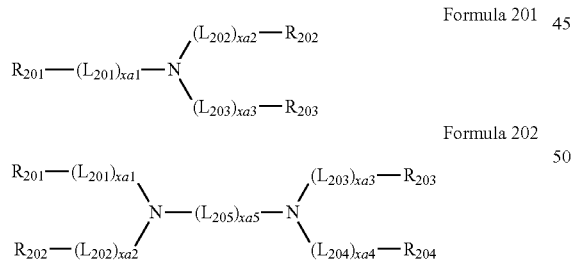

Formula 201

Formula 202 wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of groups represented by Formulae CY201 to CY217:

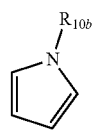

CY201

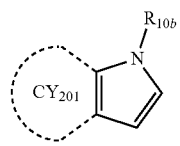

CY202

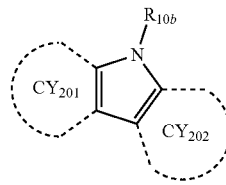

CY203

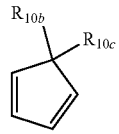

CY204

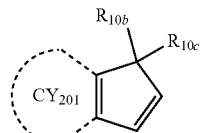

CY205

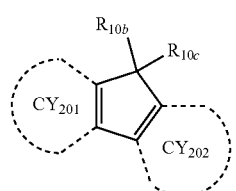

CY206

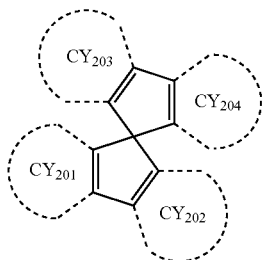

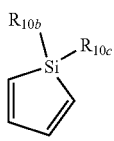

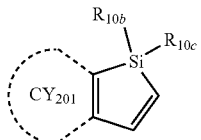

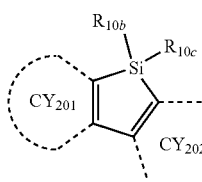

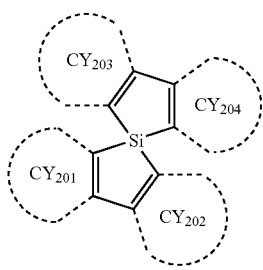

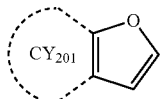

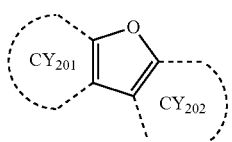

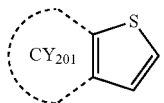

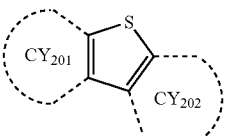

wherein, in Formulae CY201 to CY217, $R_{10b}$ and $R_{10c}$ are each the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring CY201 to ring CY204 in Formulae CY201 to CY217 may each independently be a benzene group, a naphthalene group, a phenanthrene group, or an anthracene group. In one or more embodiments, each of Formulae 201 and 202 may include at least one of groups represented by Formulae CY201 to CY203. In one or more embodiments, Formula 201 may include at least one of groups represented by Formulae CY201 to CY203 and at least one of groups represented by Formulae CY204 to CY217.

In one or more embodiments, in Formula 201, xa1 may be 1, $R_{201}$ may be a group represented by one of Formulae CY201 to CY203, xa2 may be 0, and $R_{202}$ may be a group represented by one of Formulae CY204 to CY207. In one or more embodiments, each of Formulae 201 and 202 may not include a group represented by one of Formulae CY201 to CY203. In one or more embodiments, each of Formulae 201 and 202 may not include a group represented by one of Formulae CY201 to CY203, and may include at least one of groups represented by Formulae CY204 to CY217. In one or more embodiments, each of Formulae 201 and 202 may not include a group represented by one of Formulae CY201 to CY217.

In an embodiment, the hole transport region may include one of Compounds HT1 to HT46, 4,4′,4″-tris[phenyl(m-tolyl)amino]triphenylamine (m-MTDATA), 1-N,1-N-bis[4-(diphenylamino)phenyl]-4-N,4-N-diphenylbenzene-1,4-diamine (TDATA), 4,4′,4″-tris[2-naphthyl(phenyl)amino] triphenylamine (2-TNATA), 4,4′-bis[N-(1-naphthyl)-N-phenylamino]biphenyl (NPB or NPD), N4,N4′-di (naphthalen-2-yl)-N4,N4′-diphenyl-[1,1′-biphenyl]-4,4′-diamine (β-NPB,), N,N′-bis(3-methylphenyl)-N,N′-diphenylbenzidine (TPD,), N,N′-bis(3-methylphenyl)-N,N′-diphenyl-9,9-spirobifluorene-2,7-diamine (Spiro-TPD), N2,N7-di-1-naphthalenyl-N2,N7-diphenyl-9,9′-spirobi[9H-fluorene]-2,7-diamine (Spiro-NPB), N,N′-di(1-naphthyl)-N,N-diphenyl-2,2′-dimethyl-(1,1′-biphenyl)-4,4′-diamine (methylated NPB), 4,4′-cyclohexylidenebis[N,N-bis(4-methylphenyl)benzenamine] (TAPC), N,N,N′,N′-tetrakis(3-methylphenyl)-3,3′-dimethylbenzidine (HMTPD), 1,1-bis [(di-4-tolylamino)phenyl]cyclohexane (TCTA), polyaniline/dodecylbenzenesulfonic acid (PANT/DB SA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1
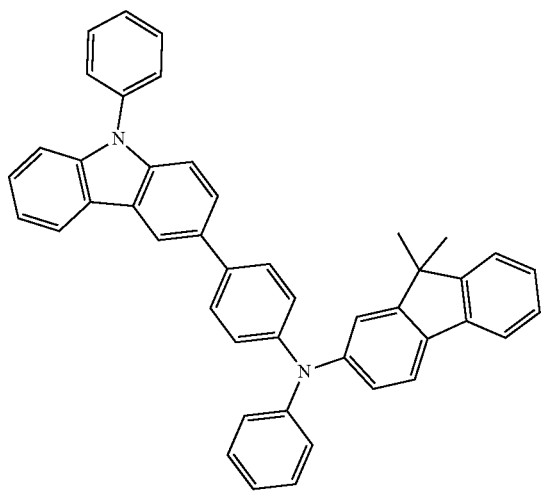
HT3
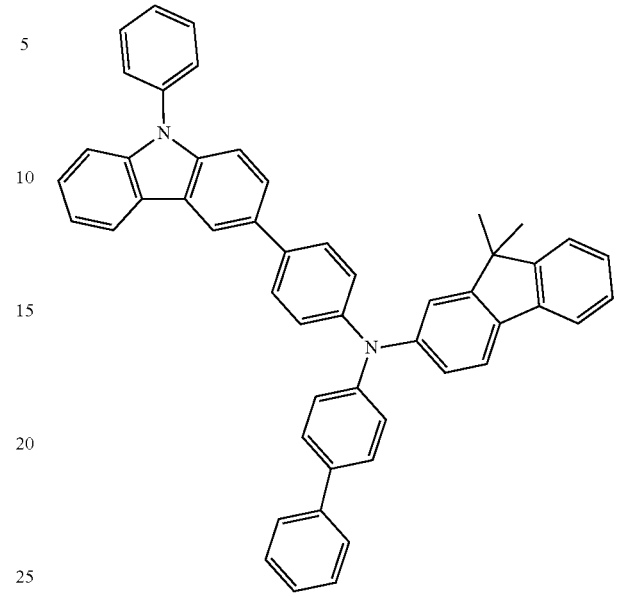
HT2
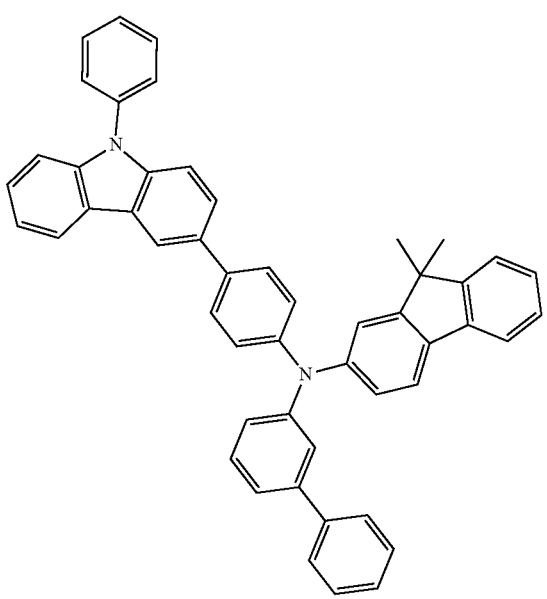
HT4
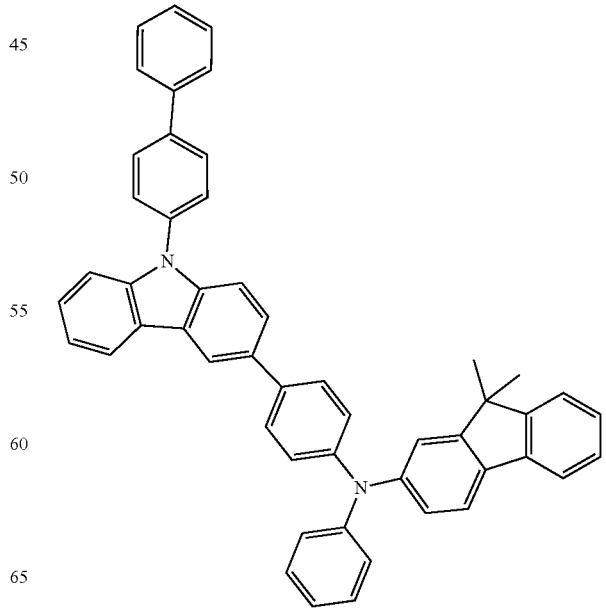

HT5
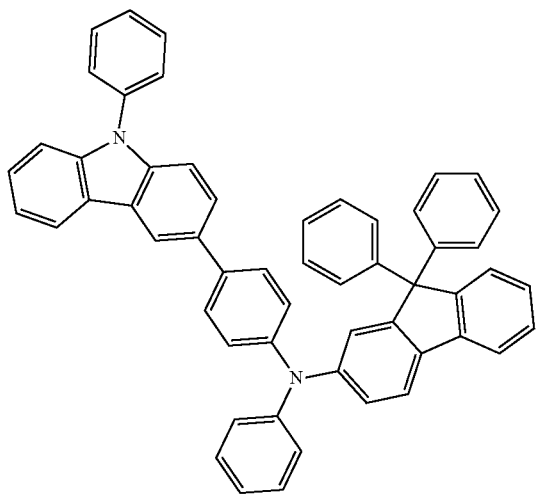
HT7
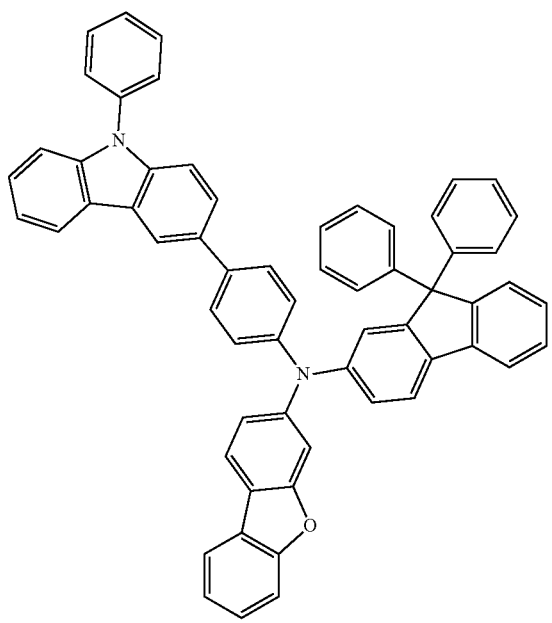
HT6
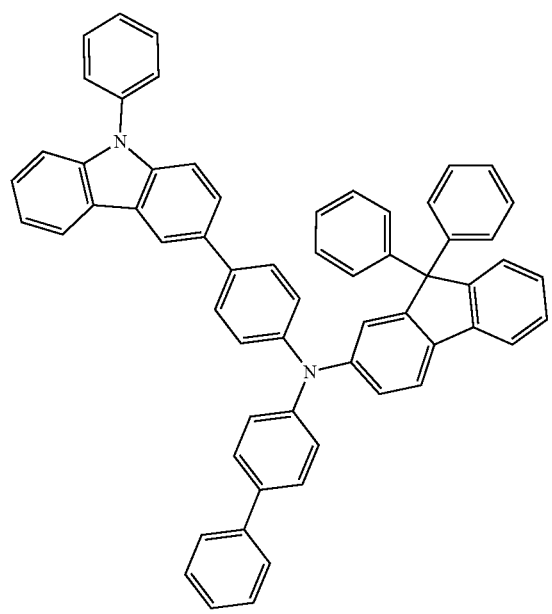
HT8
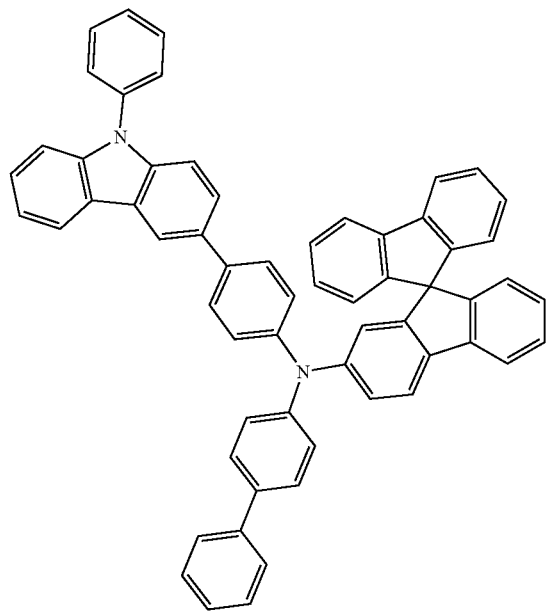

HT9
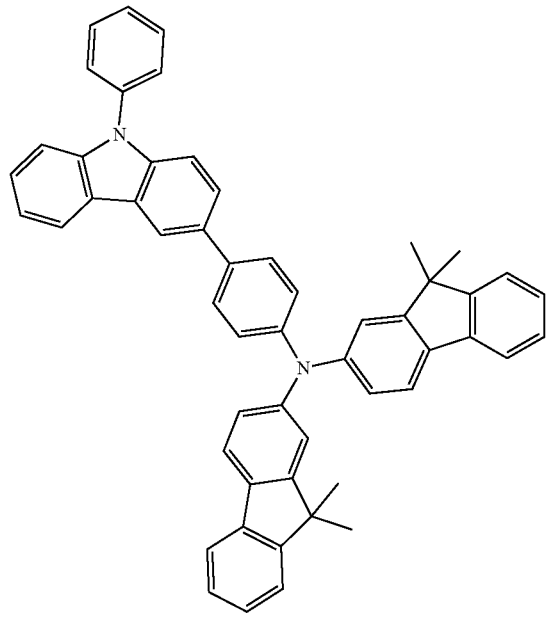
HT11
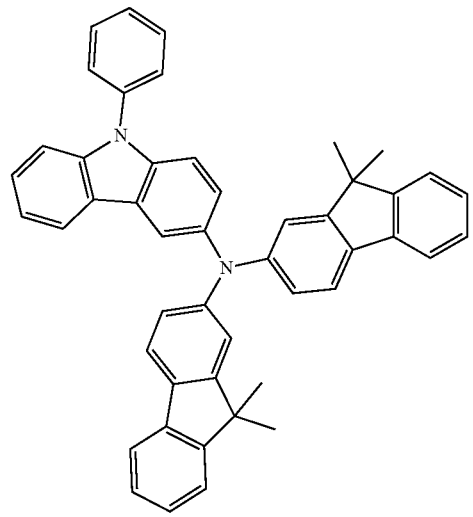
HT12
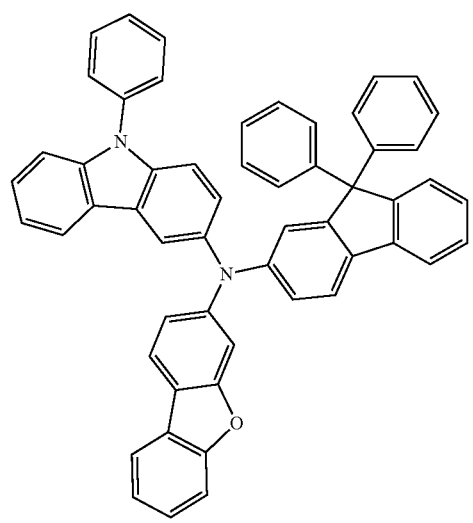
HT10
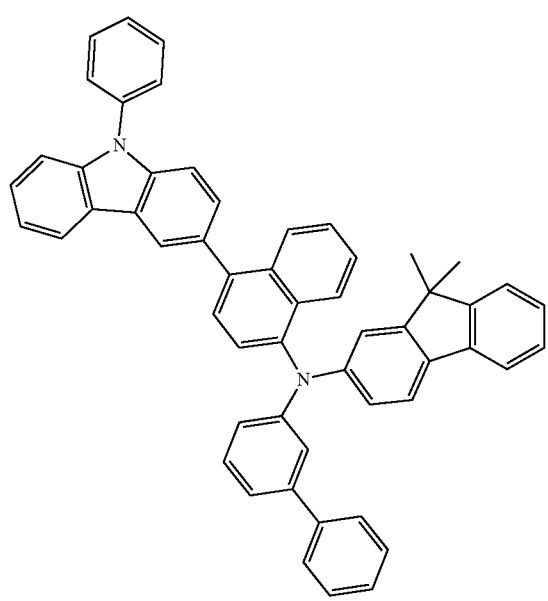
HT13
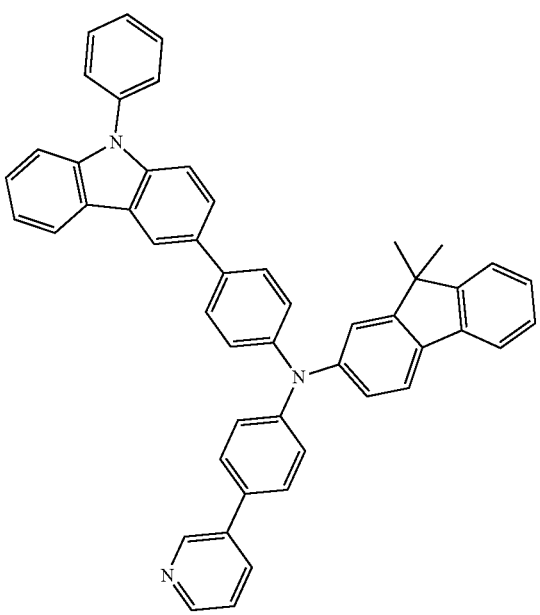

HT14
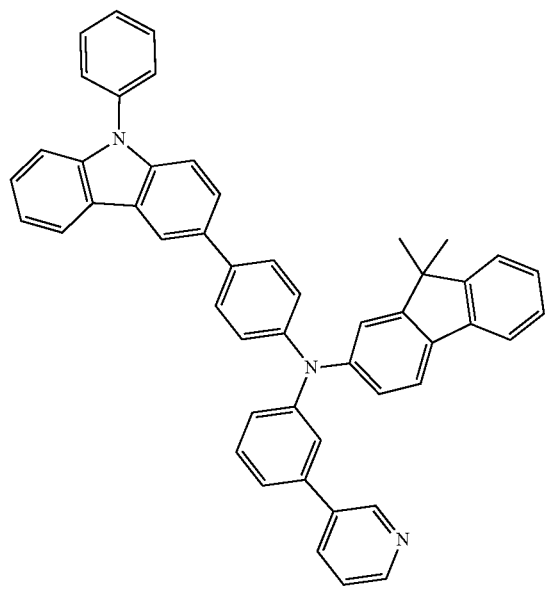
HT17
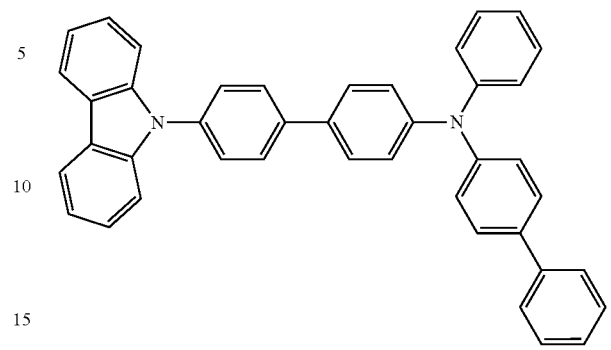
HT15
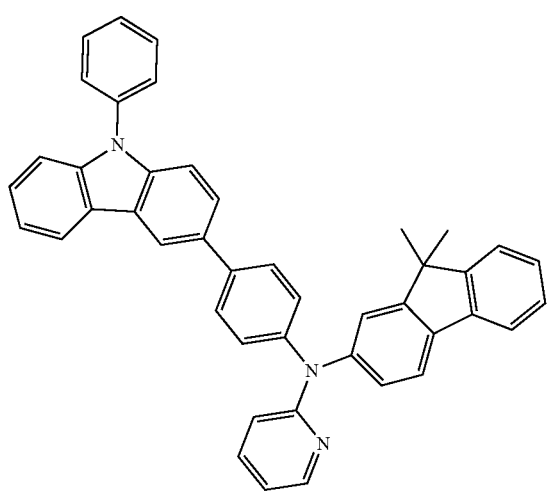
HT18
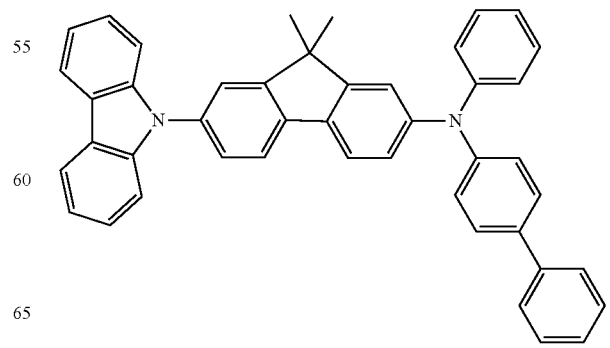
HT16
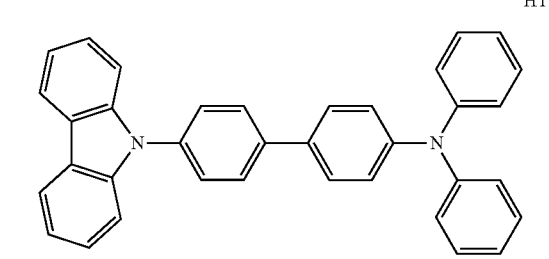
HT19

HT20
HT21
HT22
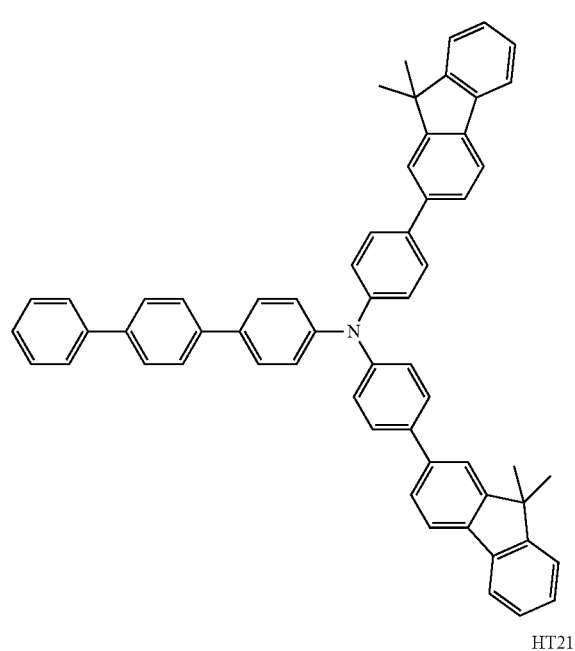
HT23
HT24
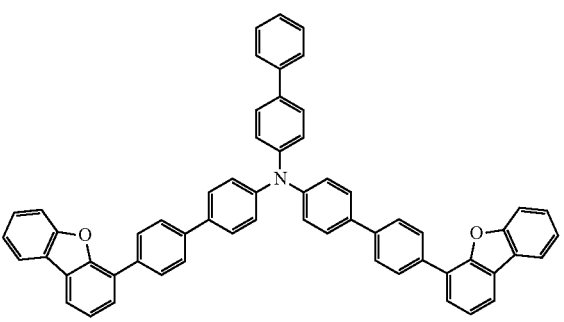
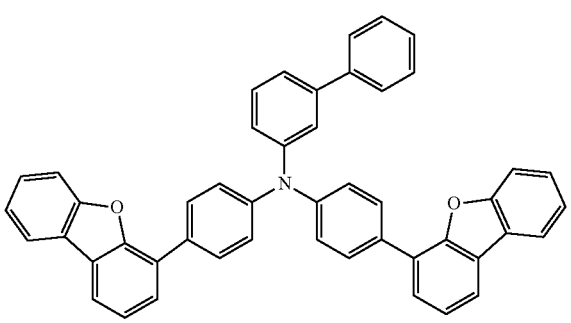
HT25

HT26
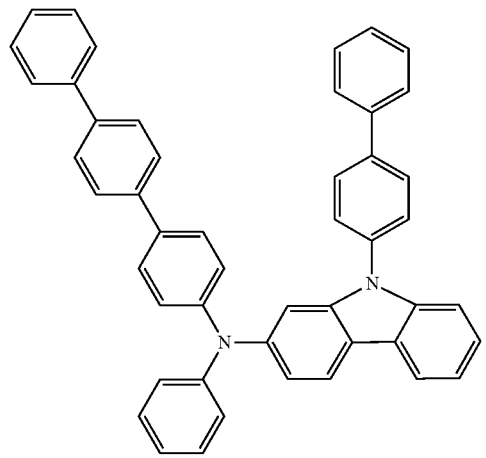
HT27
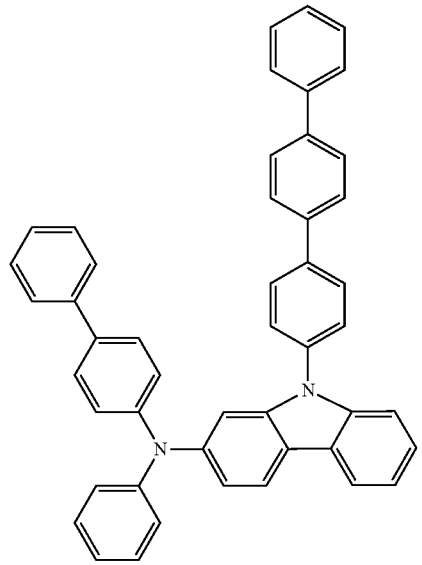
HT28
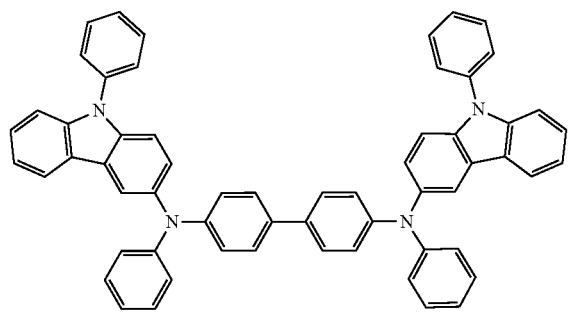
HT29
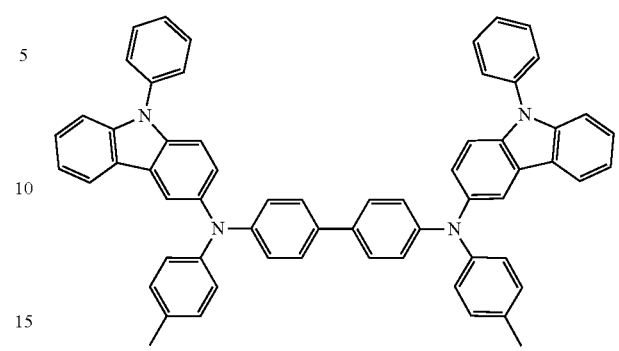
HT30
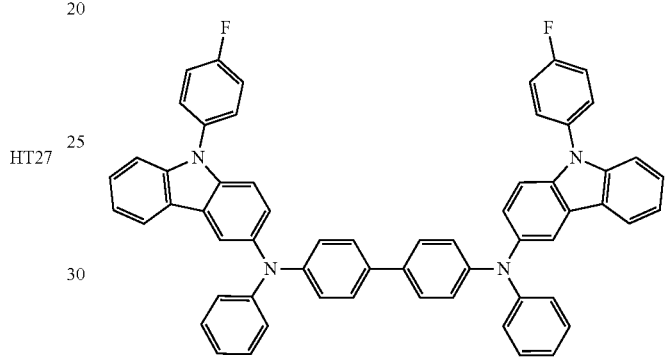
HT31
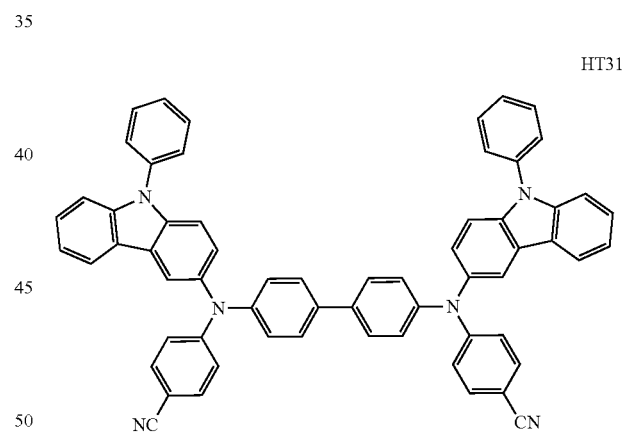
HT32
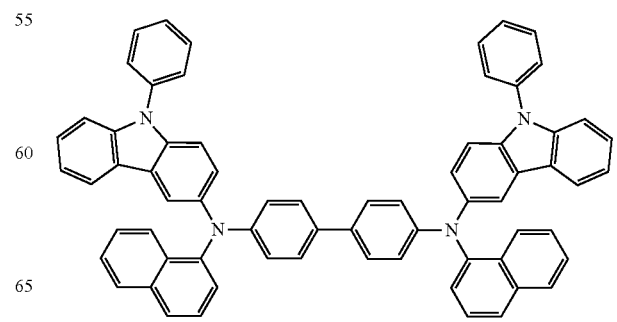

HT33
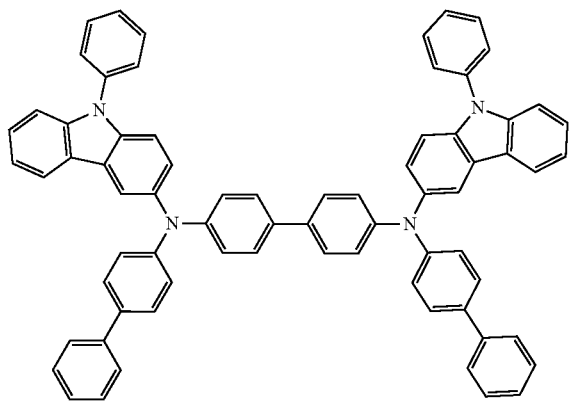
HT36
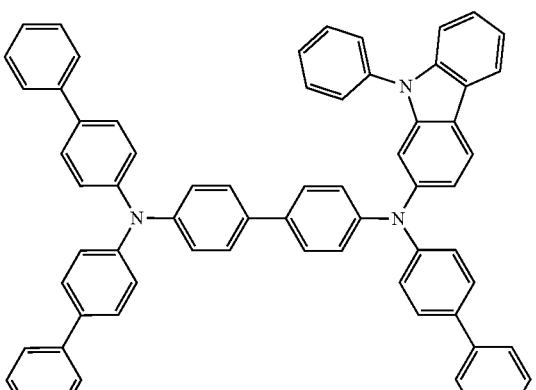
HT34
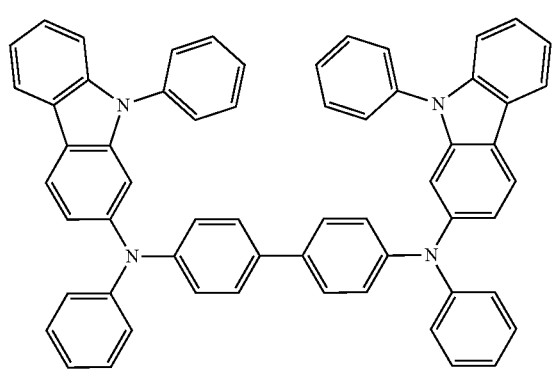
HT37
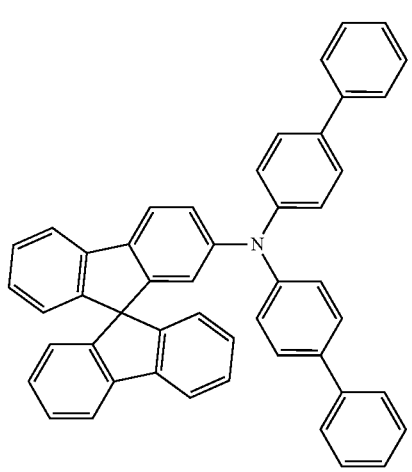
HT35
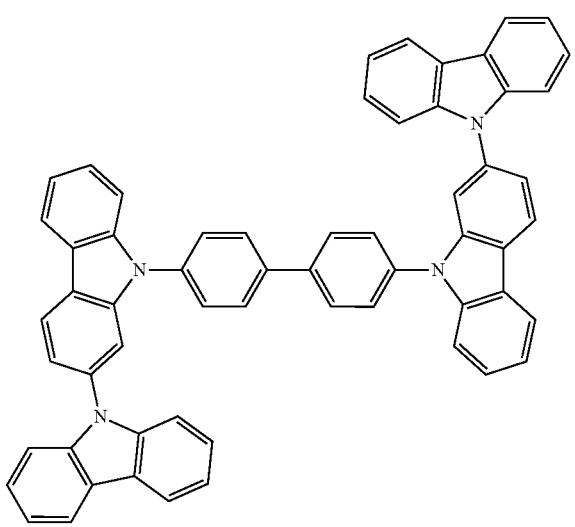
HT38
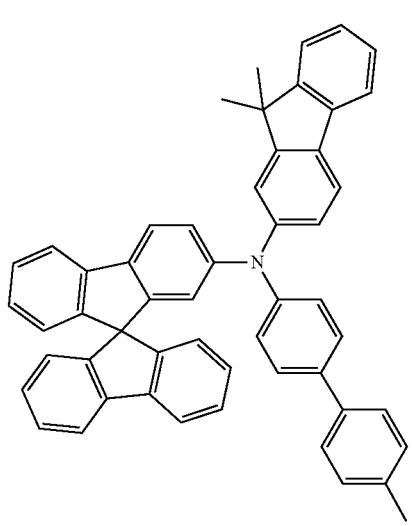

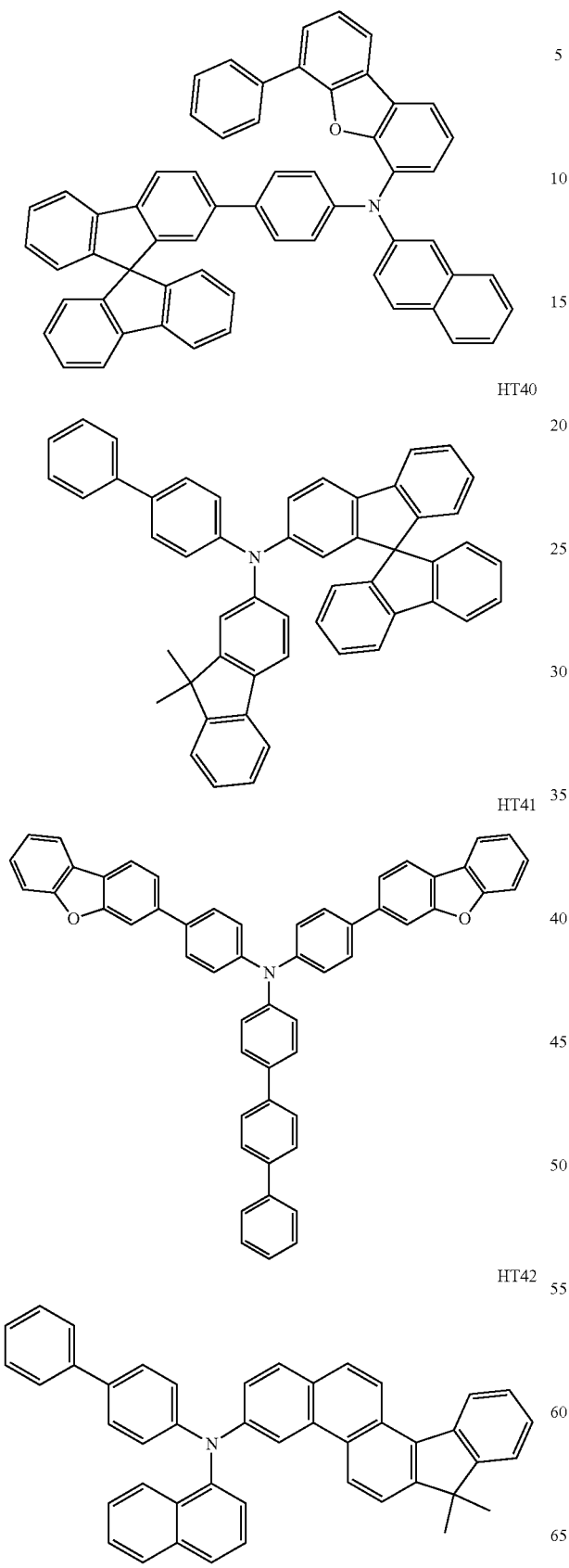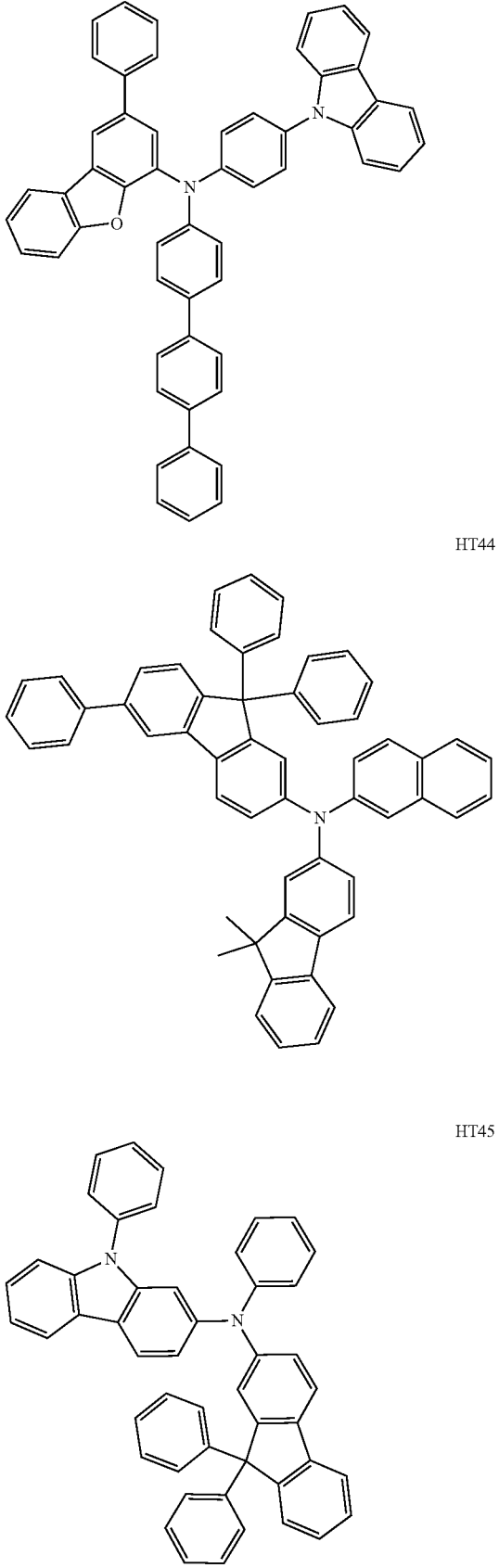

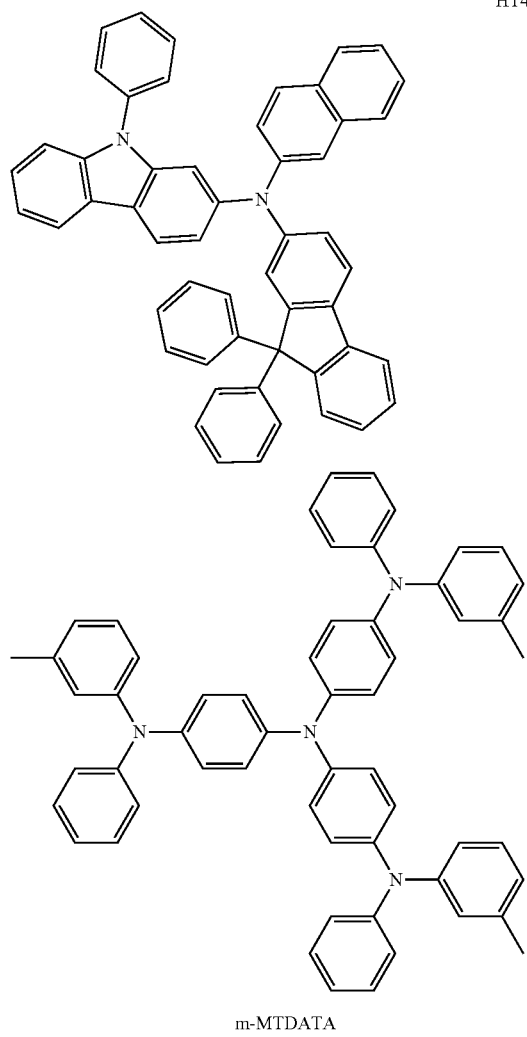
m-MTDATA
TDATA
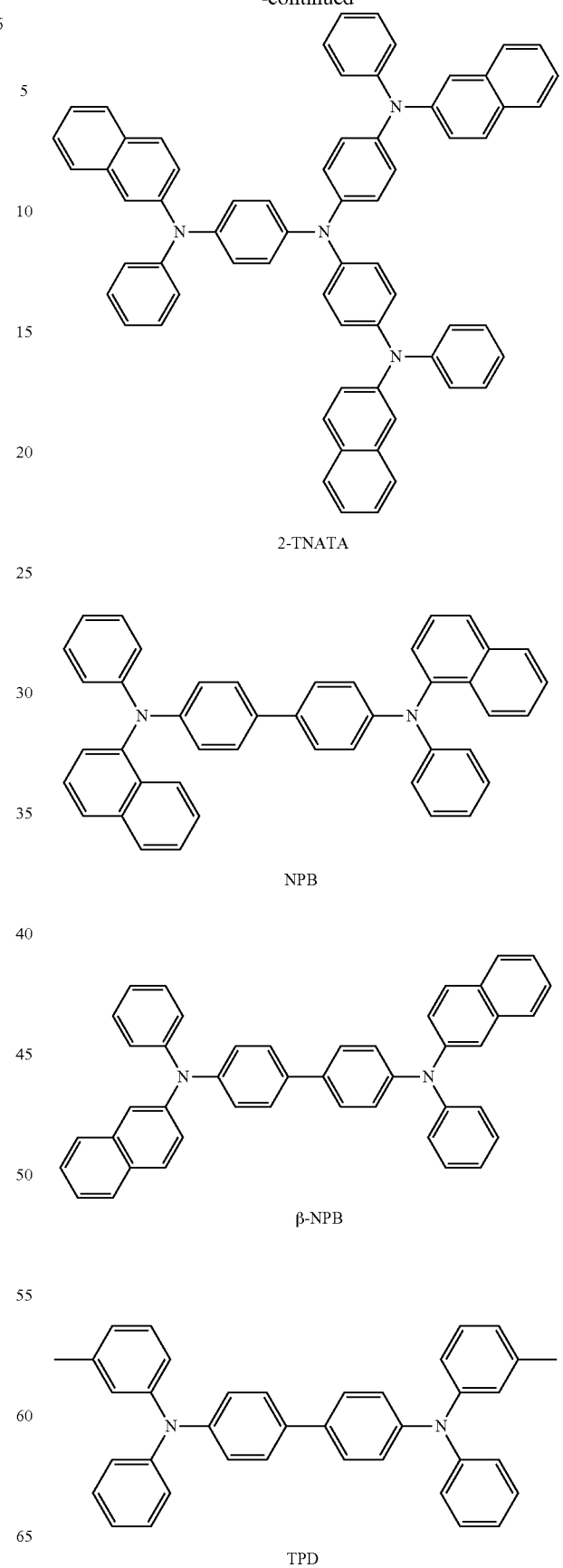
HT46
2-TNATA
NPB
β-NPB
TPD

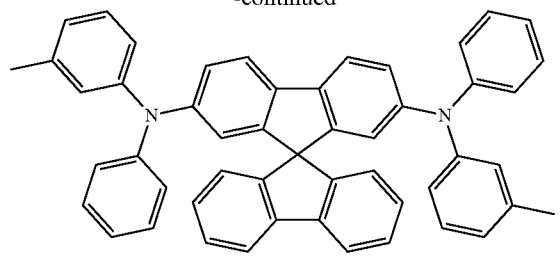

Spiro-TPD

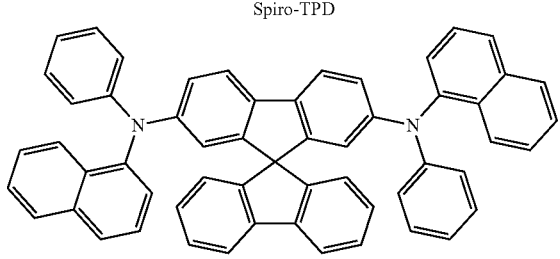

Spiro-NPB

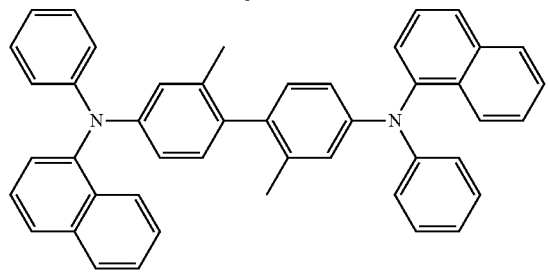

methylated-NPB

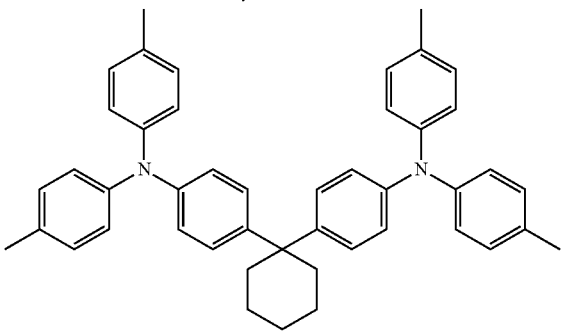

TAPC

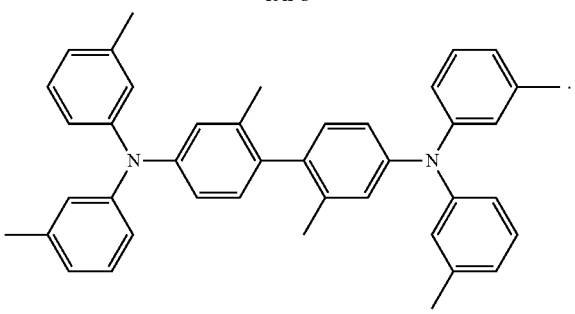

HMTPD

The thickness of the hole transport region may be in a range of about 50 Å to about 10,000 Å, for example, about 100 Å to about 4,000 Å. When the hole transport region includes an electron-blocking layer, a hole transport layer, or any combination thereof, the thickness of the electron-blocking layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the electron-blocking layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron-blocking layer may block the leakage of electrons from an emission layer to a hole transport region. Materials that may be included in the hole transport region may be included in the emission auxiliary layer and the electron-blocking layer.

p-Dopant

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material). The charge-generation material may be, for example, a p-dopant. In an embodiment, a LUMO energy level of the p-dopant may be about −3.5 eV or less.

In an embodiment, the p-dopant may include a quinone derivative, a cyano group-containing compound, a compound containing element EL1 and element EL2, or any combination thereof. Examples of the quinone derivative may include tetracyanoquinodimethane (TCNQ) and 2,3,5,6-tetrafluoro-7,7,8,8-tetracyanoquinodimethane (F4-TCNQ). Examples of the cyano group-containing compound may include 1,4,5,8,9,12-hexaazatriphenylene-hexacarbonitrile (HAT-CN) and a compound represented by Formula 221.

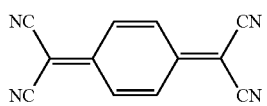

TCNQ

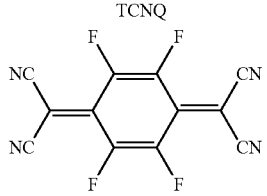

F4-TCNQ

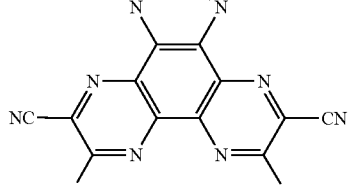

HAT-CN

-continued

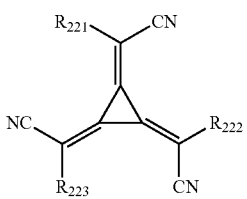

Formula 221

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or any combination thereof, and element EL2 may be a non-metal, a metalloid, or any combination thereof.

Examples of the metal may include: an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te). Examples of the non-metal may include oxygen (O) and a halogen (for example, F, Cl, Br, I, etc.).

In an embodiment, examples of the compound containing element EL1 and element EL2 may include a metal oxide, a metal halide (for example, a metal fluoride, a metal chloride, a metal bromide, or a metal iodide), a metalloid halide (for example, a metalloid fluoride, a metalloid chloride, a metalloid bromide, or a metalloid iodide), a metal telluride, or any combination thereof.

Examples of the metal oxide may include a tungsten oxide (for example, WO, $W_2O_3$, $WO_2$, $WO_3$, $W_2O_5$, etc.), a vanadium oxide (for example, VO, $V_2O_3$, $VO_2$, $V_2O_5$, etc.), a molybdenum oxide ($MoO$, $Mo_2O_3$, $MoO_2$, $MoO_3$, $Mo_2O_5$, etc.), and a rhenium oxide (for example, $ReO_3$, etc.). Examples of the metal halide may include an alkali metal halide, an alkaline earth metal halide, a transition metal halide, a post-transition metal halide, and a lanthanide metal halide. Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$. Examples of the transition metal halide may include a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhI_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), and a gold halide (for example, AuF, AuCl, AuBr, Auf, etc.).

Examples of the post-transition metal halide may include a zinc halide (for example, $ZnF_2$, $ZnCl_2$, $ZnBr_2$, $ZnI_2$, etc.), an indium halide (for example, $InI_3$, etc.), and a tin halide (for example, $SnI_2$, etc.).

Examples of the lanthanide metal halide may include YbF, $YbF_2$, $YbF_3$, $SmF_3$, YbCl, $YbCl_2$, $YbCl_3$, $SmCl_3$, YbBr, $YbBr_2$, $YbBr_3$ $SmBr_3$, YbI, $YbI_2$, $YbI_3$, and $SmI_3$. Examples of the metalloid halide may include an antimony halide (for example, $SbCl_5$, etc.).

Examples of the metal telluride may include an alkali metal telluride (for example, $Li_2Te$, a $na_2Te$, $K_2Te$, $Rb_2Te$, $Cs_2Te$, etc.), an alkaline earth metal telluride (for example, BeTe, MgTe, CaTe, SrTe, BaTe, etc.), a transition metal telluride (for example, $TiTe_2$, $ZrTe_2$, $HfTe_2$, $V_2Te_3$, $Nb_2Te_3$, $TaZTe_3$, $CrZTe_3$, $MoZTe_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), a post-transition metal telluride (for example, ZnTe, etc.), and a lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device 10, the emission layer may be patterned into a red emission layer, a green emission layer, and/or a blue emission layer, according to a subpixel. In one or more embodiments, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include hosts and a dopant. The hosts and the dopant may satisfy Equation (1). In addition, the hosts and the dopant may satisfy Equation (2) and/or Equation (3). In an embodiment, the amount of the dopant may be from about 0.01 parts by weight to about 30 parts by weight based on 100 parts by weight of the entire host. In an embodiment, the amount of the dopant may be from about 0.01 parts by weight to about 15 parts by weight based on 100 parts by weight of the entire host. The weight ratio of a first host to a second host may be the same as described above.

The thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Host

The host may include, as an electron-transporting host, a compound represented by Formula 1:

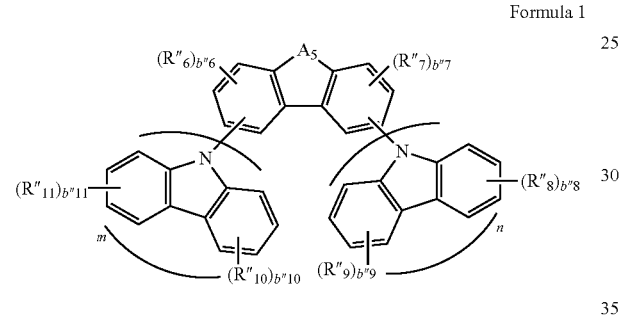

Formula 1 wherein, in Formula 1, $A_5$ is O, S, $NR''_{12}$, or $CR''_{13}R''_{14}$, m and n may each independently be selected from 0 to 4, $R''_6$ to $R''_{14}$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_8$-$C_{60}$ monovalent non-aromatic condensed polycyclic group unsubstituted or substituted with at least one $R_{10a}$, a $C_1$-$C_{60}$ monovalent non-aromatic condensed heteropolycyclic group unsubstituted or substituted with at least one $R_{10a}$, —Si(Q_1)(Q_2)(Q_3), —B(Q_1)(Q_2), —N(Q_1)(Q_2), —P(Q_1)(Q_2), —C(=O)(Q_1), —S(=O)(Q_1), —S(=O)_2(Q_1), —P(=O)(Q_1)(Q_2), and —P(=S)(Q_1)(Q_2), and b"6 to b"11 may each independently be an integer from 0 to 4.

When b"6 in Formula 1 is 2, 3 or 4, a plurality of $R''_6(s)$ may be identical to or different from each other. When b"7 is 2, 3 or 4, a plurality of $R''_7(s)$ may be identical to or different from each other. When b"8 is 2, 3 or 4, a plurality of $R''_8(s)$ may be identical to or different from each other. When b"9 is 2, 3 or 4, a plurality of $R''_9(s)$ may be identical to or different from each other. When b"10 is 2, 3 or 4, a plurality of $R''_{10}(s)$ may be identical to or different from each other. When b"11 is 2, 3 or 4, a plurality of $R''_{11}(s)$ may be identical to or different from each other.

Two neighboring substituents among $R''_6$ to $R''_{14}$ in Formula 1 may optionally be linked to each other to form a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$.

In an embodiment, the compound represented by Formula 1 may be one of the following compounds:

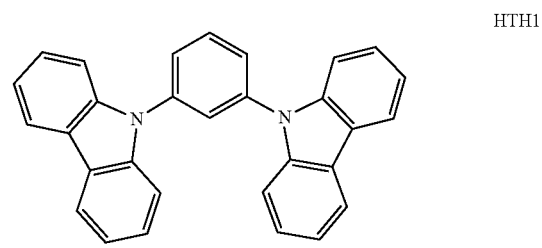

HTH1

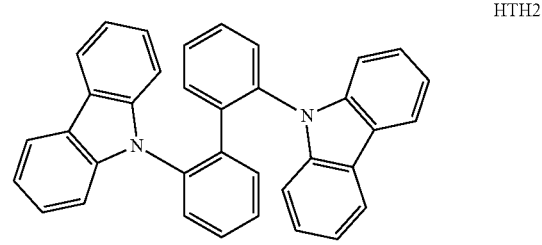

HTH2

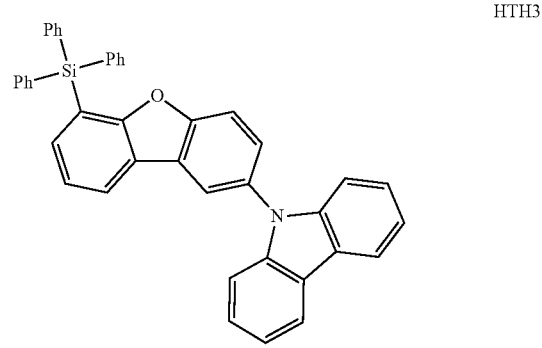

HTH3

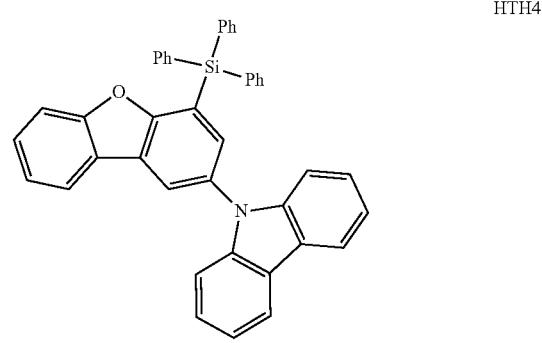

HTH4

HTH5
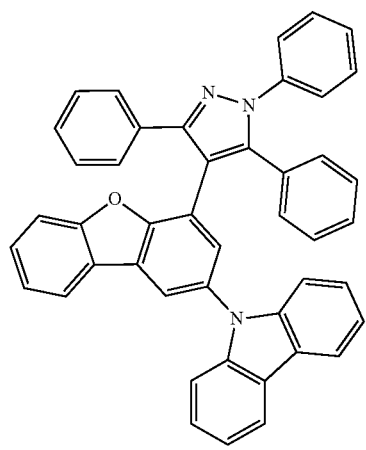
HTH6
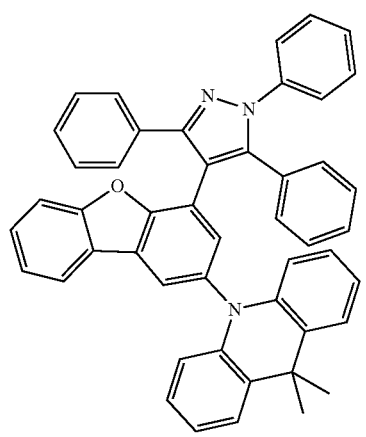
HTH7
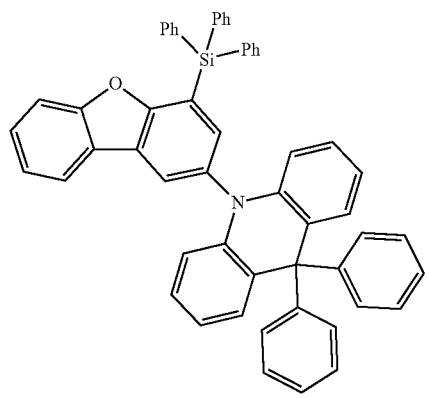
HTH8
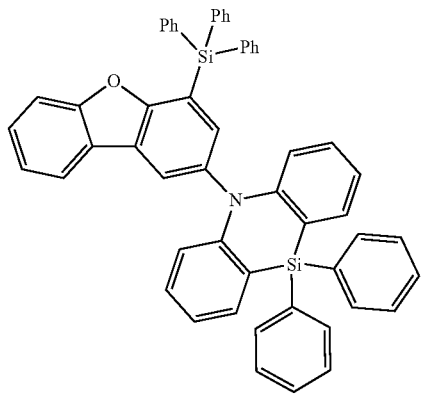
HTH9
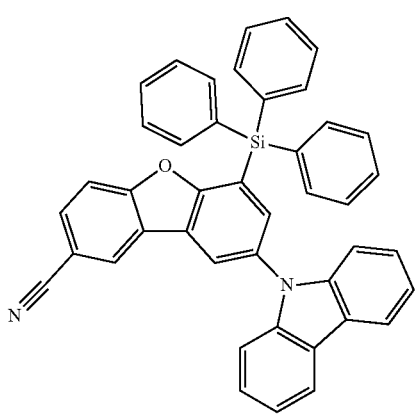
HTH10
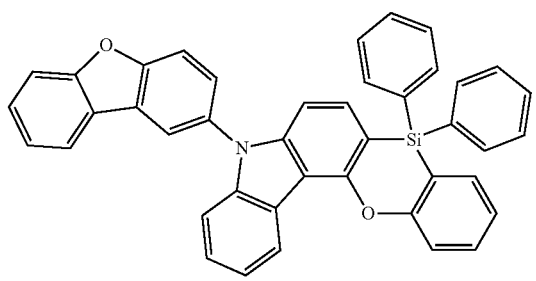
HTH11
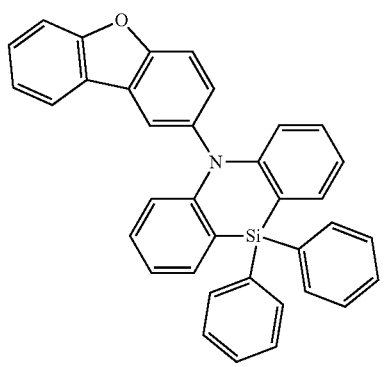

HTH12
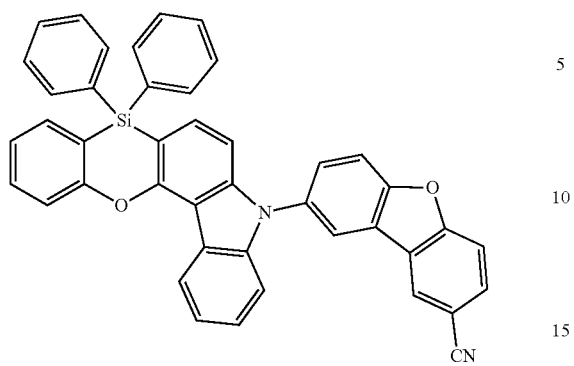
HTH13
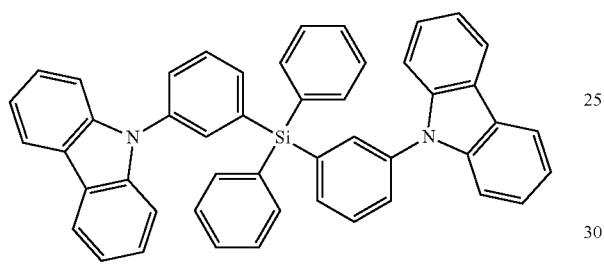
HTH14
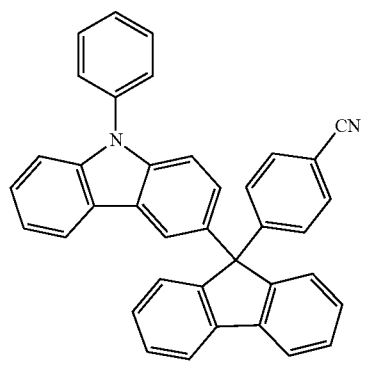
HTH15
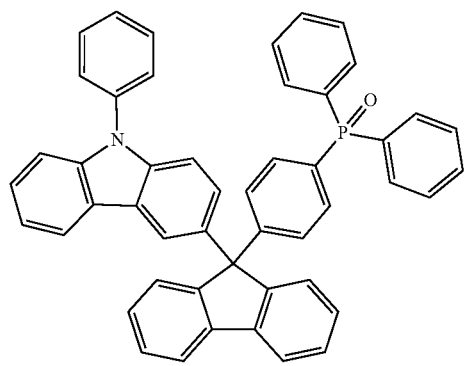
HTH16
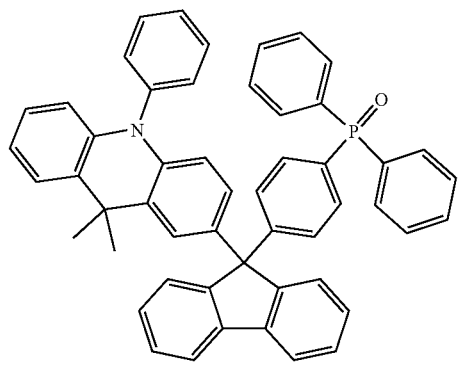
HTH17
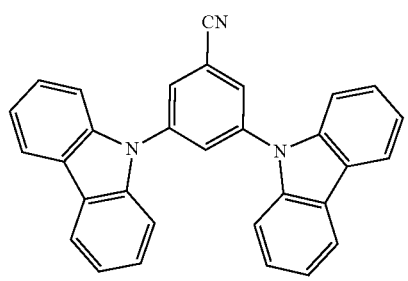
HTH18
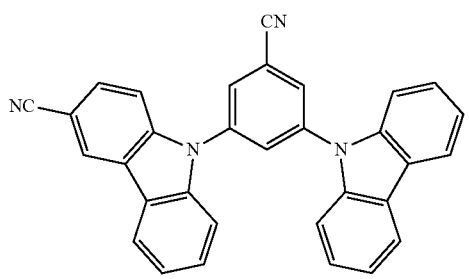
HTH19
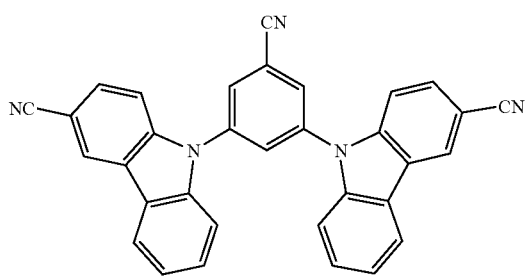
HTH20
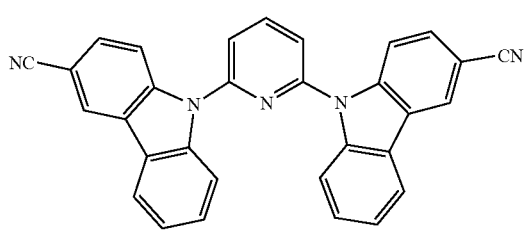

HTH21
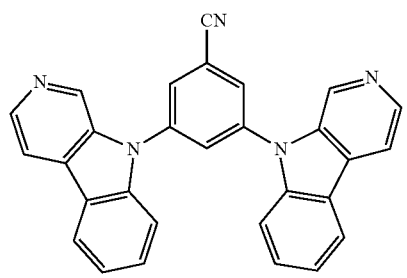
HTH22
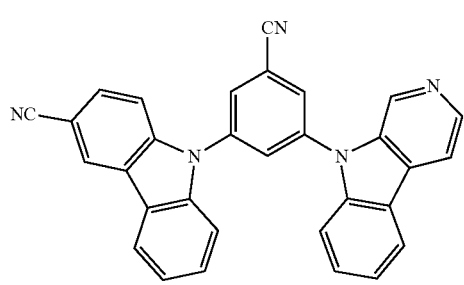
HTH23
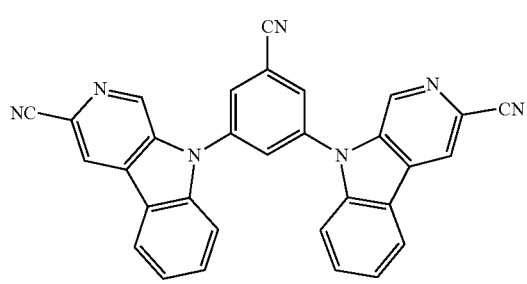
HTH24
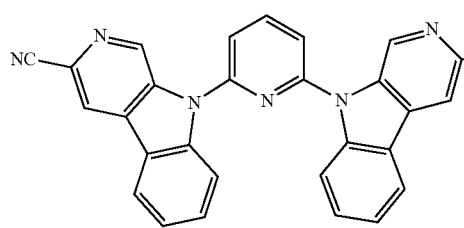
HTH25
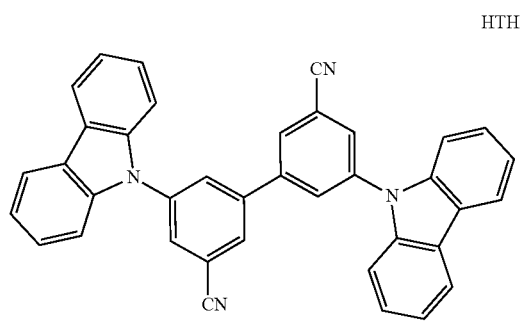
HTH26
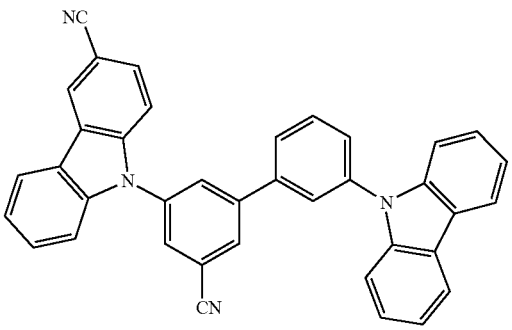
HTH27
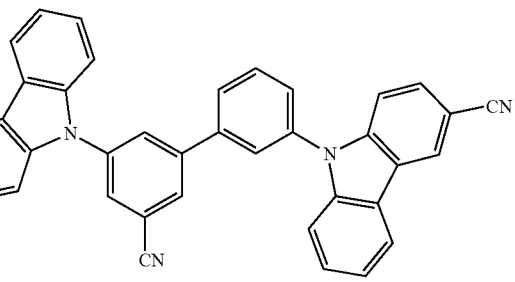
HTH28
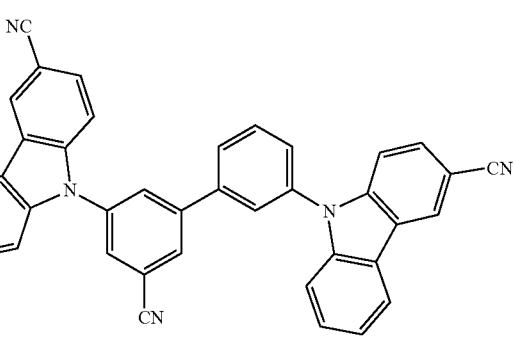
HTH29
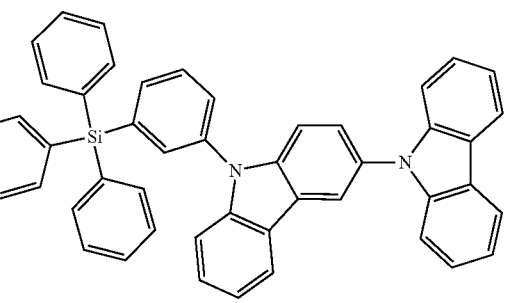

HTH30
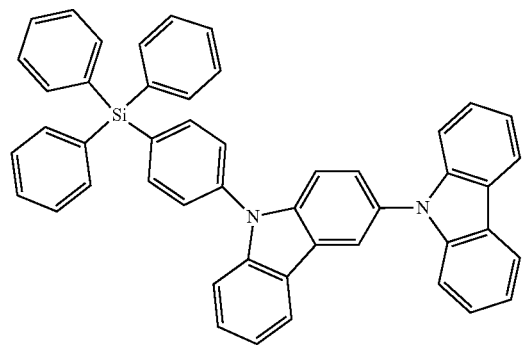
HTH31
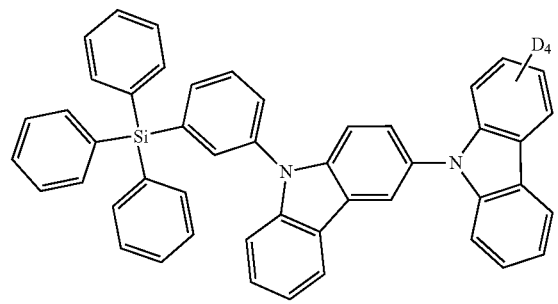
HTH32
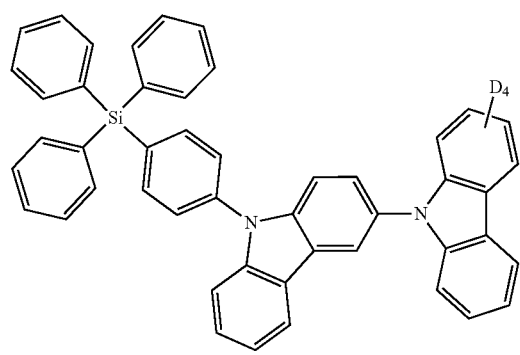
HTH33
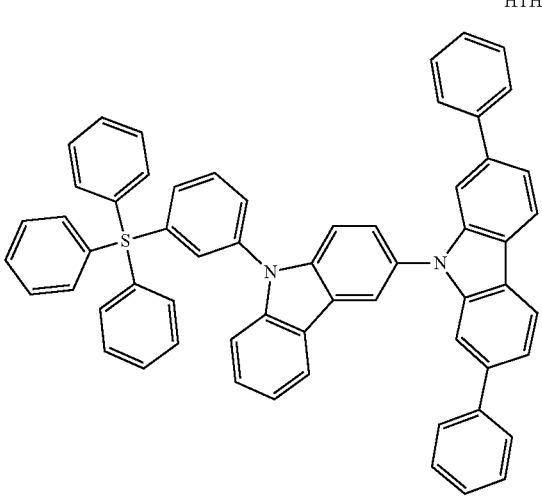
HTH34
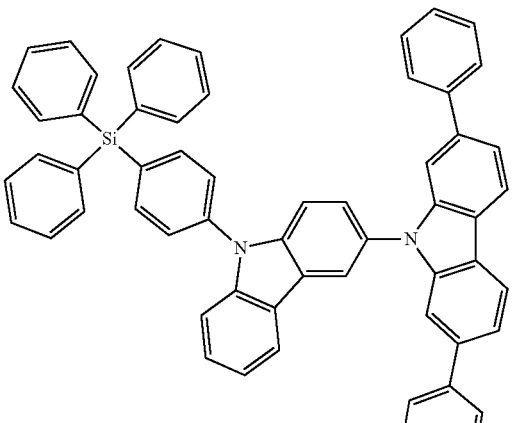
HTH35
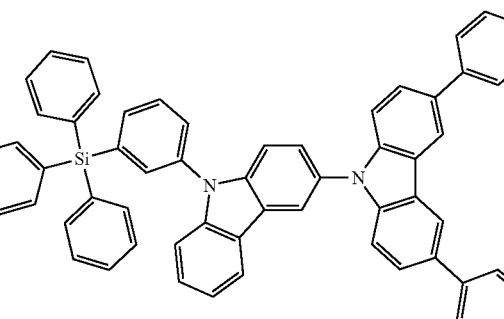
HTH36
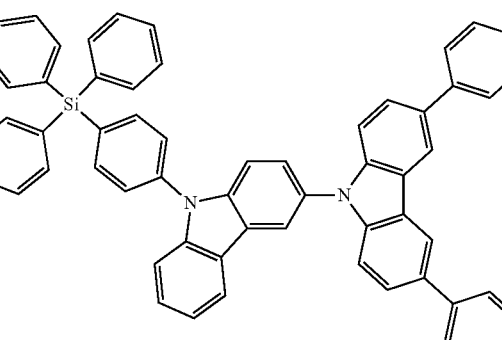
HTH37
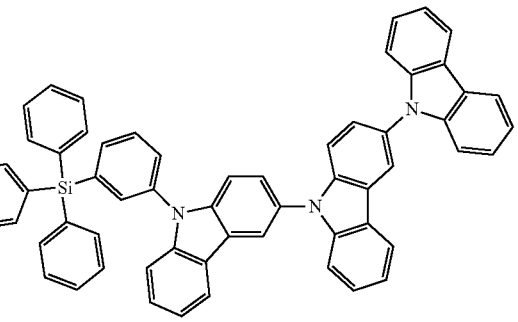

HTH38
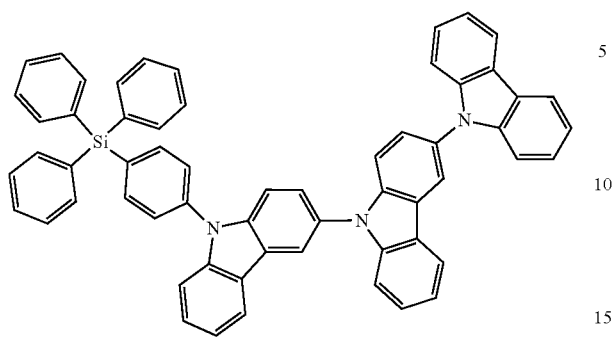
HTH39
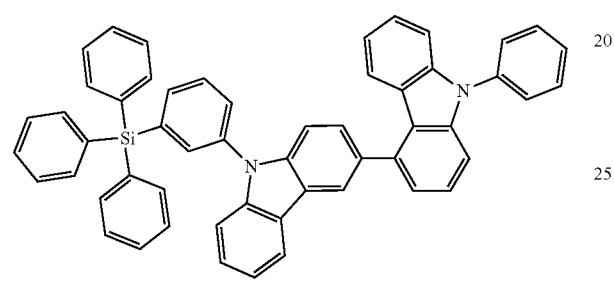
HTH40
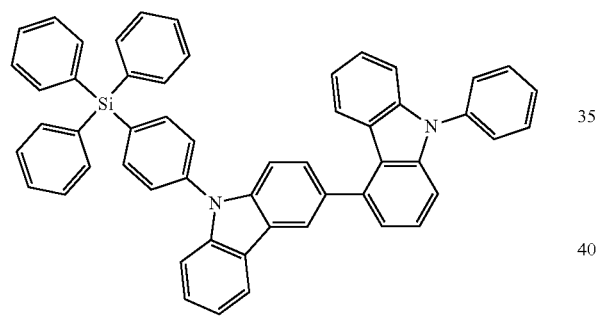
HTH41
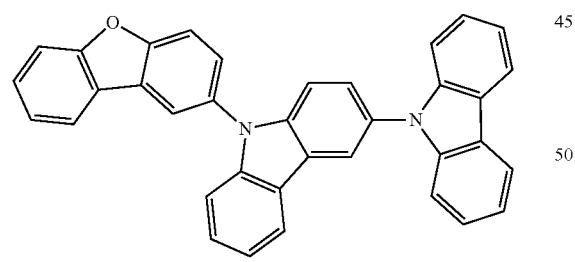
HTH42
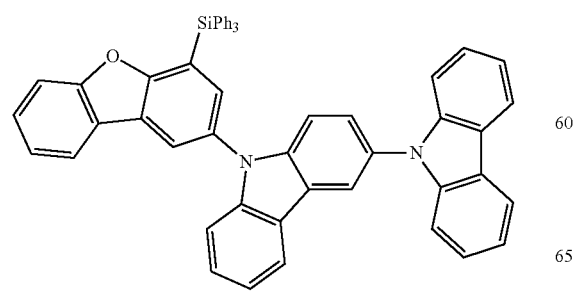
HTH43
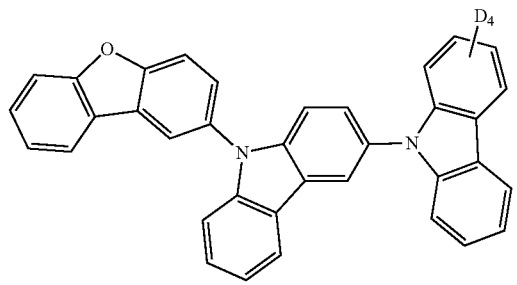
HTH44
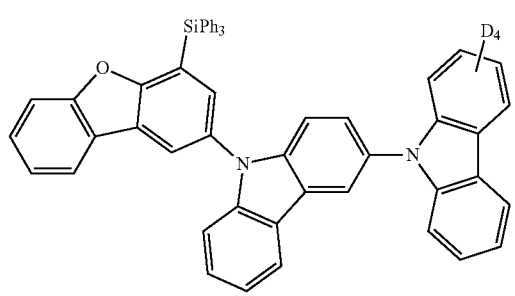
HTH45
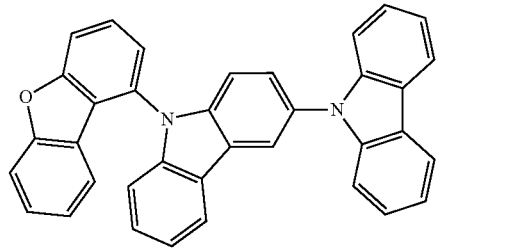
HTH46
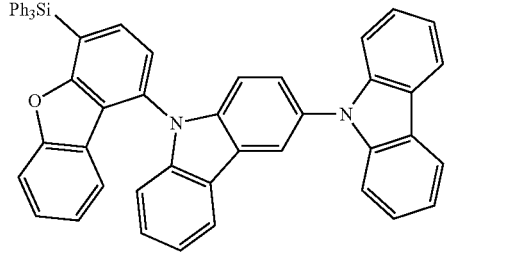
HTH47
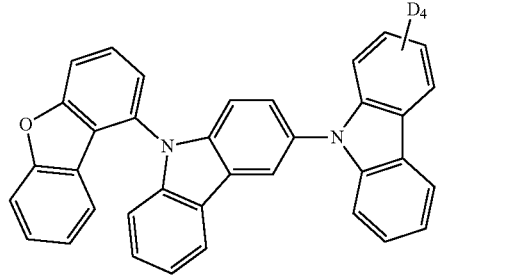

HTH48

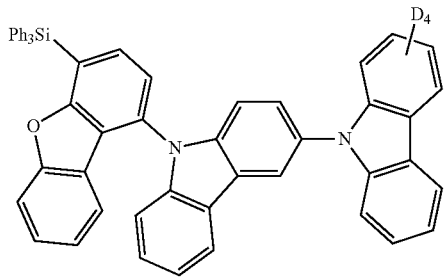

HTH49

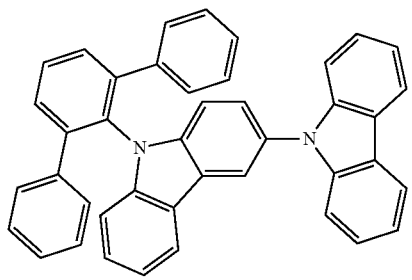

HTH50

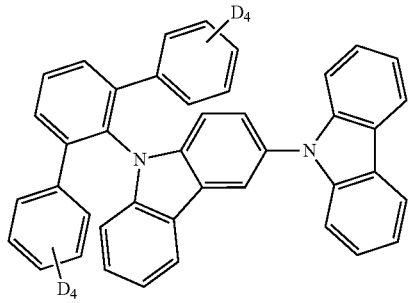

HTH51

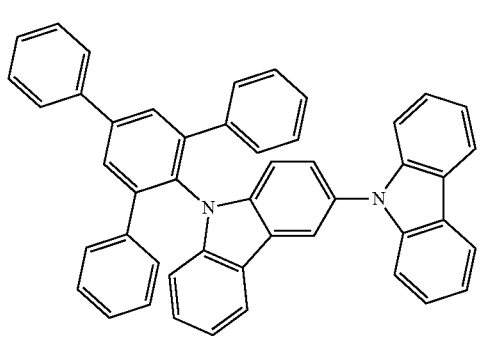

HTH52

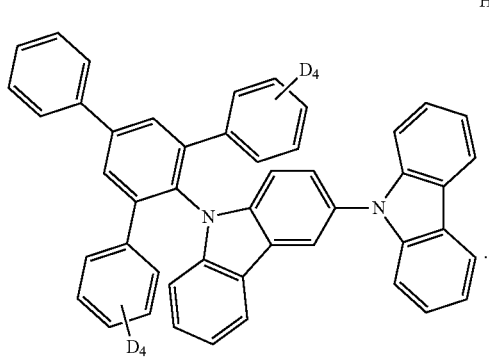

The host may include, as a hole-transporting host, a compound represented by Formula 2:

Formula 2

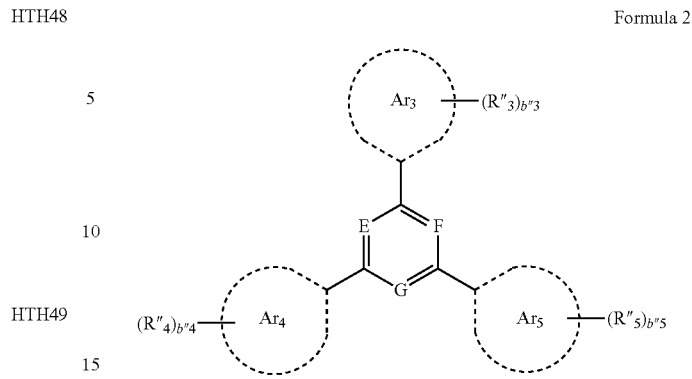

wherein, in Formula 2, ring $Ar_3$ to ring $Ar_5$ may each independently be selected from a $C_5$-$C_{60}$ carbocyclic group and a $C_1$-$C_{60}$ heterocyclic group, E may be N or $CR''_6$, F may be N or $CR''_7$, and G may be N or $CR''_8$, $R''_3$ to $R''_8$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_8$-$C_{60}$ monovalent non-aromatic condensed polycyclic group unsubstituted or substituted with at least one $R_{10a}$, a $C_1$-$C_{60}$ monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and b"3 to b"5 may each independently be an integer from 1 to 5.

When b"3 in Formula 2 is 2, 3, 4, or 5, a plurality of $R''_3(s)$ may be identical to or different from each other. When b"4 is 2, 3, 4, or 5, a plurality of $R''_4(s)$ may be identical to or different from each other. When b"5 is 2, 3, 4, or 5, a plurality of $R''_5(s)$ may be identical to or different from each other.

Two neighboring substituents among $R''_3$ to $R''_8$ in Formula 2 may optionally be linked to each other to form a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$.

In an embodiment, the compound represented by Formula 2 may be one of the following compounds:

ETH1
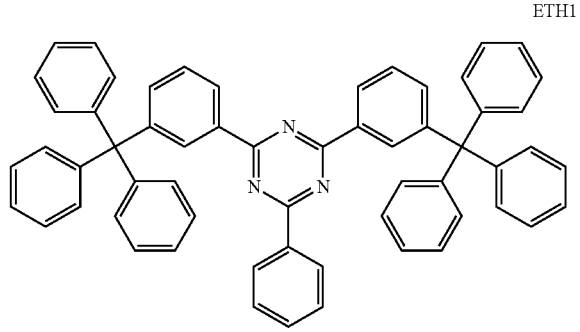
ETH6
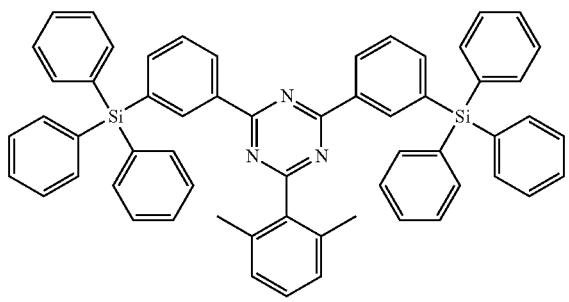
ETH2
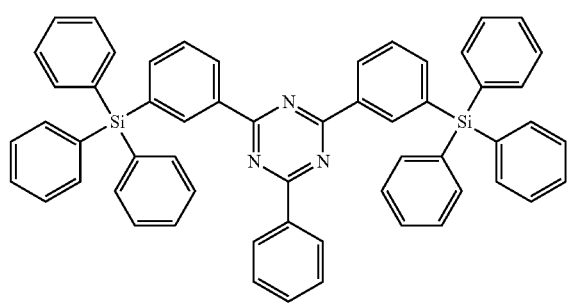
ETH7
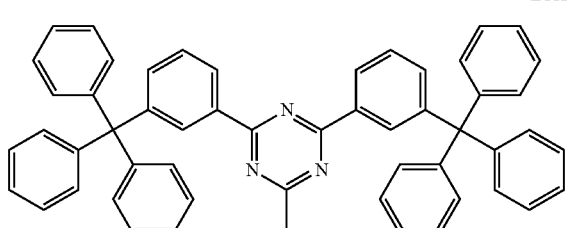
ETH3
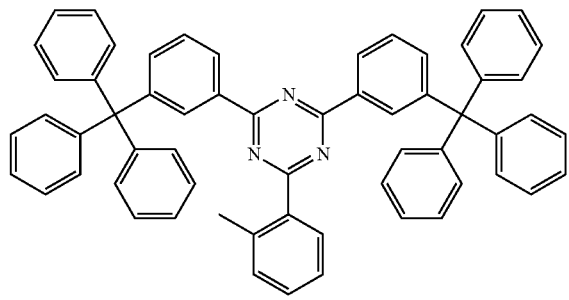
ETH4
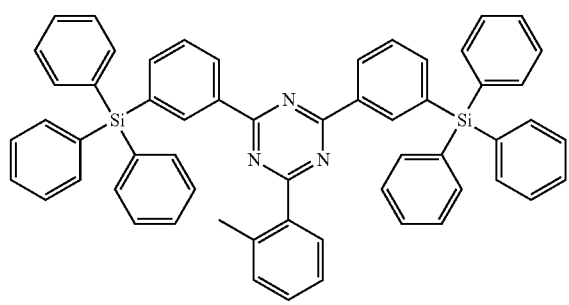
ETH8
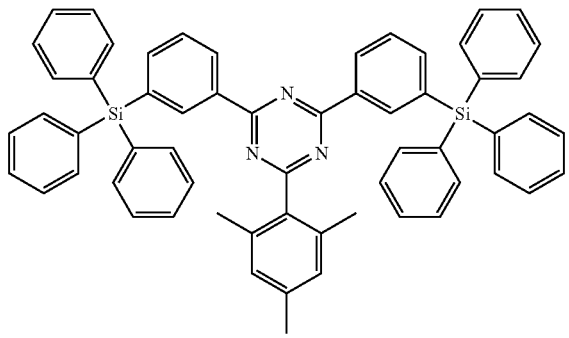
ETH5
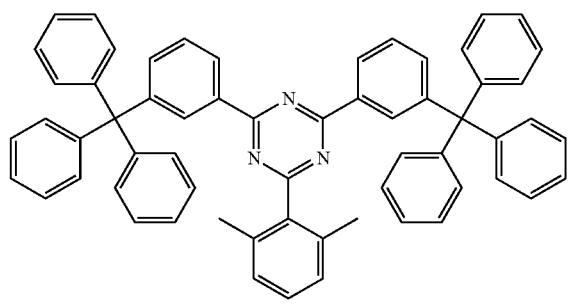
ETH9
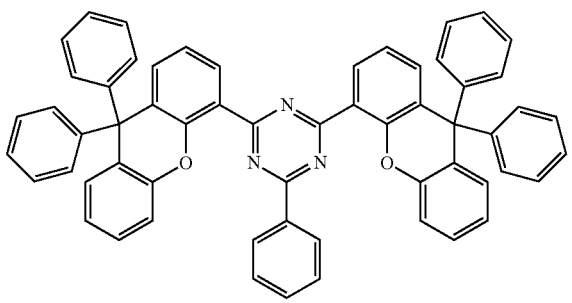

ETH10
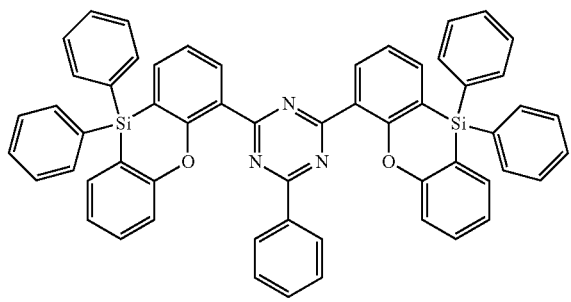
ETH15
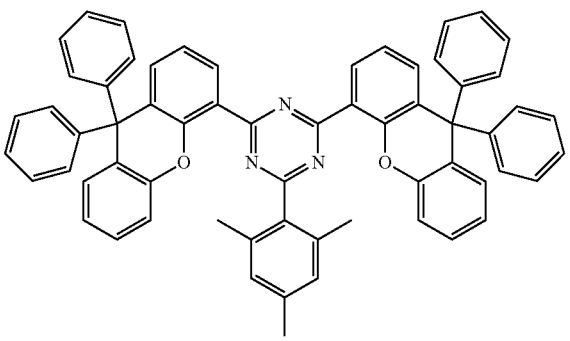
ETH11
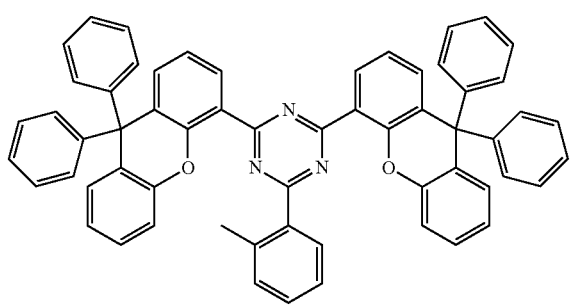
ETH12
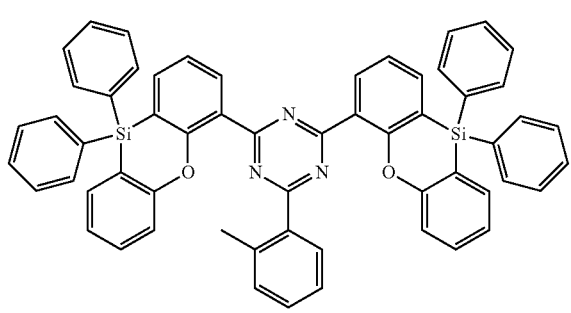
ETH16
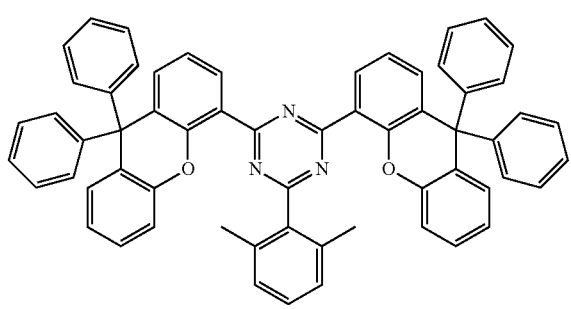
ETH13
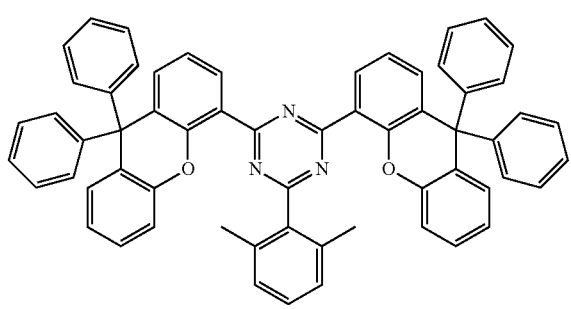
ETH17
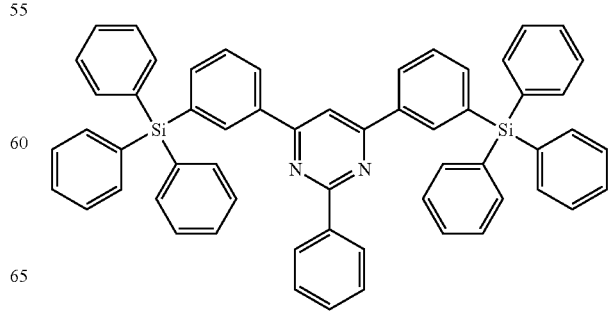
ETH14
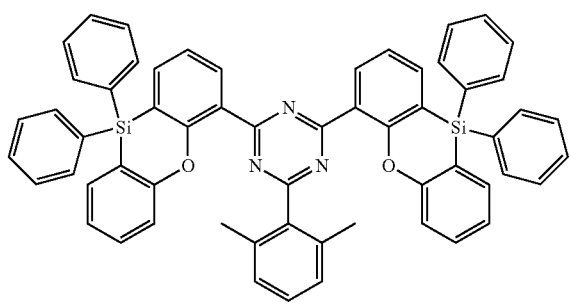
ETH18
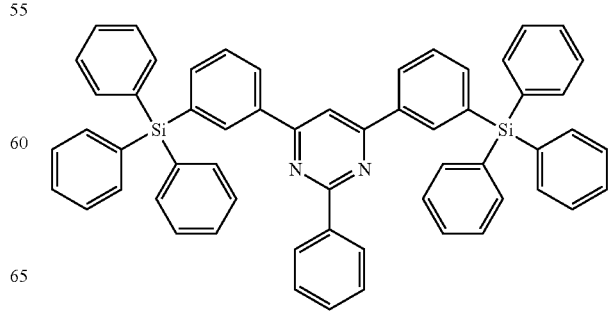

ETH19
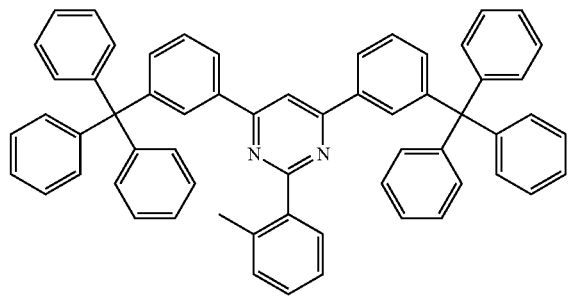
ETH20
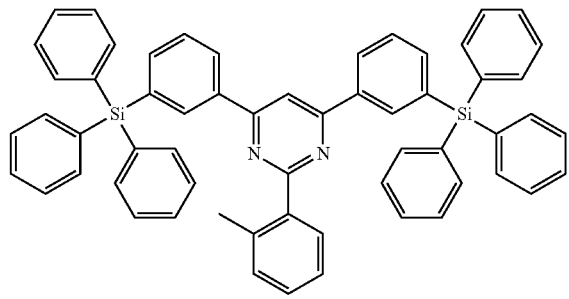
ETH21
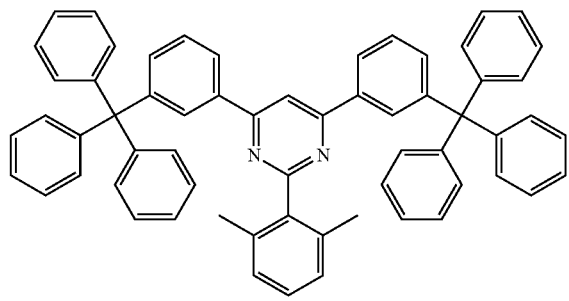
ETH22
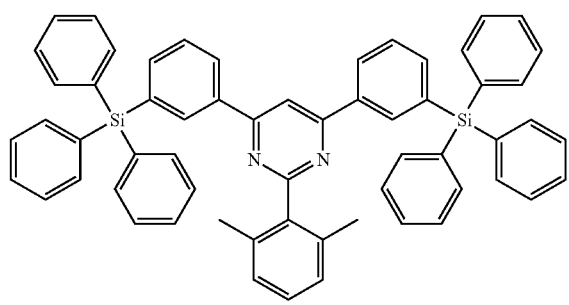
ETH23
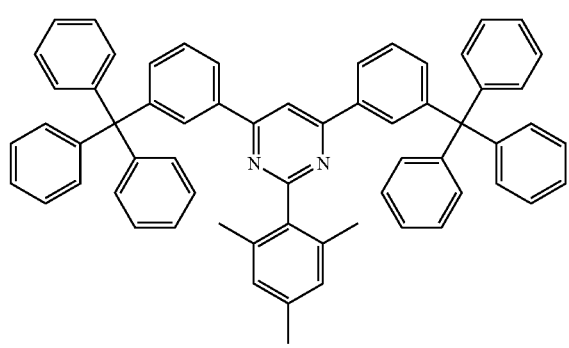
ETH24
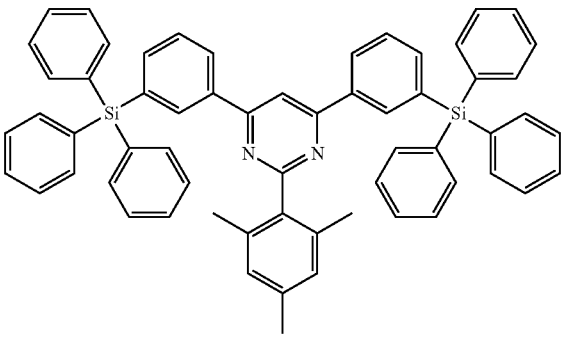
ETH25
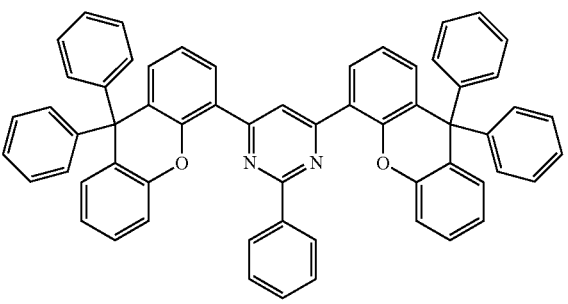
ETH26
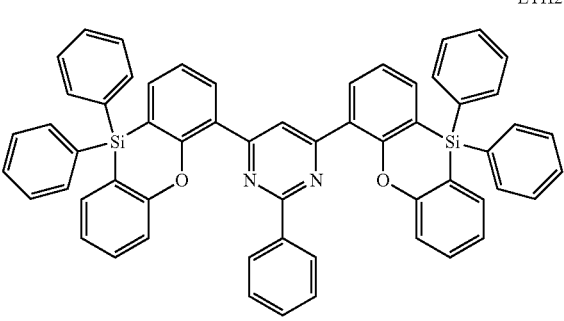
ETH27
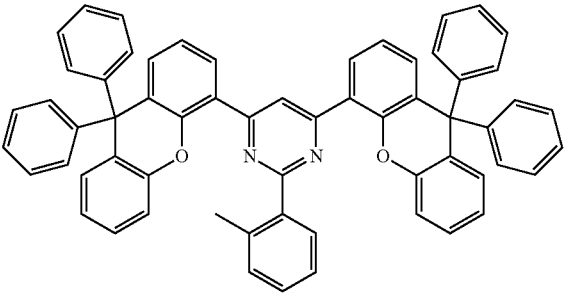
ETH28
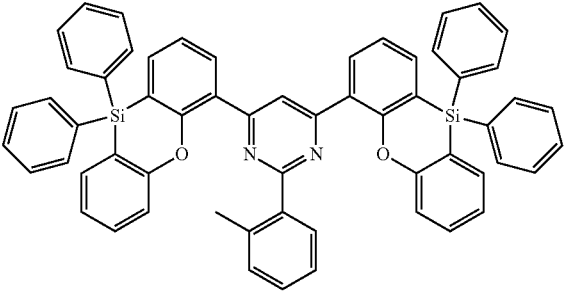

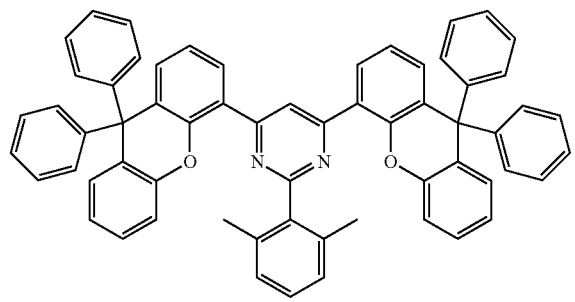
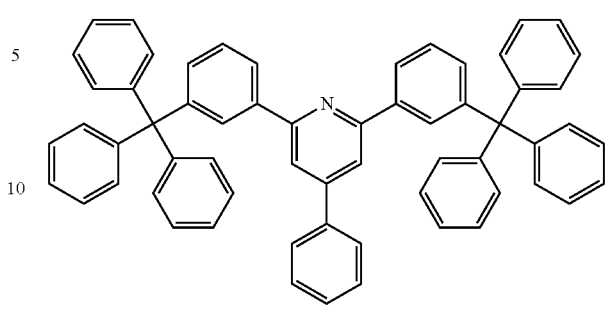

ETH38
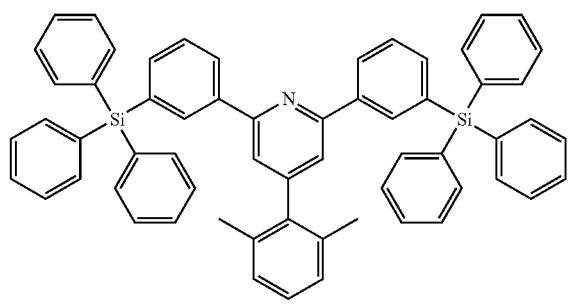
ETH39
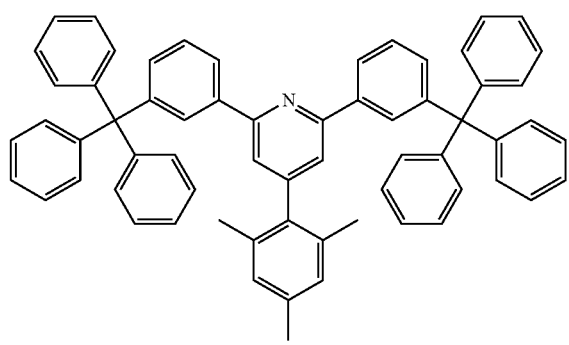
ETH40
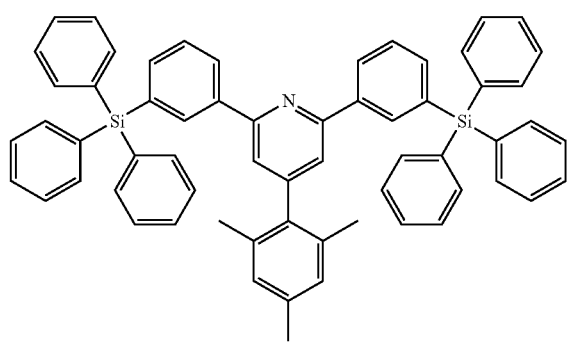
ETH41
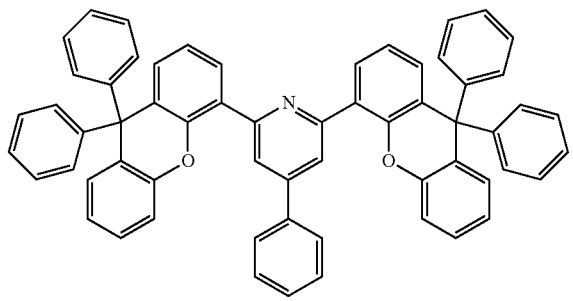
ETH42
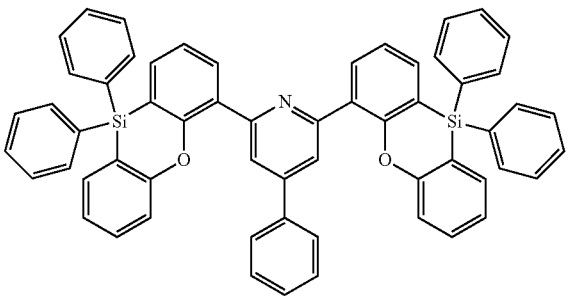
ETH43
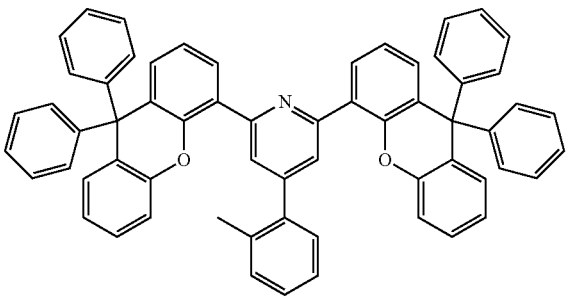
ETH44
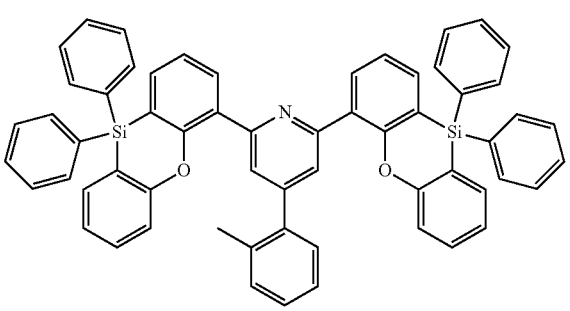
ETH45
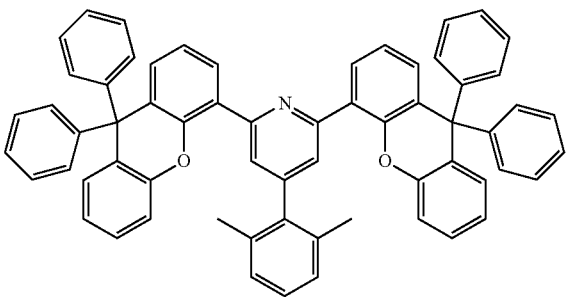
ETH46
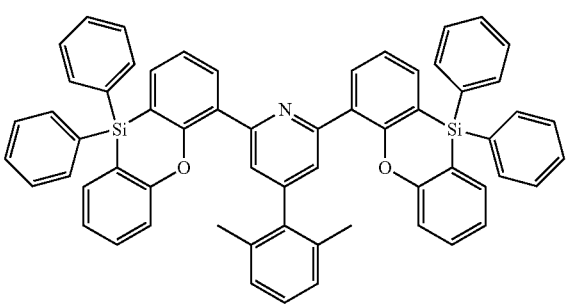

ETH47
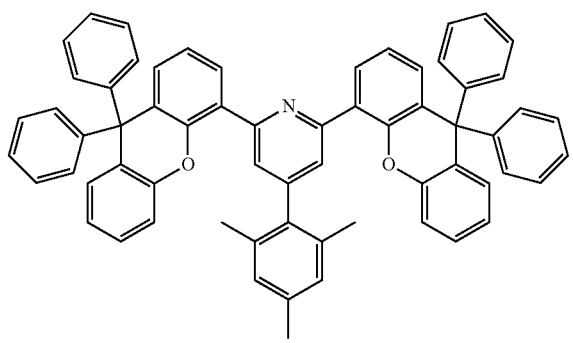
ETH51
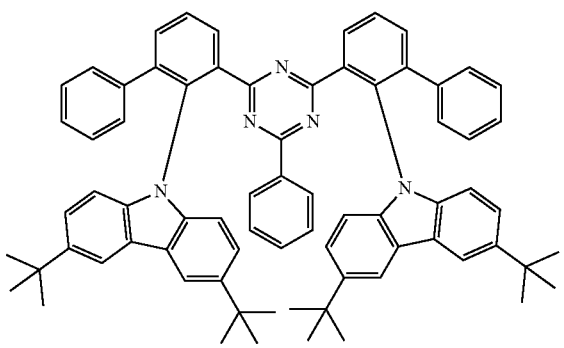
ETH48
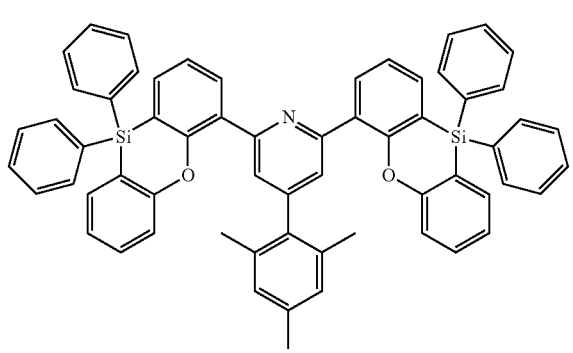
ETH52
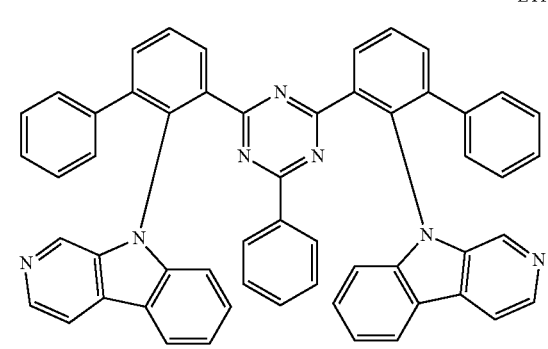
ETH49
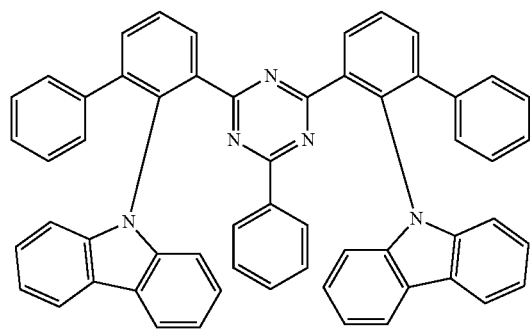
ETH53
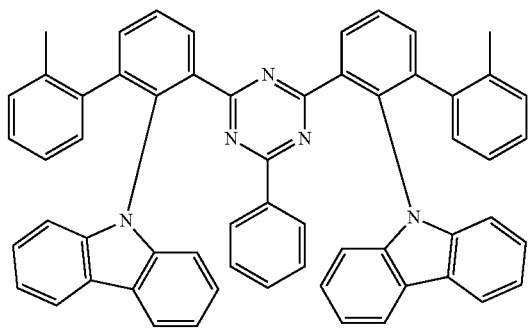
ETH50
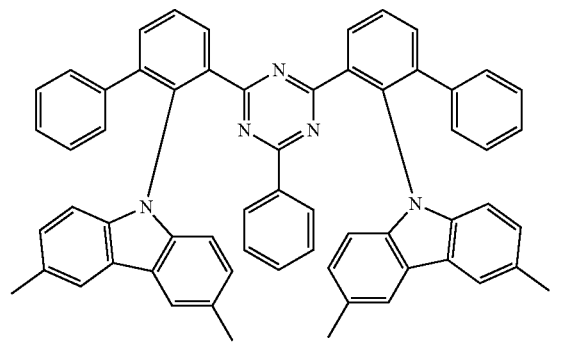
ETH54
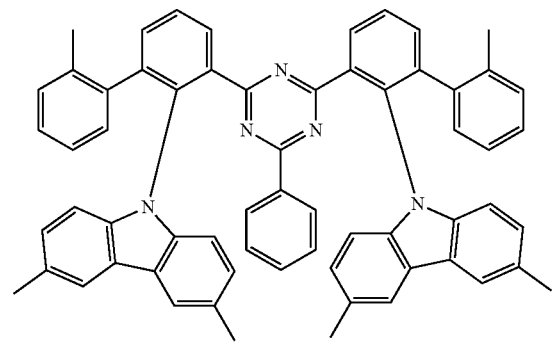

ETH55
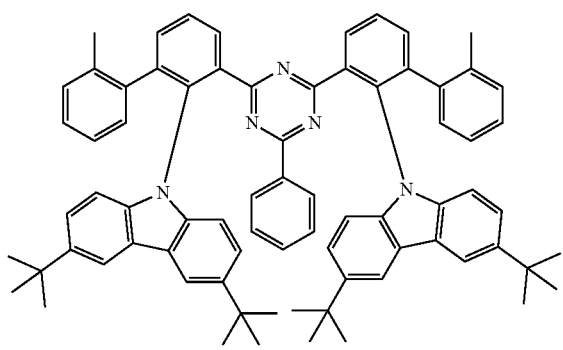
ETH59
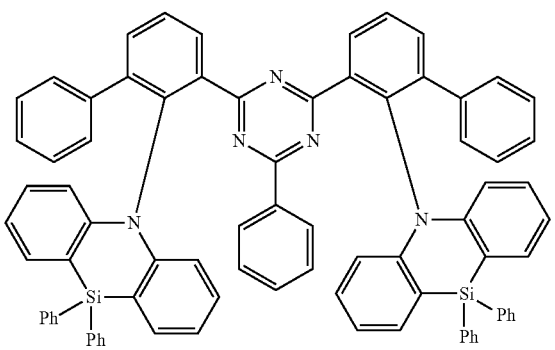
ETH56
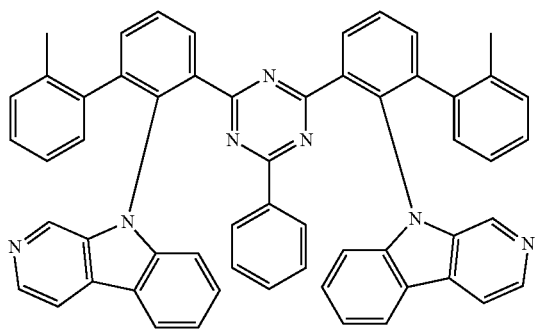
ETH60
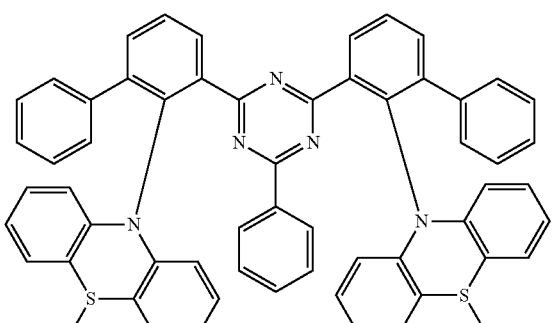
ETH57
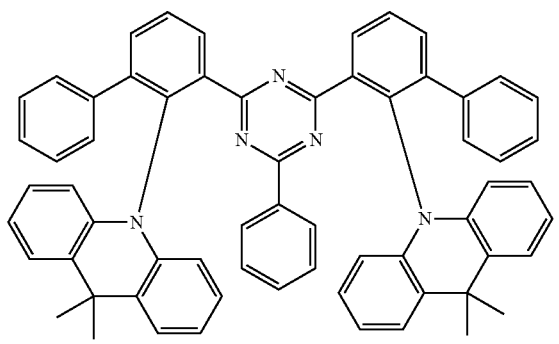
ETH61
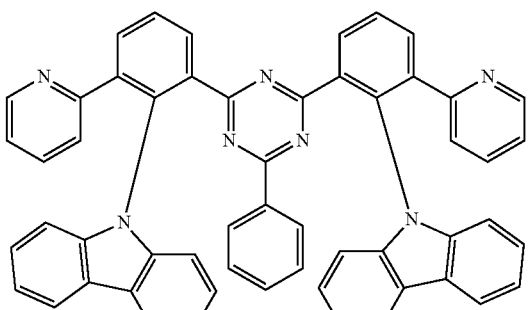
ETH58
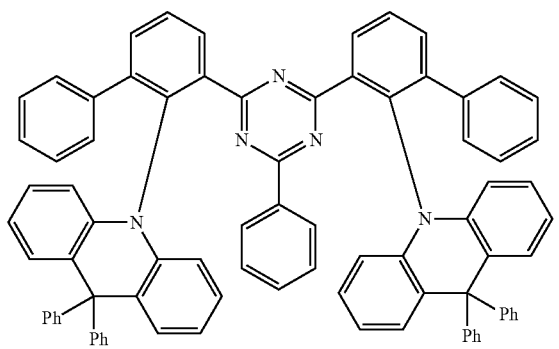
ETH62
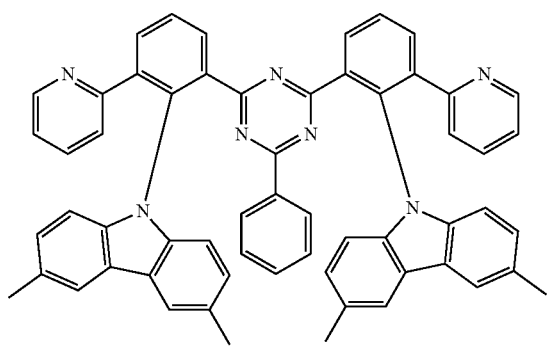

-continued
ETH63
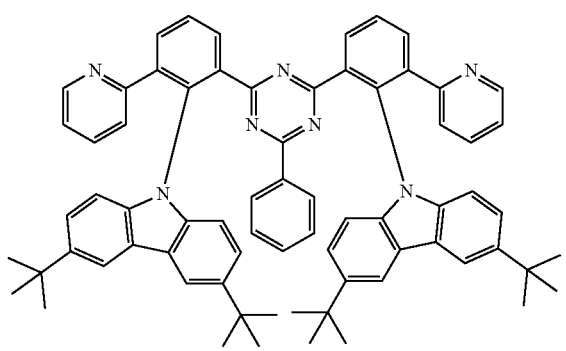
ETH64
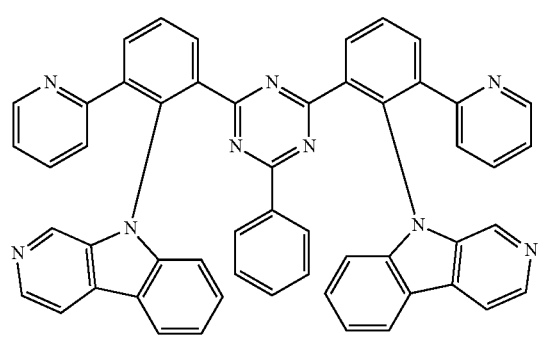
ETH65
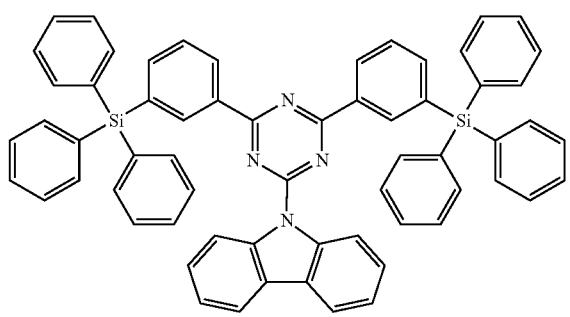
ETH66
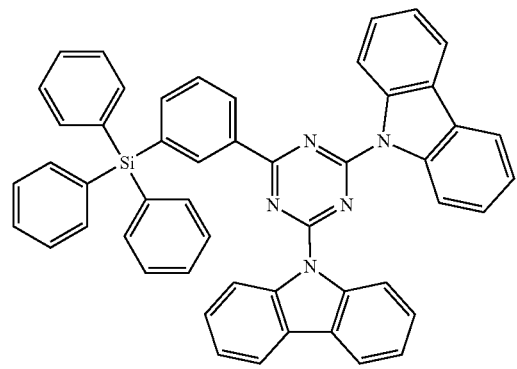
-continued
ETH67
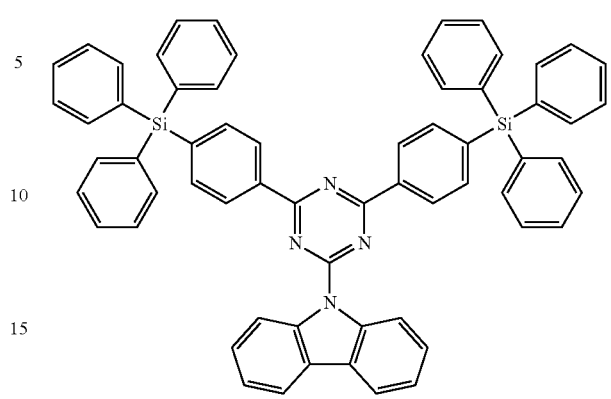
ETH68
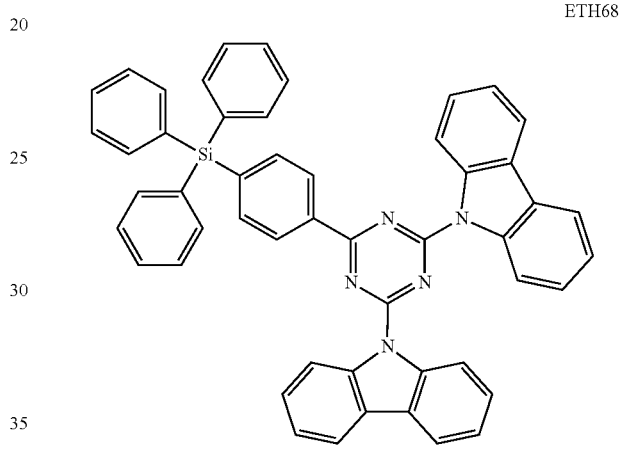
ETH69
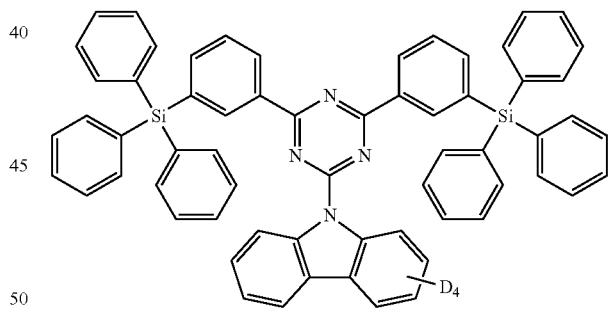
ETH70
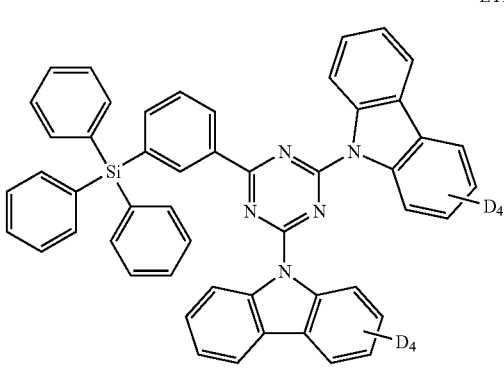

-continued
ETH71
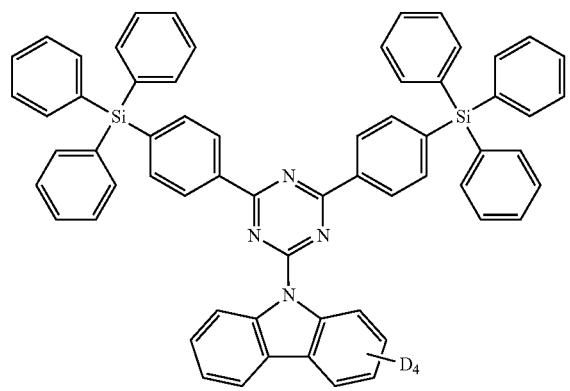
ETH72
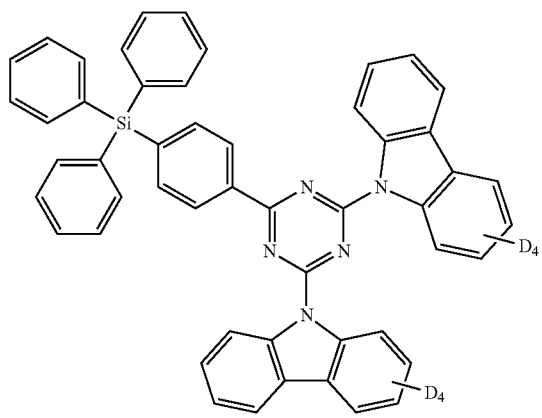
ETH73
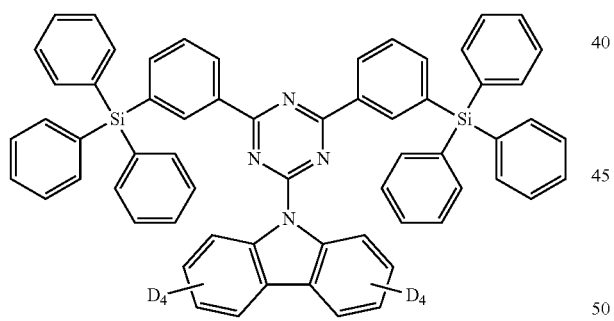
ETH74
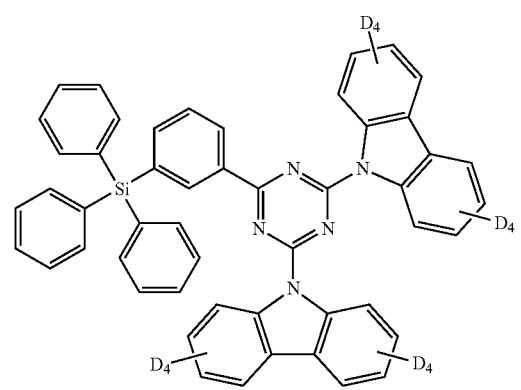
-continued
ETH75
ETH76
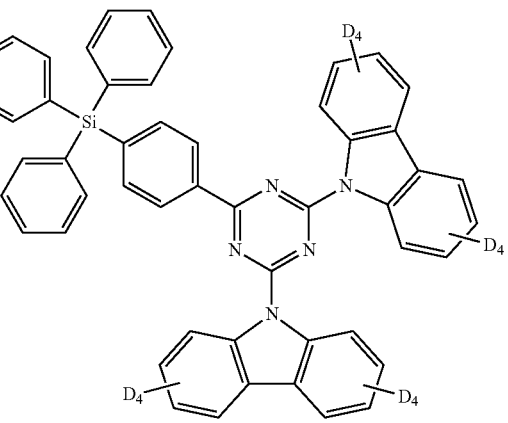
ETH77
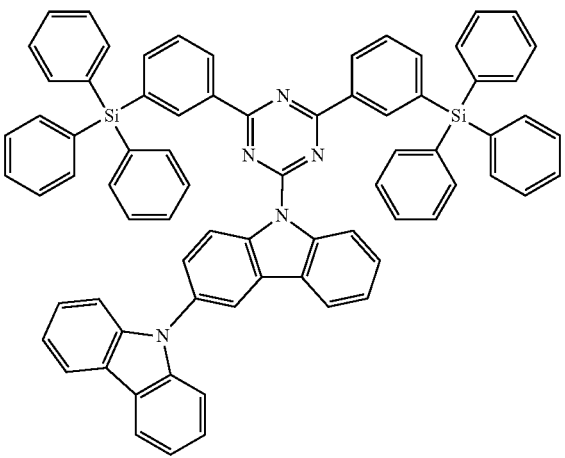

ETH78
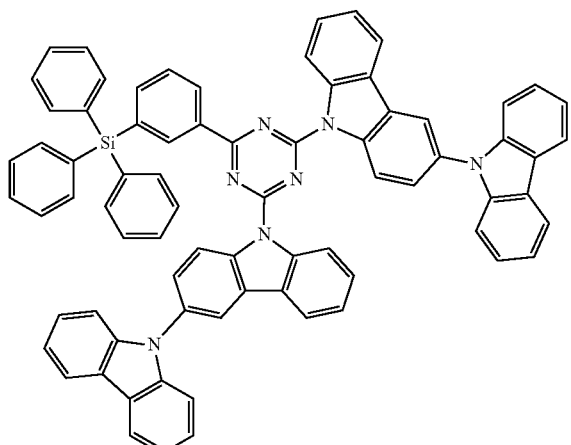
ETH79
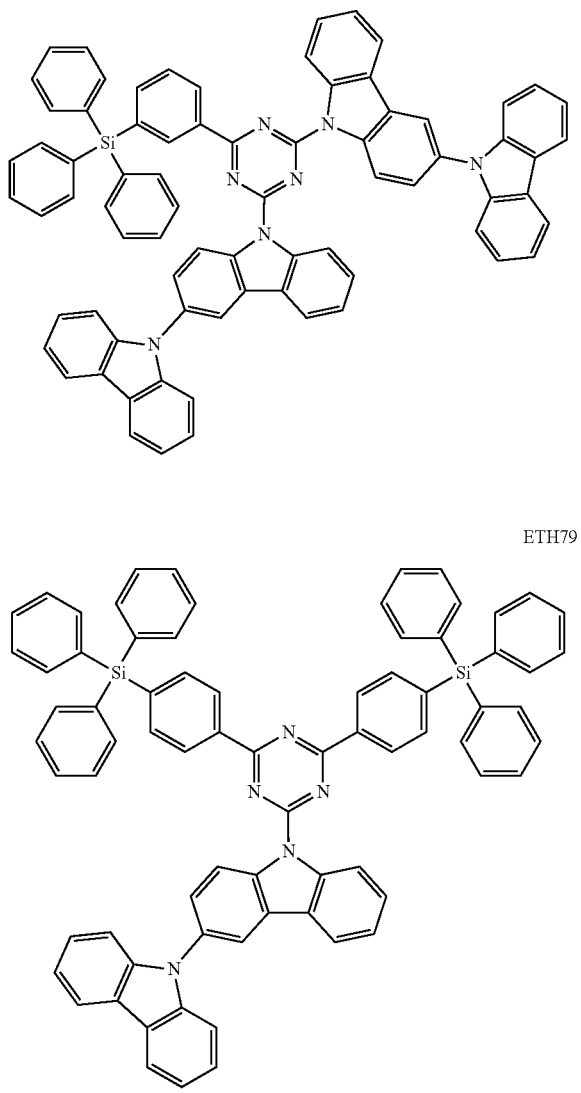
ETH80
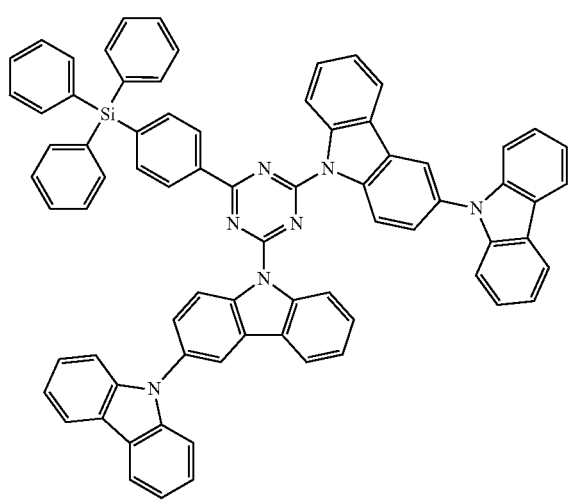
ETH81
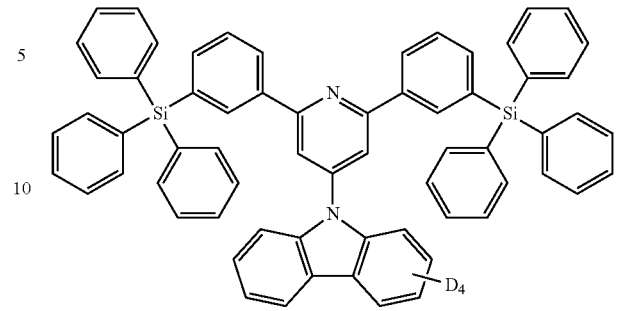
ETH82
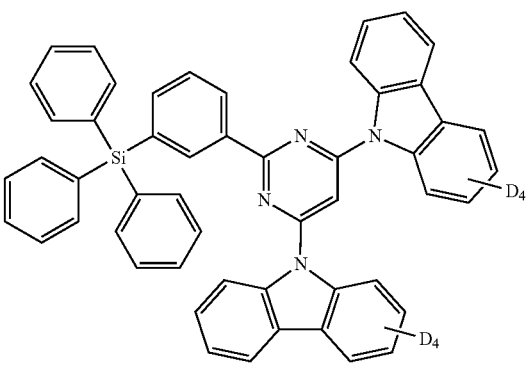
ETH83
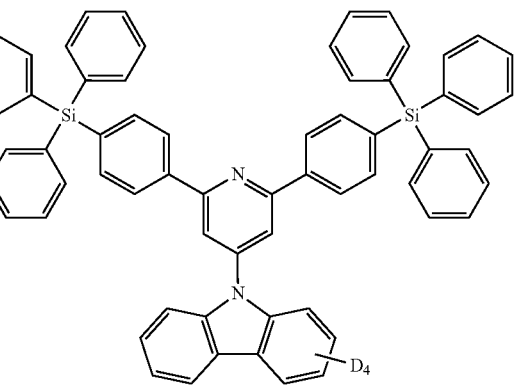
ETH84
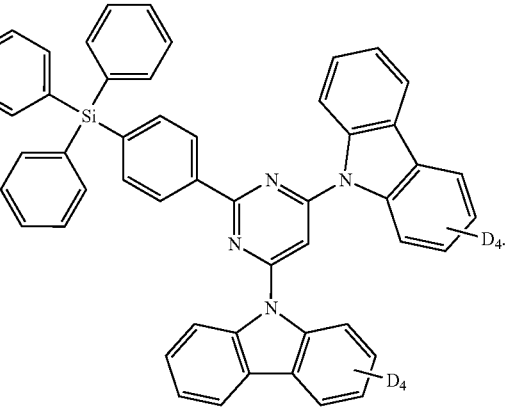
The host may include, as a hole-transporting host or an electron-transporting host, an organometallic compound represented by Formula 401. Although an organometallic compound as a phosphorescent emitter is generally a hole-transporter, a ligand or a substituent of a ligand of the organometallic compound may adjusted to lower a HOMO level, so that the organometallic compound as a phosphorescent emitter may become electron-transporting. That is, a ligand or a substituent of a ligand of the compound represented by Formula 401 may be adjusted so that the compound represented by Formula 401 may become a hole-transporting compound or an electron-transporting compound.

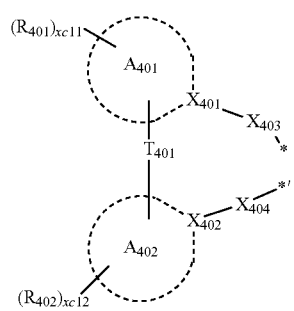

Formula 401

$M(L_{401})_{xc1}(L_{402})_{xc2}$

Formula 402 wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is 2 or more, two or more of $L_{401}(s)$ may be identical to or different from each other, $L_{402}$ may be an organic ligand, and xc2 may be 0, 1, 2, 3, or 4, wherein when xc2 is 2 or more, two or more of $L_{402}(s)$ may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-', *—C($Q_{411}$)-C($Q_{412}$)-*', *—C($Q_{411}$)-*', or *=C=*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are each the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are each the same as described in connection with $Q_1$, xc11 and xc12 may each independently be an integer from 0 to 10, and

* and *' in Formula 402 each indicate a binding site to M in Formula 401.

In an embodiment, in Formula 402, i) $X_{401}$ may be nitrogen, and $X_{402}$ may be carbon, or ii) each of $X_{401}$ and $X_{402}$ may be nitrogen.

In one or more embodiments, when xc1 in Formula 402 is 2 or more, two ring $A_{401}(s)$ in two or more of $L_{401}(s)$ may optionally be linked to each other via $T_{402}$, which is a linking group, and two ring $A_{402}(s)$ may optionally be linked to each other via $T_{403}$, which is a linking group (see Compounds PD1 to PD4 and PD7). The variables $T_{402}$ and $T_{403}$ are each the same as described in connection with $T_{401}$.

The variable $L_{402}$ in Formula 401 may be an organic ligand. In an embodiment, $L_{402}$ may include a halogen group, a diketone group (for example, an acetylacetonate group), a carboxylic acid group (for example, a picolinate group), a group —C(=O), an isonitrile group, a —CN group, a phosphorus group (for example, a phosphine group, a phosphite group, etc.), or any combination thereof.

The compound of Formula 401 may include, for example, one of Compounds PD1 to PD26, or any combination thereof:

PD1

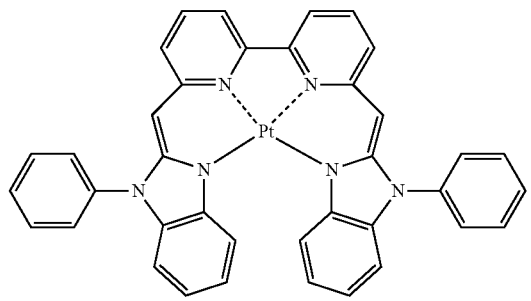

PD2

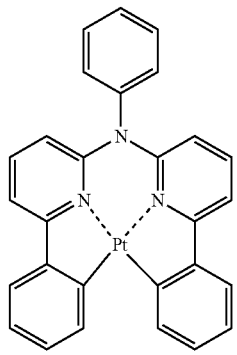

PD3

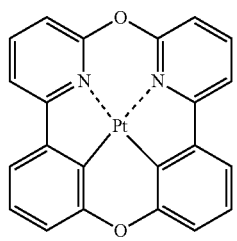

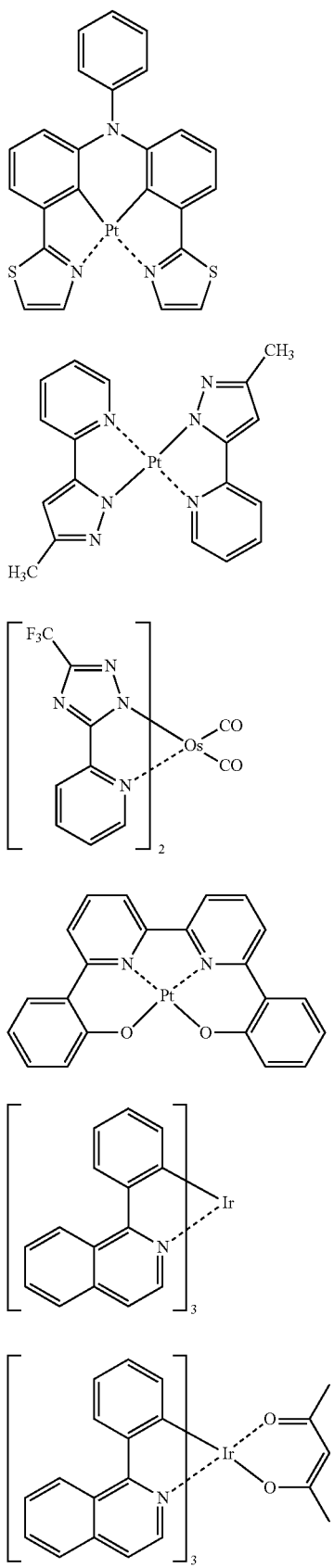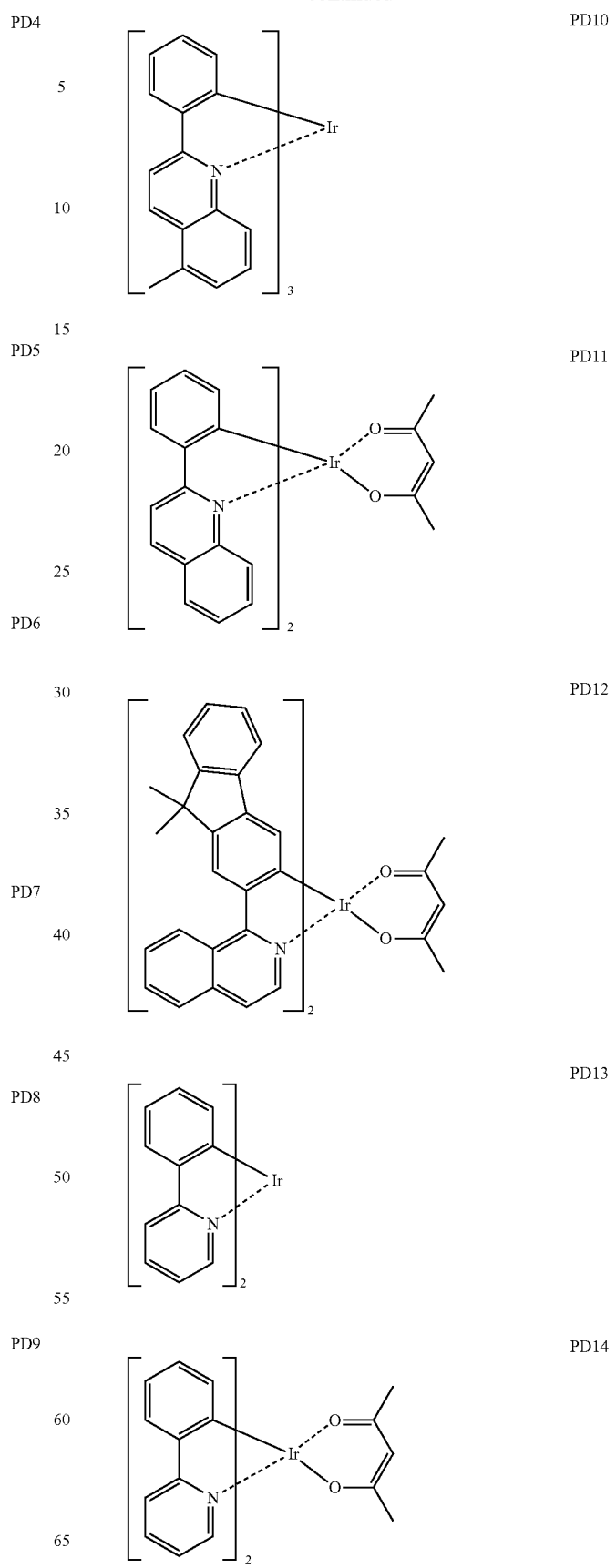

PD15 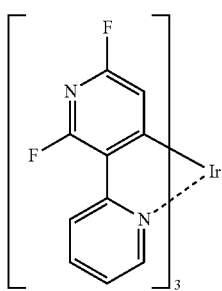
PD16 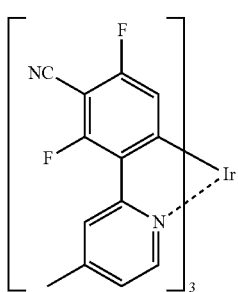
PD17 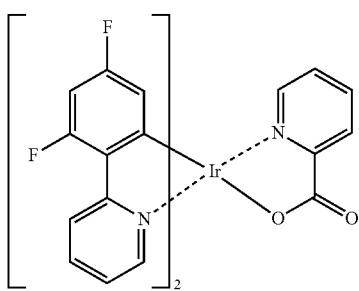
PD18 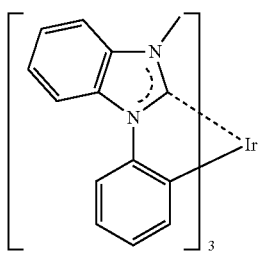
PD19 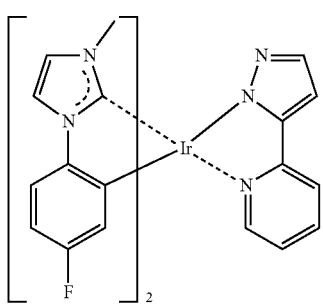
PD20 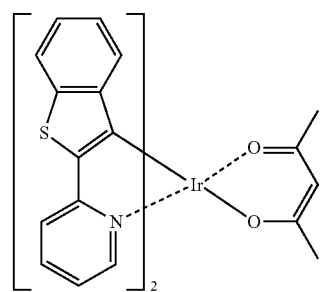
PD21 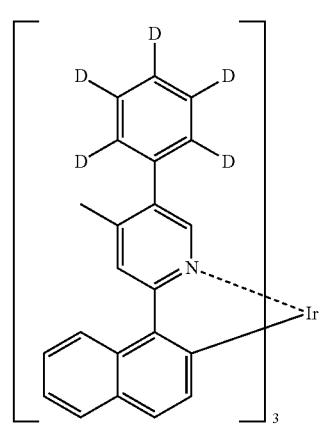
PD22 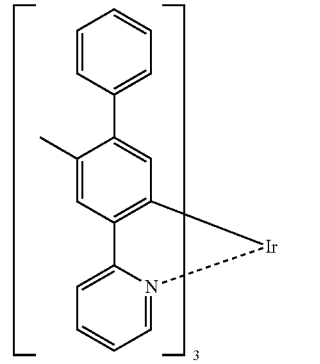
PD23 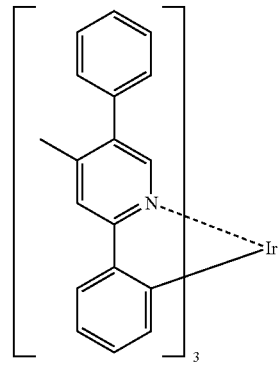

PD24

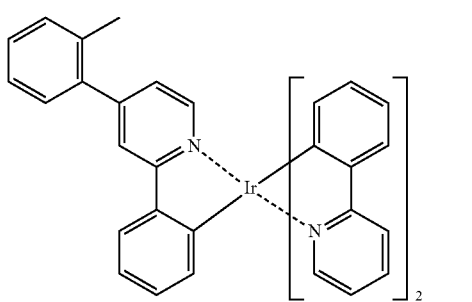

PD25

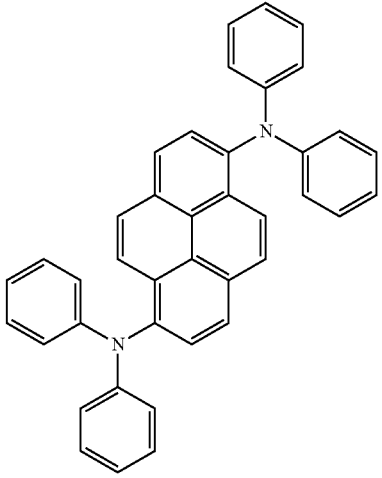

PD26

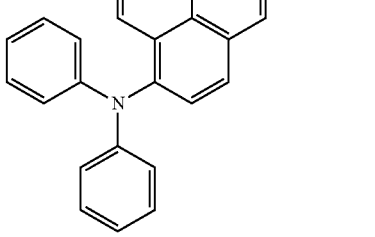

Fluorescent Dopant

The fluorescent dopant may include an amine group-containing compound, a styryl group-containing compound, or any combination thereof. In an embodiment, the fluorescent dopant may include a compound represented by Formula 501:

Formula 501

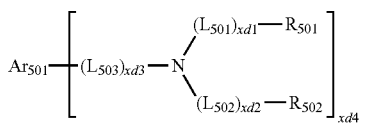

wherein, in Formula 501,

Ar$_{501}$, L$_{501}$ to L$_{503}$, R$_{501}$, and R$_{502}$ may each independently be a C$_3$-C$_{60}$ carbocyclic group unsubstituted or substituted with at least one R$_{10a}$ or a C$_1$-C$_{60}$ heterocyclic group unsubstituted or substituted with at least one R$_{10a}$, xd1 to xd3 may each independently be 0, 1, 2, or 3, and xd4 may be 1, 2, 3, 4, 5, or 6.

In an embodiment, Ar$_{501}$ in Formula 501 may be a condensed cyclic group (for example, an anthracene group, a chrysene group, or a pyrene group) in which three or more monocyclic groups are condensed together. In one or more embodiments, xd4 in Formula 501 may be 2.

In an embodiment, the fluorescent dopant may include: one of Compounds FD1 to FD36; DPVBi; DPAVBi; or any combination thereof:

FD1

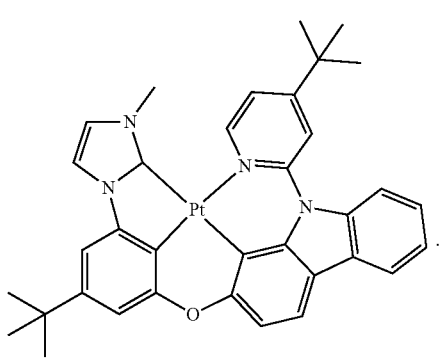

FD2

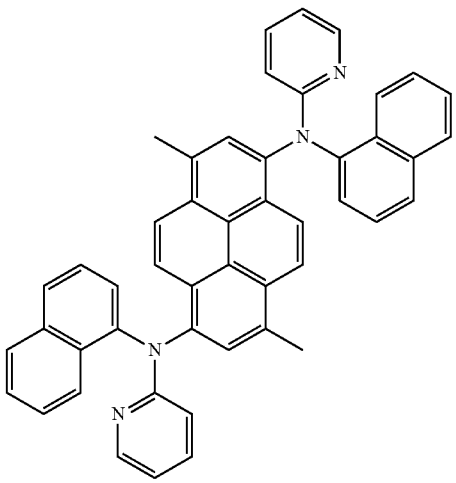

-continued
FD3
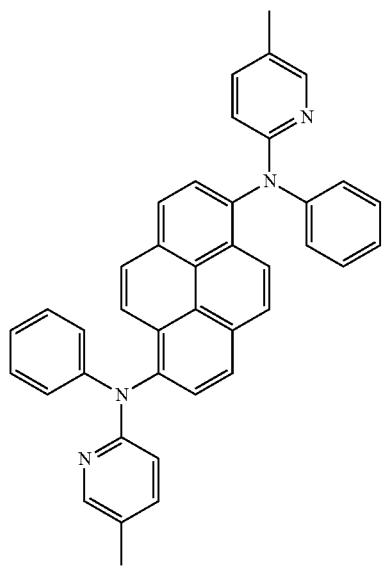
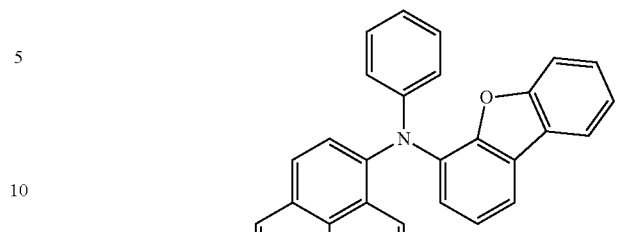
FD5
FD6
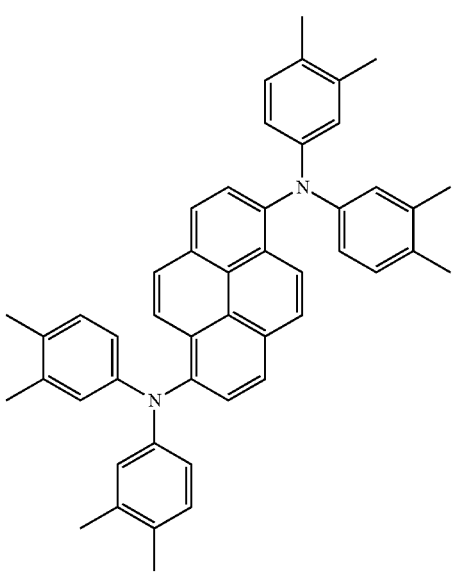
FD4
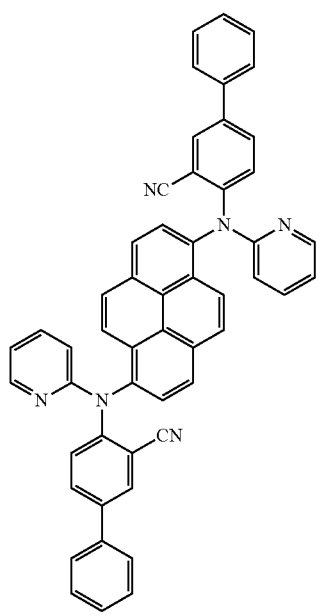
FD7

FD8
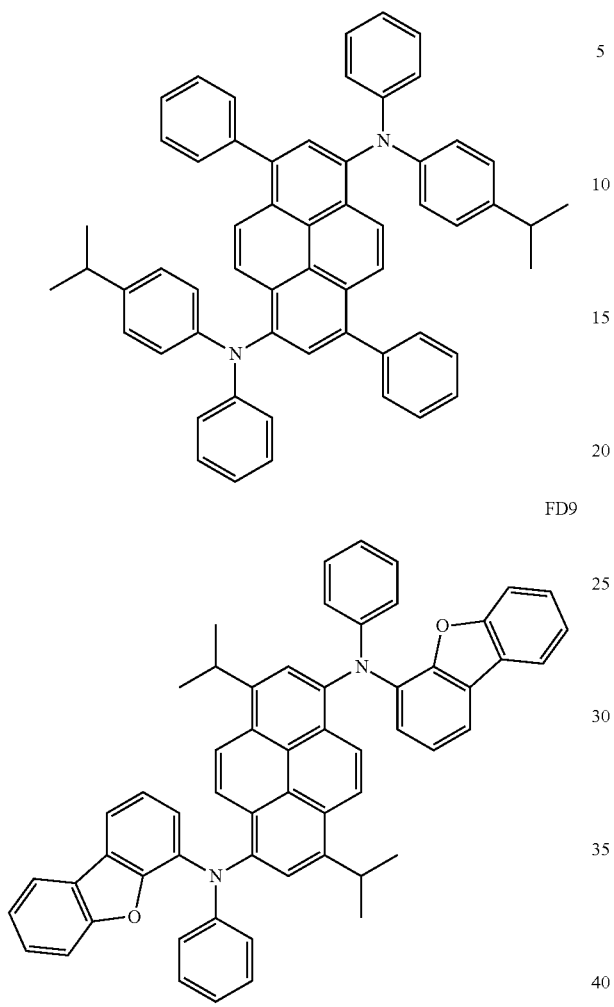
FD9
FD10
FD11
FD12
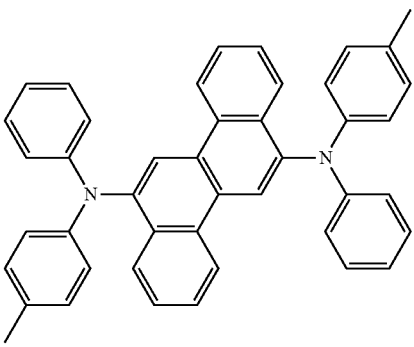
FD13
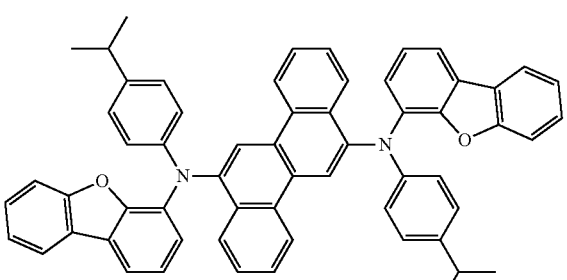
FD14
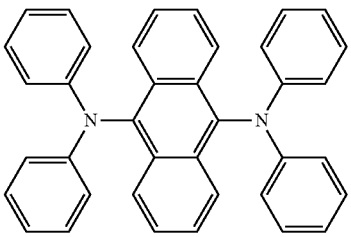
FD15
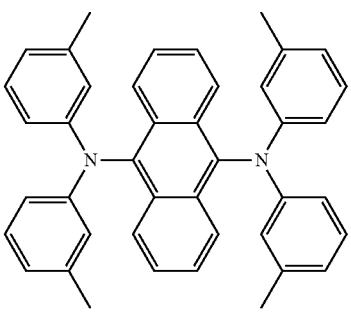
FD16
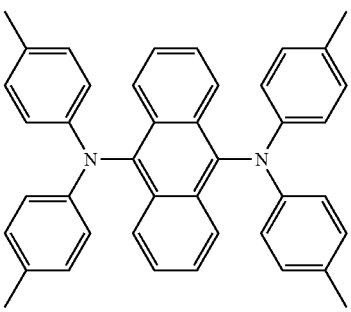

FD17  FD21 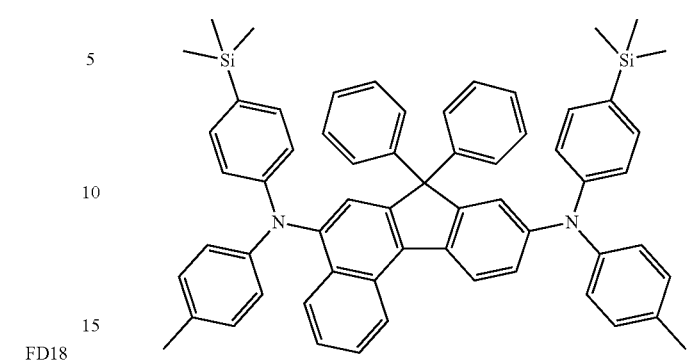
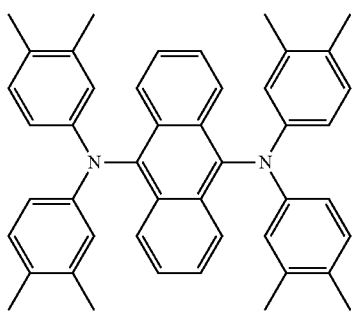
FD18
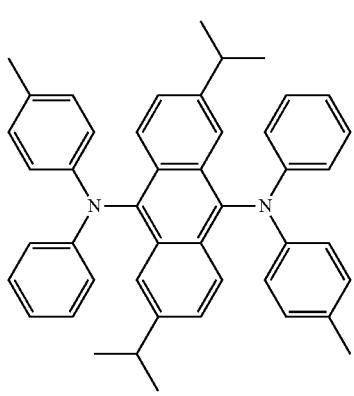
FD22 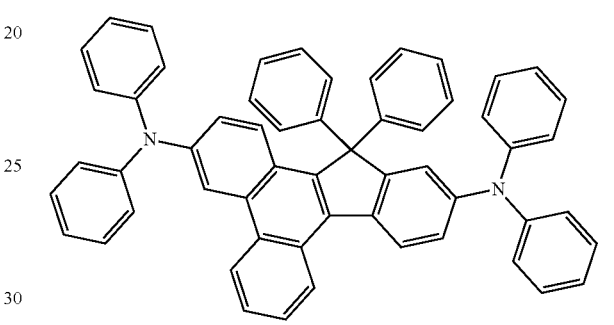
FD19
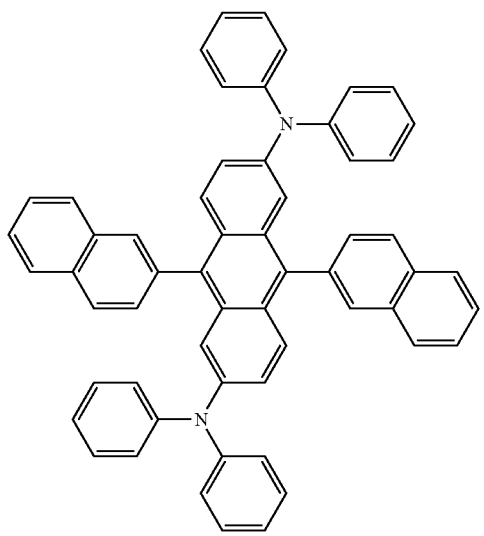
FD23 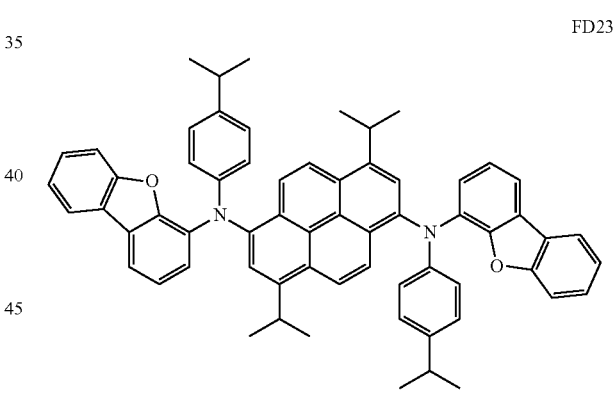
FD20
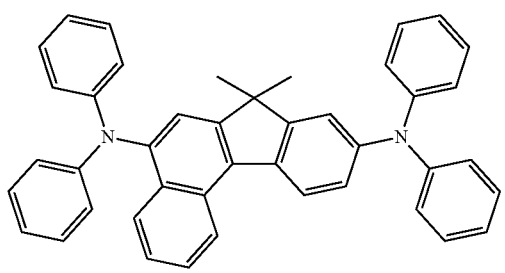
FD24 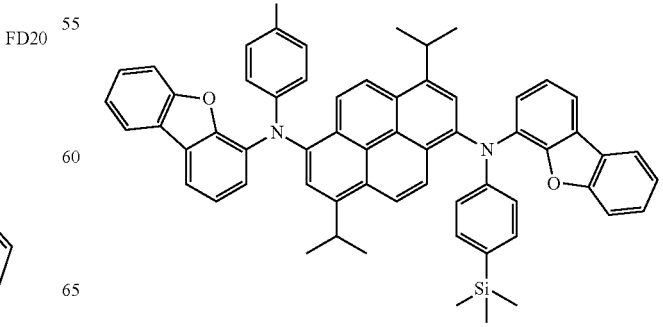

FD25
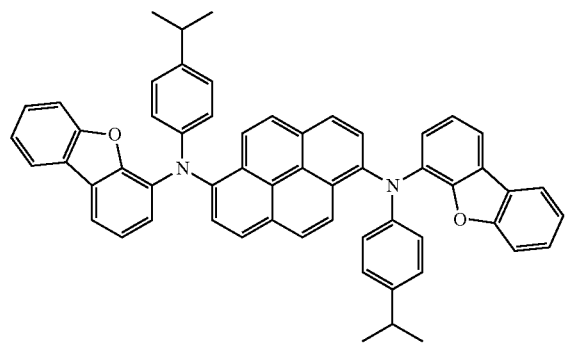
FD29
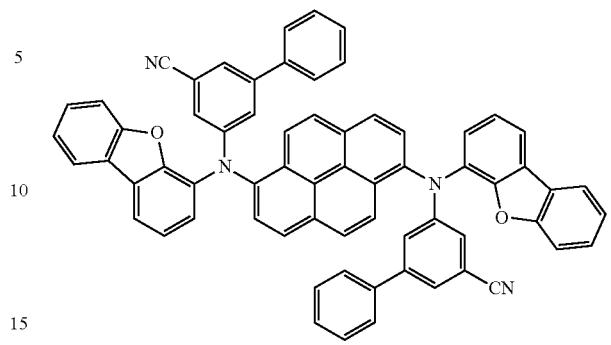
FD26
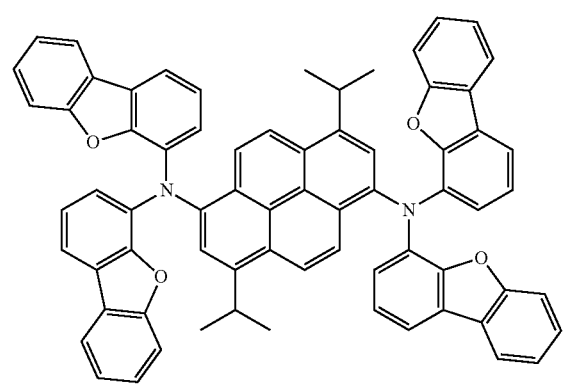
FD30
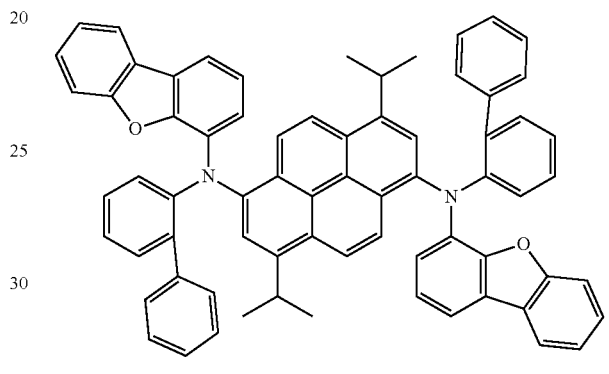
FD27
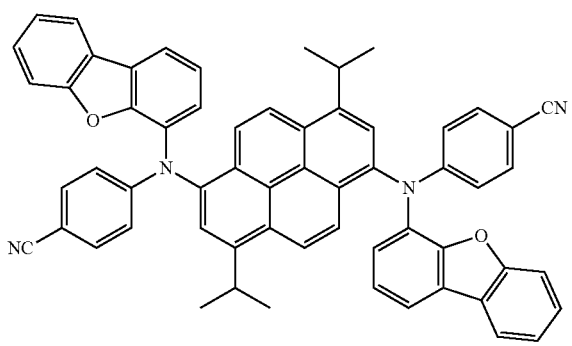
FD31
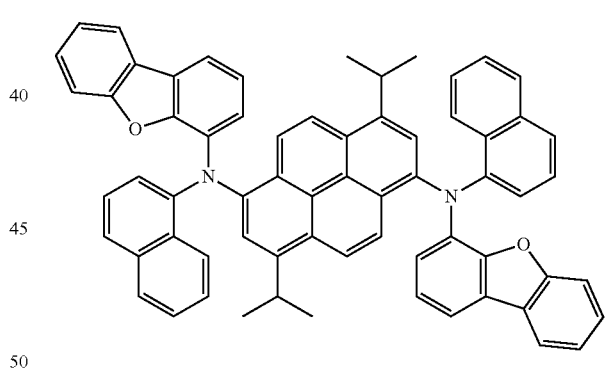
FD28
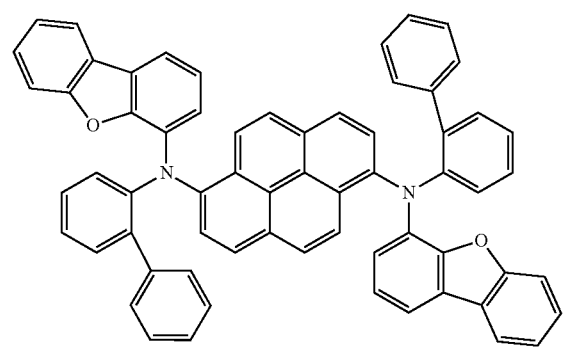
FD32
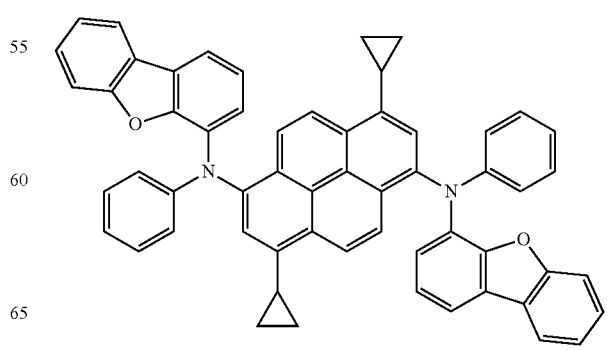

FD33

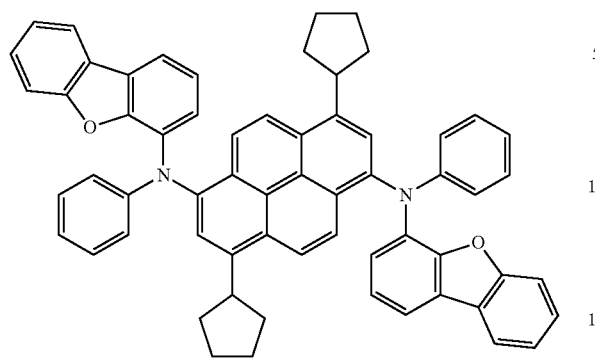

FD34

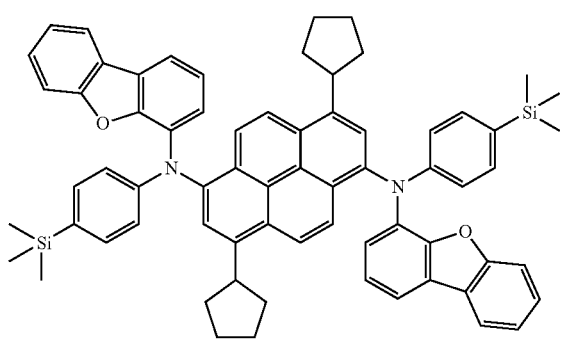

FD35

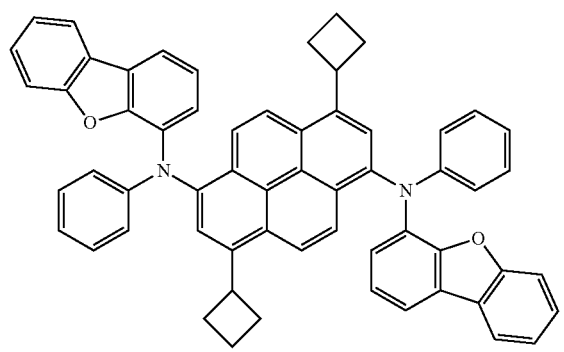

FD36

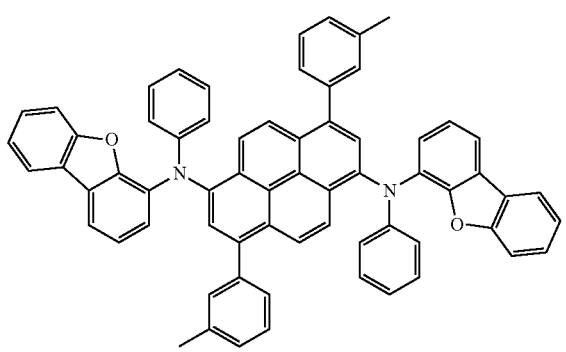

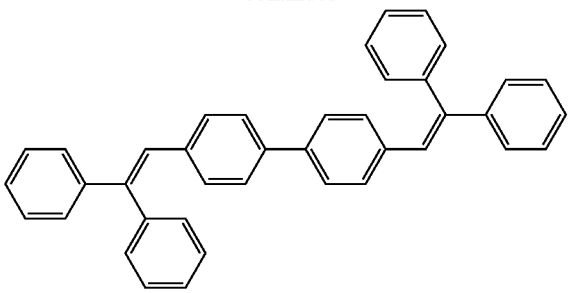

DPVBi

DPAVBi

Delayed Fluorescence Material

The emission layer may include a delayed fluorescence material. The delayed fluorescence material may be selected from compounds capable of emitting delayed fluorescence based on a delayed fluorescence emission mechanism. The delayed fluorescence material included in the emission layer may act as a host or a dopant depending on the type of other materials included in the emission layer.

In an embodiment, a difference between a triplet energy level in the electron volt (eV) of the delayed fluorescence material and a singlet energy level (eV) of the delayed fluorescence material may be greater than or equal to about 0 eV and less than or equal to about 0.5 eV. When the difference between the triplet energy level (eV) of the delayed fluorescence material and the singlet energy level (eV) of the delayed fluorescence material satisfies the above-described range, up-conversion from the triplet state to the singlet state of the delayed fluorescence materials may effectively occur, and thus, the luminescence efficiency of the light-emitting device 10 may be improved.

In an embodiment, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), and ii) a material including a $C_8$-$C_{60}$ polycyclic group in which two or more cyclic groups are condensed while sharing boron (B).

Examples of the delayed fluorescence material may include at least one of Compounds DF1 to DF9:

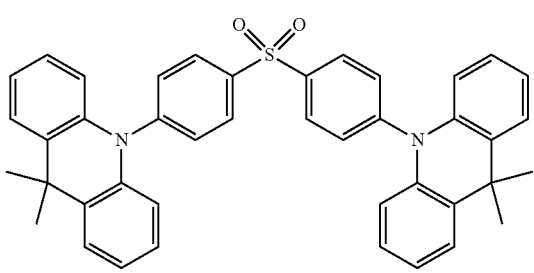
DF1(DMAC-DPS)
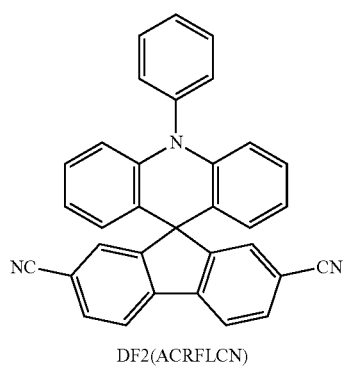
DF2(ACRFLCN)
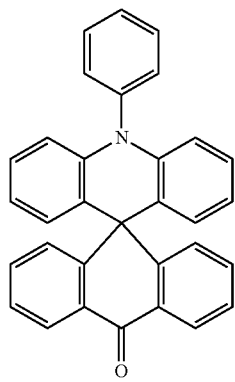
DF3(ACRSA)
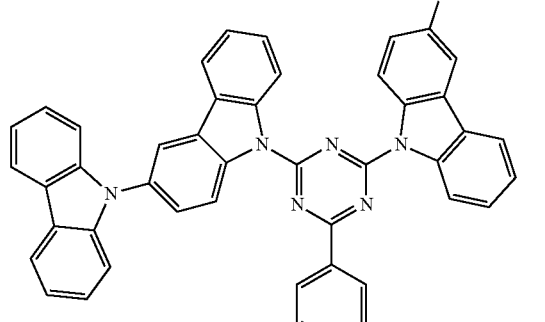
DF4(CC2TA)
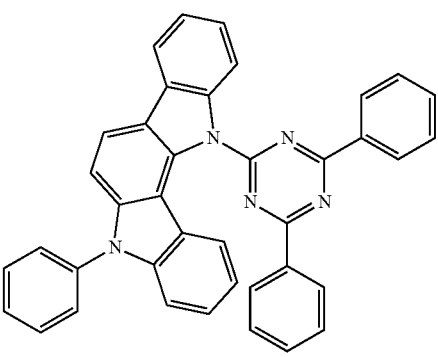
DF5(PIC-TRZ)
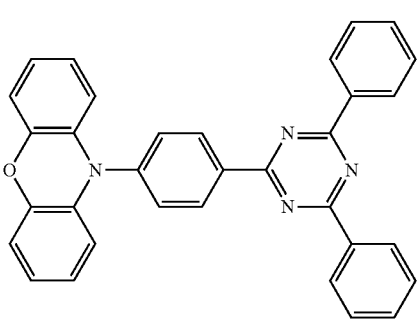
DF6(PIC-TRZ2)
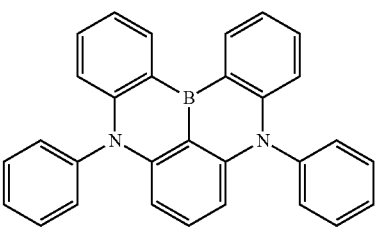
DF7(PXZ-TRZ)
DF8(DABNA-1)

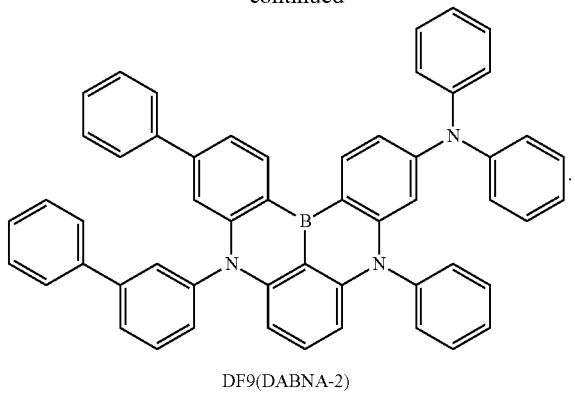

DF9(DABNA-2)

Electron Transport Region in Interlayer 130

The electron transport region may have: i) a single-layered structure consisting of a single layer consisting of a single material, ii) a single-layered structure consisting of a single layer consisting of a plurality of different materials, or iii) a multi-layered structure including a plurality of layers including different materials. The electron transport region may include a hole-blocking layer, an electron control layer, an electron transport layer, an electron injection layer, or any combination thereof.

In an embodiment, the electron transport region may have a hole-blocking layer/electron transport layer/electron injection layer structure, or a hole-blocking layer/electron control layer/electron transport layer/electron injection layer structure, wherein, for each structure, constituting layers are sequentially stacked from an emission layer.

The electron transport region (for example, the hole-blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$[Ar_{601}]_{xe11}$-$[(L_{601})_{xe1}$-$R_{601}]_{xe21}$  Formula 601 wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ are each the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked to each other via a single bond. In one or more embodiments, $Ar_{601}$ in Formula 601 may be a substituted or unsubstituted anthracene group. In one or more embodiments, the electron transport region may include a compound represented by Formula 601-1:

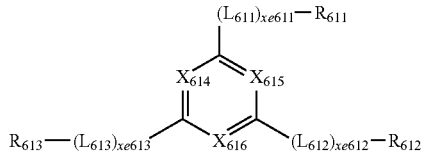

Formula 601-1 wherein, in Formula 601-1, $X_{614}$ may be N or C($R_{614}$), $X_{615}$ may be N or C($R_{615}$), $X_{616}$ may be N or C($R_{616}$), and at least one of $X_{614}$ to $X_{616}$ may be N, $L_{611}$ to $L_{613}$ are each the same as described in connection with $L_{601}$, xe611 to xe613 are each the same as described in connection with xe1, $R_{611}$ to $R_{613}$ are each the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), tris-(8-hydroxyquinoline)aluminum (Alq$_3$), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), 4-(naphthalen-1-yl)-3,5-diphenyl-4H-1,2,4-triazole (NTAZ), 4-(naphthalen-1-yl)-3,5-diphenyl-4H-1,2,4-triazole (T2T), or any combination thereof:

ET1

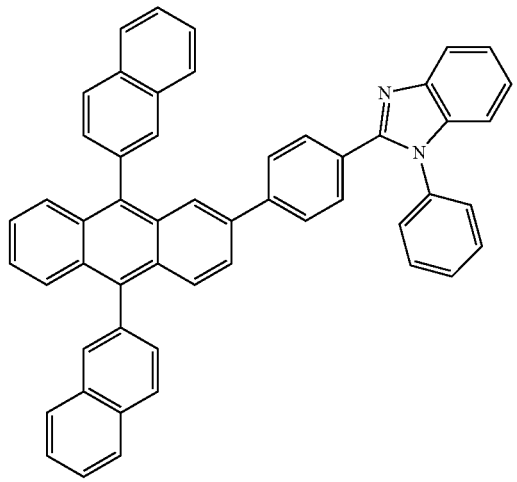

ET2
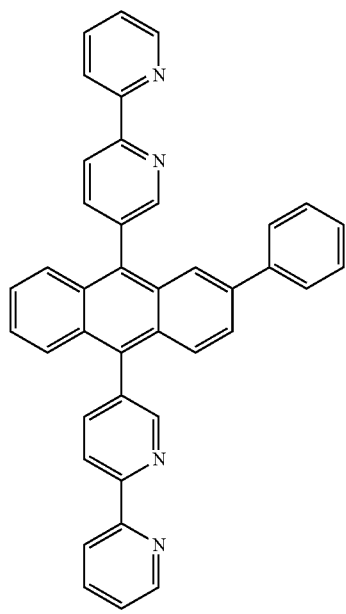
ET3
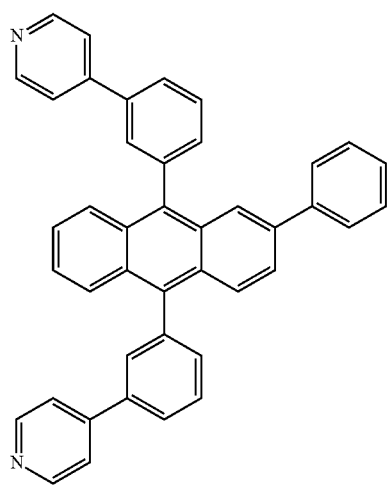
ET4
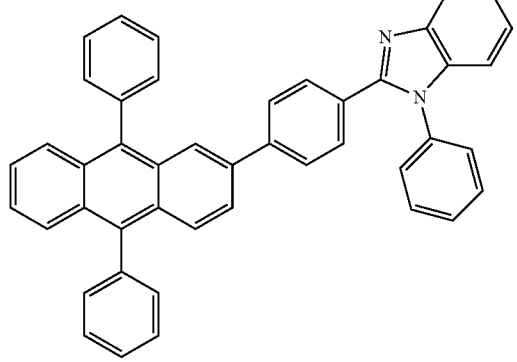
ET5
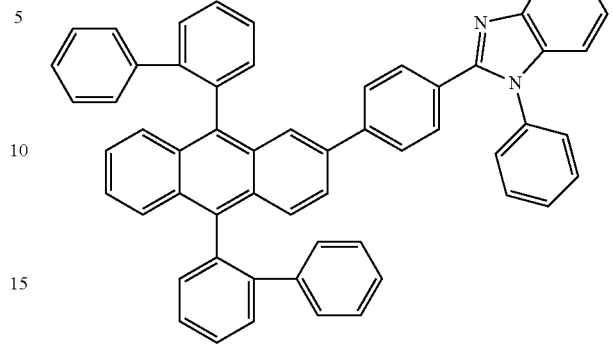
ET6
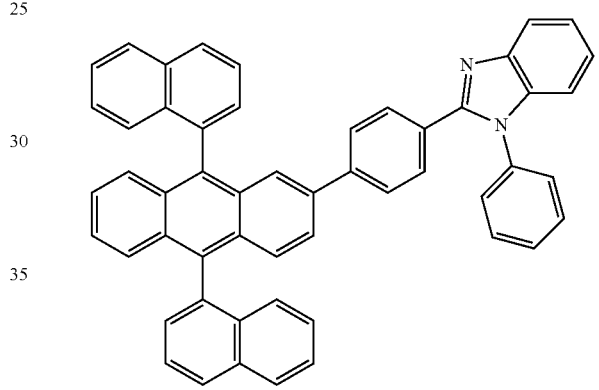
ET7
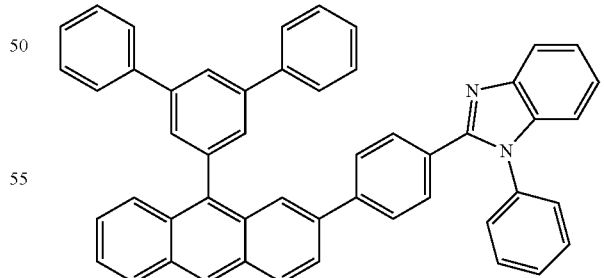

ET8
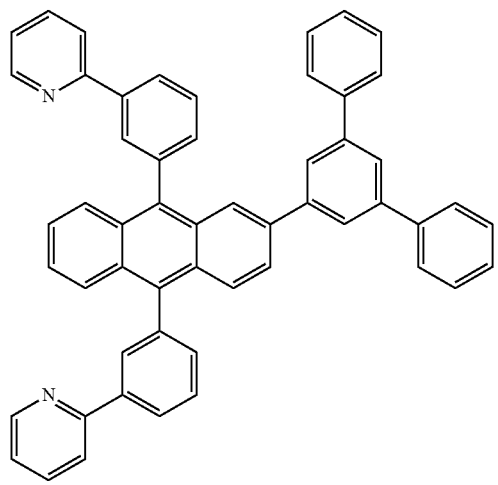
ET10
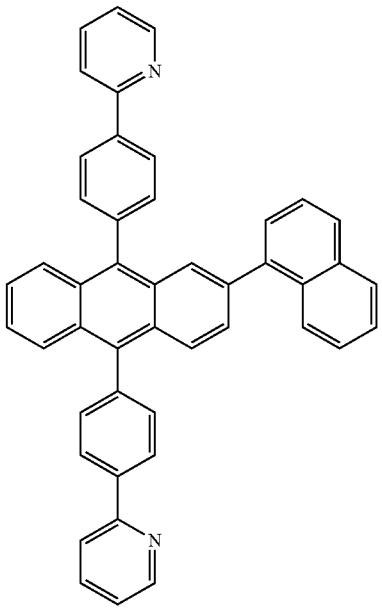
ET11
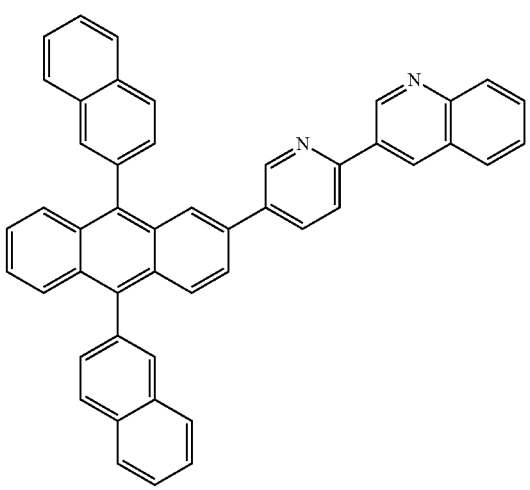
ET9
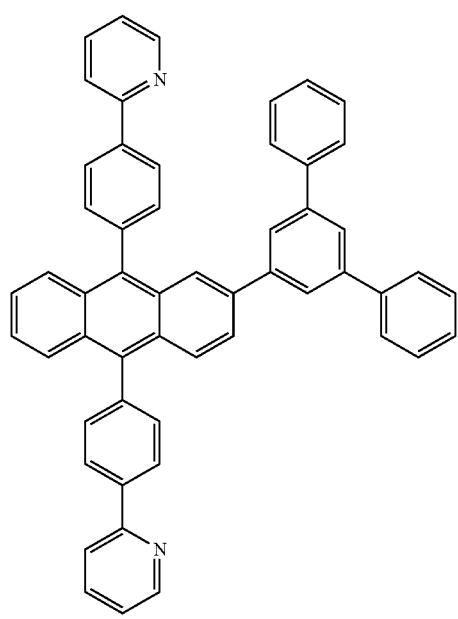
ET12
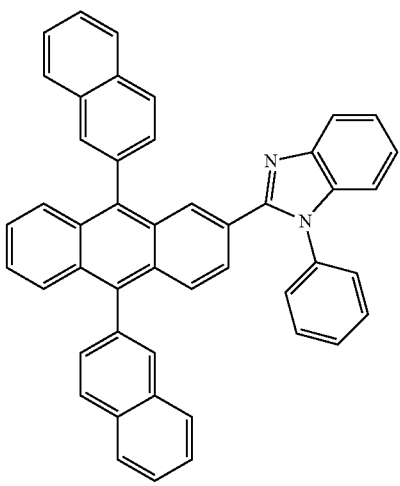

ET13
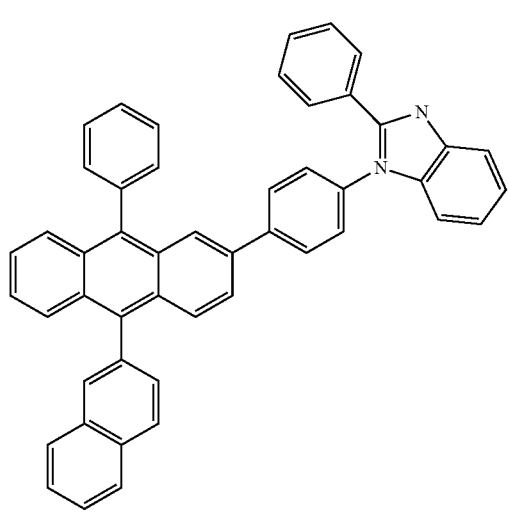
ET14
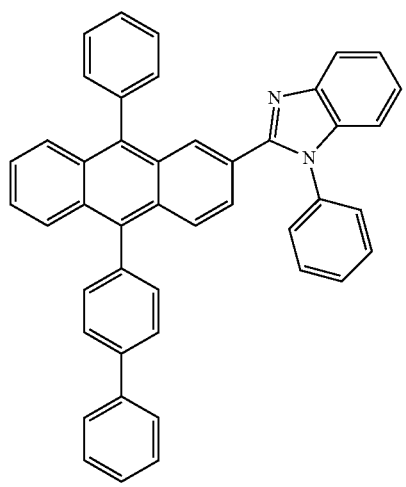
ET15
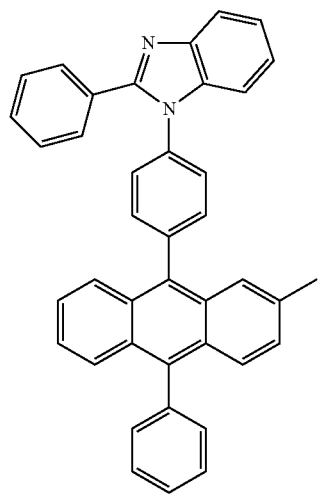
ET16
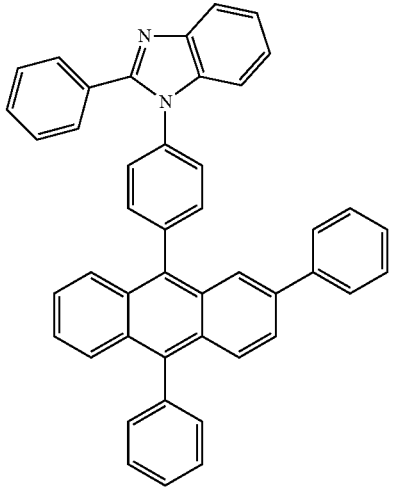
ET17
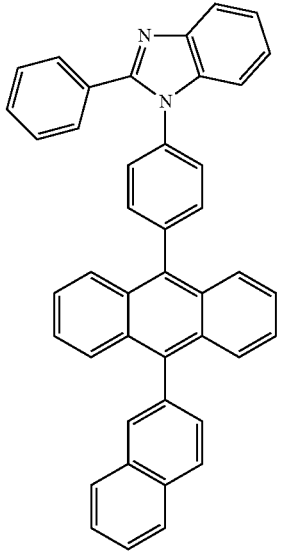
ET18
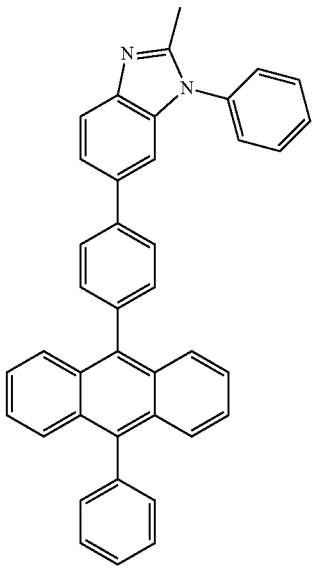

ET19
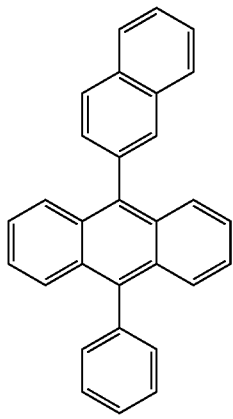
ET20
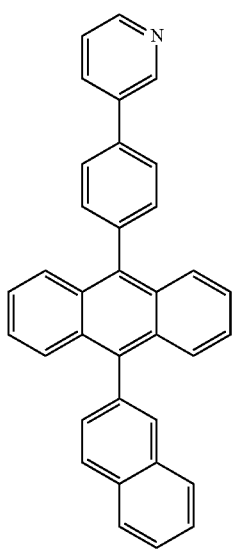
ET21
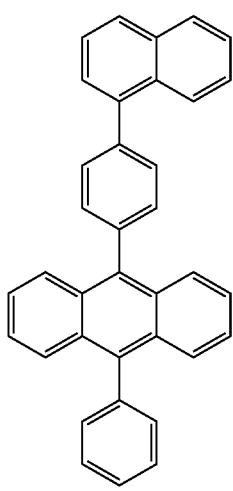
ET22
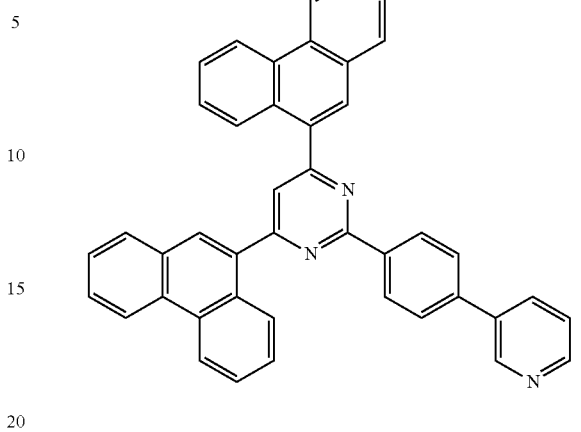
ET23
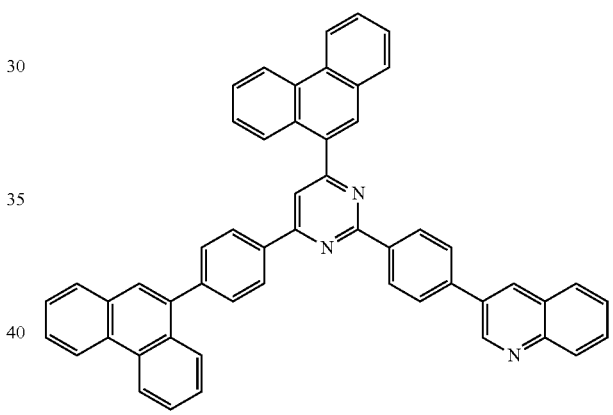
ET24
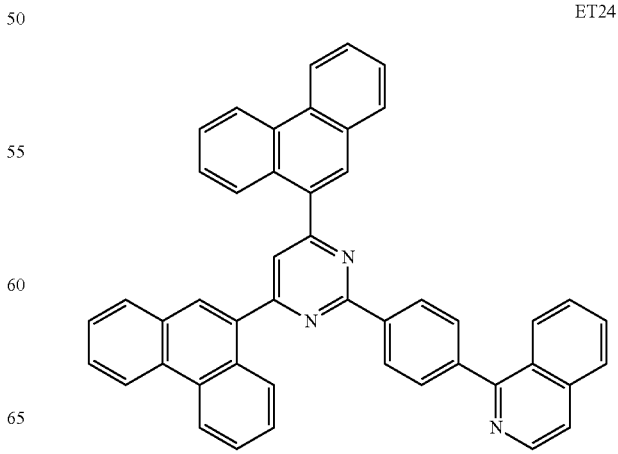

ET25
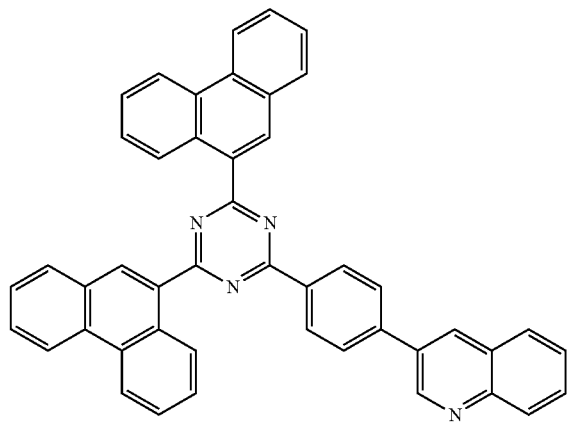
ET26
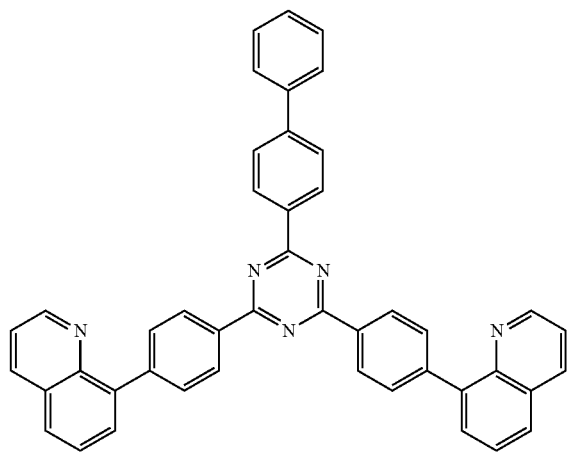
ET27
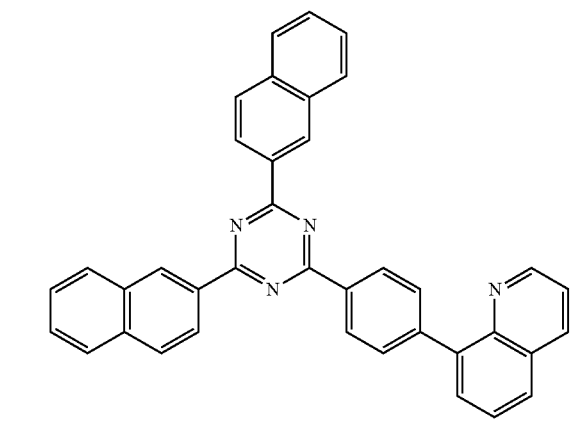
ET28
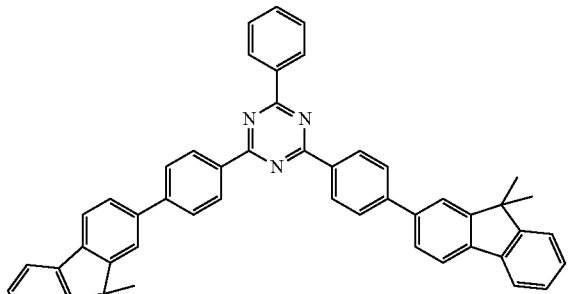
ET29
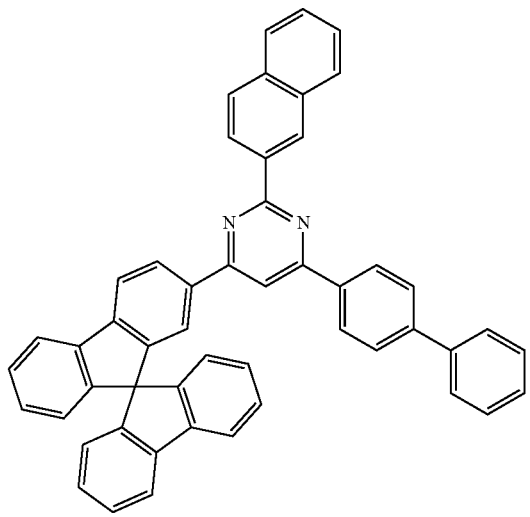
ET30
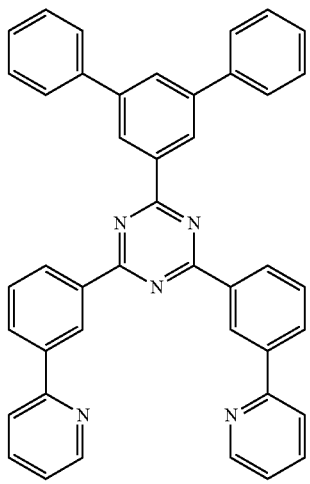

-continued
ET31
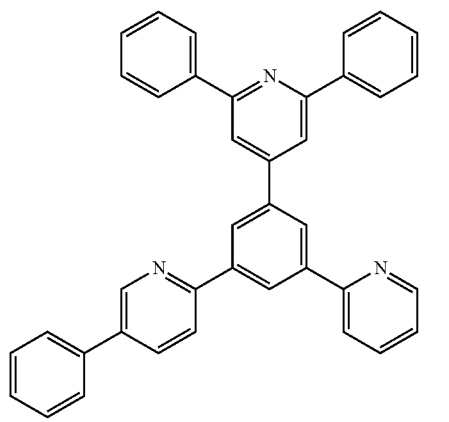
ET32
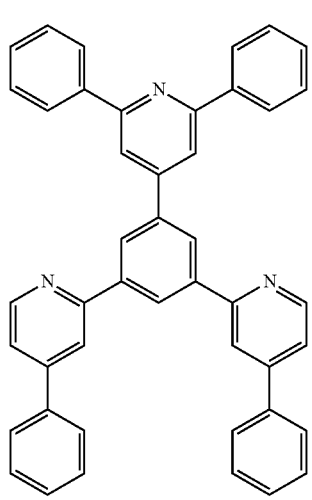
ET33
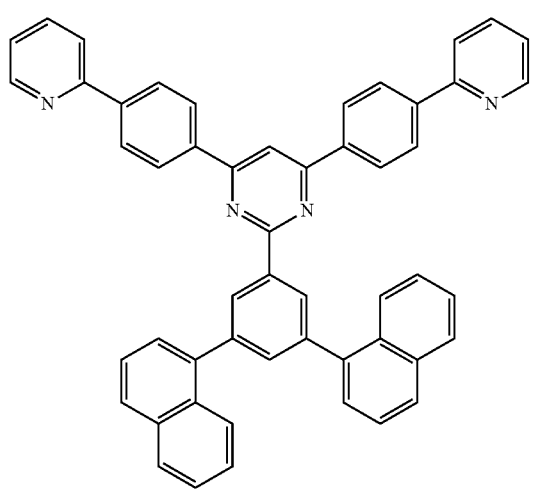
-continued
ET34
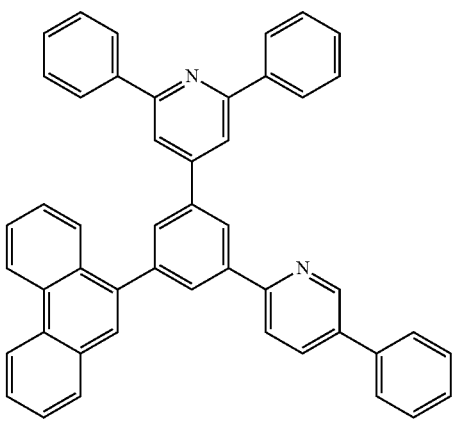
ET35
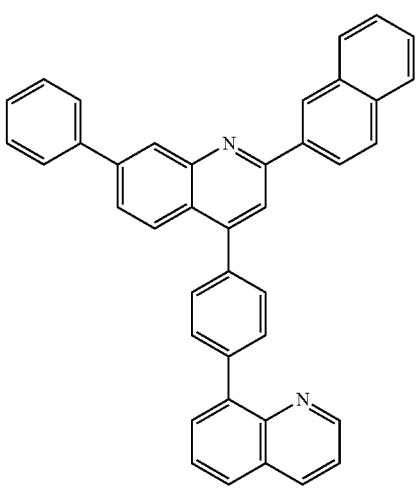
ET36
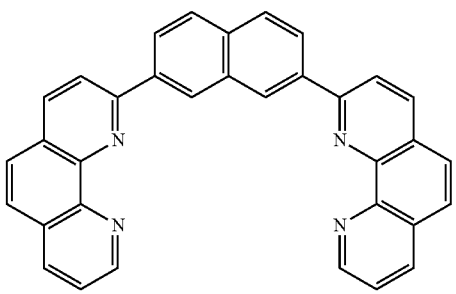
ET37
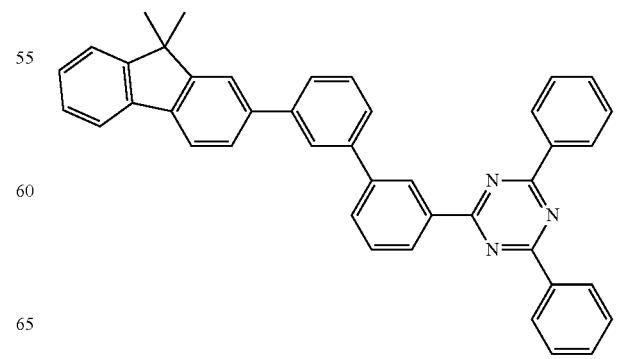

ET38
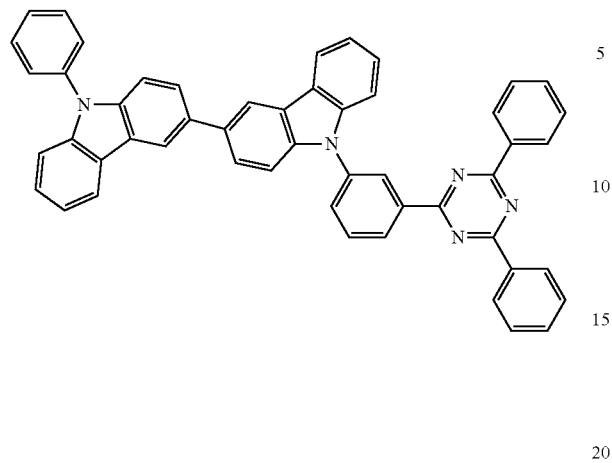
ET41
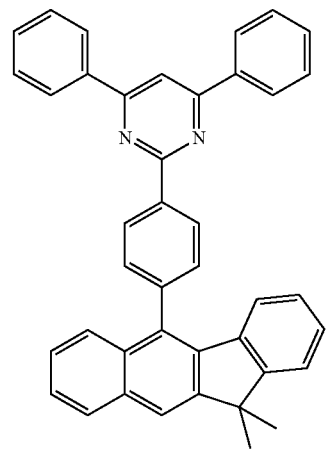
ET39
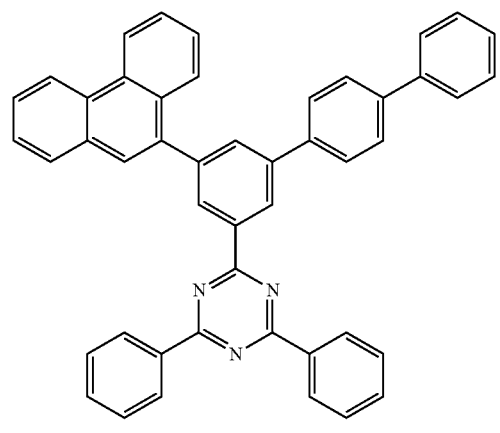
ET42
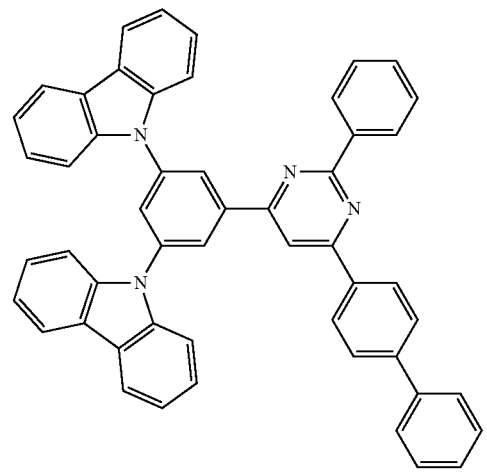
ET40
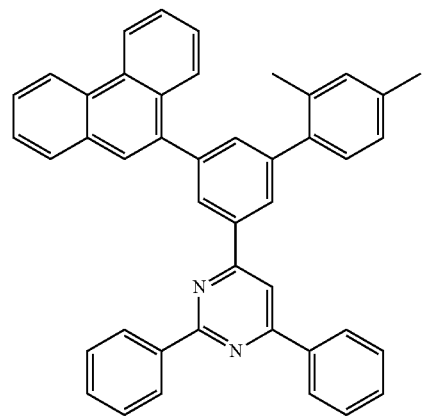
ET43
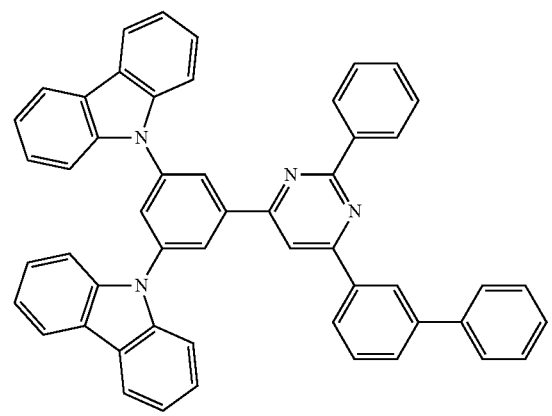

ET44

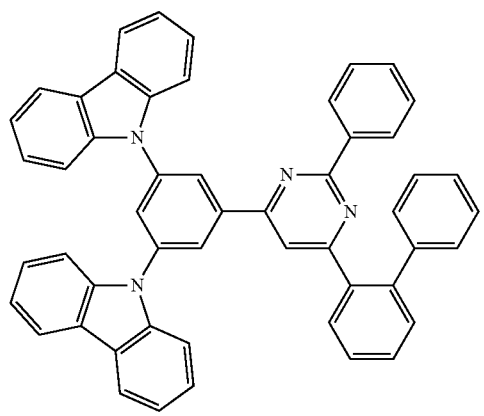

ET45

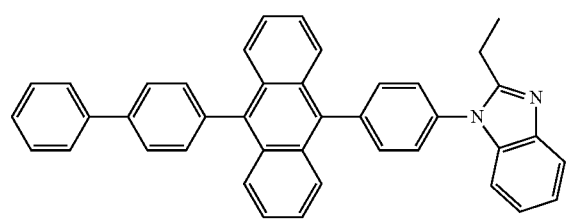

Alq₃

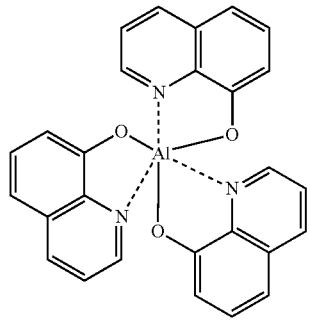

BAlq

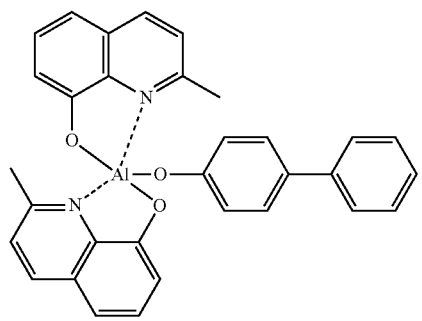

TAZ

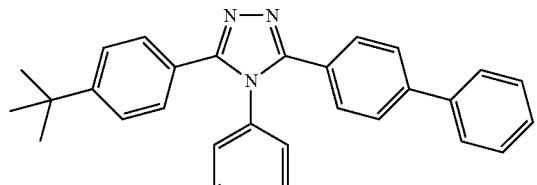

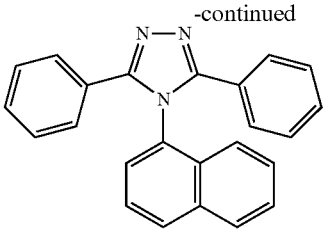

NTAZ

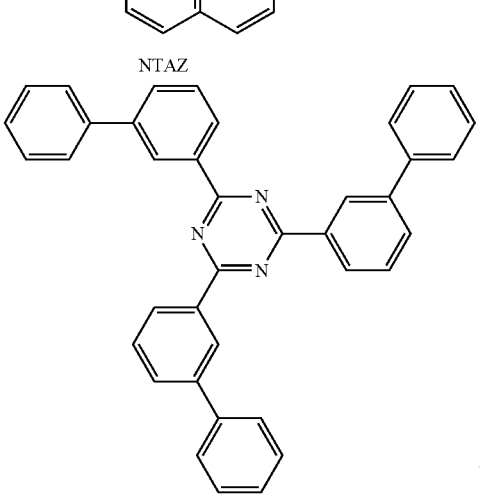

T2T

The thickness of the electron transport region may be from about 160 Å to about 5,000 Å, for example, from about 100 Å to about 4,000 Å. When the electron transport region includes the hole-blocking layer, the electron control layer, the electron transport layer, or any combination thereof, the thickness of the hole-blocking layer or the electron control layer may each independently be from about 20 Å to about 1,000 Å, for example, about 30 Å to about 300 Å, and the thickness of the electron transport layer may be from about 100 Å to about 1,000 Å, for example, about 150 Å to about 500 Å. When the thicknesses of the hole-blocking layer, the electron control layer, the electron transport layer and/or the electron transport layer are within these ranges, satisfactory electron transporting characteristics may be obtained without a substantial increase in driving voltage.

The electron transport region (for example, the electron transport layer in the electron transport region) may further include, in addition to the materials described above, a metal-containing material. The metal-containing material may include an alkali metal complex, an alkaline earth metal complex, or any combination thereof. The metal ion of the alkali metal complex may be a Li ion, a Na ion, a K ion, a Rb ion, or a Cs ion, and the metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

In an embodiment, the metal-containing material may include a Li complex. The Li complex may include, for example, Compound ET-D1 (lithium quinolate, LiQ) or ET-D2:

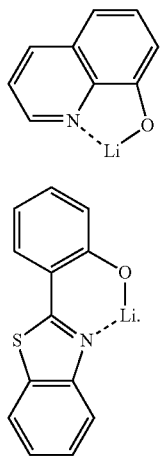

ET-D1

ET-D2

The electron transport region may include an electron injection layer that facilitates the injection of electrons from the second electrode 150. The electron injection layer may directly contact the second electrode 150.

The electron injection layer may have i) a single-layered structure consisting of a single layer consisting of a single material, ii) a single-layered structure consisting of a single layer consisting of a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof. The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include oxides, halides (for example, fluorides, chlorides, bromides, or iodides), or tellurides of the alkali metal, the alkaline earth metal, and the rare earth metal, or any combination thereof.

The alkali metal-containing compound may include alkali metal oxides, such as $Li_2O$, $Cs_2O$, or $K_2O$, alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number satisfying the condition of 0<x<1), $Ba_xCa_{1-x}O$ (x is a real number satisfying the condition of 0<x<1), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenyl benzimidazole, a hydroxyphenylbenzothiazole, a bipyridine, a phenanthroline, a cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In an embodiment, the electron injection layer may consist of i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In an embodiment, the electron injection layer may be a KI:Yb co-deposited layer, an RbI:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

The thickness of the electron injection layer may be in a range of about 1 Å to about 100 Å, and, for example, about 3 Å to about 90 Å. When the thickness of the electron injection layer is within this range, satisfactory electron injection characteristics may be obtained without a substantial increase in driving voltage.

Second Electrode 150

The second electrode 150 may be located on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), an ITO, an IZO, or any combination thereof. The second electrode 150 may be a transmissive electrode, a semi-transmissive electrode, or a reflective electrode. The second electrode 150 may have a single-layered structure or a multi-layered structure including two or more layers.

Capping Layer

A first capping layer may be located outside the first electrode 110, and/or a second capping layer may be located outside the second electrode 150. In detail, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be extracted toward the outside through the first electrode 110, which is a semi-transmissive electrode or a transmissive electrode, and the first capping layer, and light generated in an emission layer of the interlayer 130 of the light-emitting device 10 may be extracted toward the outside through the second electrode 150, which is a semi-transmissive electrode or a transmissive electrode, and the second capping layer.

Although not wanting to bound by theory, the first capping layer and the second capping layer may increase external luminescence efficiency according to the principle of constructive interference. Accordingly, the light extraction efficiency of the light-emitting device 10 is increased, so that the luminescence efficiency of the light-emitting device 10 may be improved.

Each of the first capping layer and second capping layer may include a material having a refractive index (at 589 nm) of about 1.6 or more. The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent containing O, N, S, Se, Si, F, Cl, Br, I, or any combination thereof. In an embodiment, at least one of the first capping layer and the second capping layer may each independently include an amine group-containing compound.

In an embodiment, at least one of the first capping layer and the second capping layer may each independently include a compound represented by Formula 201, a compound represented by Formula 202, or any combination thereof.

In one or more embodiments, at least one of the first capping layer and the second capping layer may each independently include one of Compounds HT28 to HT33, one of Compounds CP1 to CP6, N4,N4'-di(naphthalen-2-yl)-N4,N4'-diphenyl-[1,1'-biphenyl]-4,4'-diamine (β-NPB), or any combination thereof:

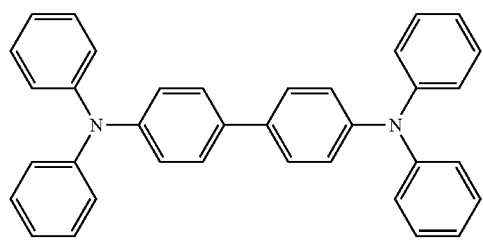

CP1

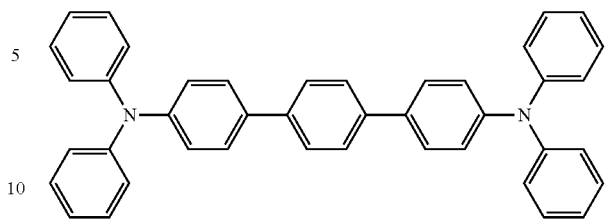

CP2

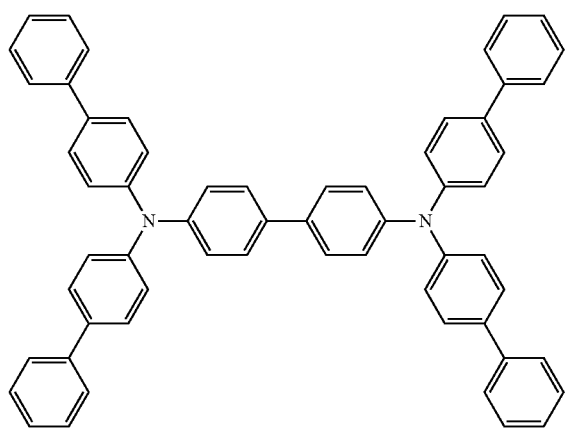

CP3

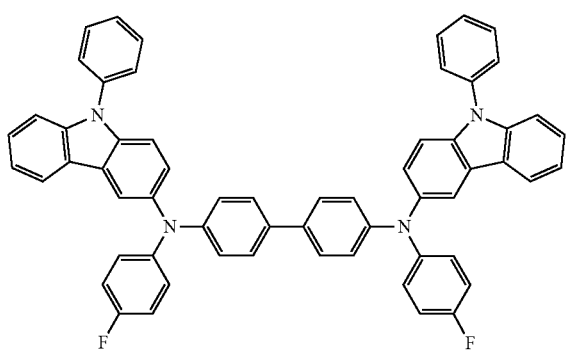

CP4

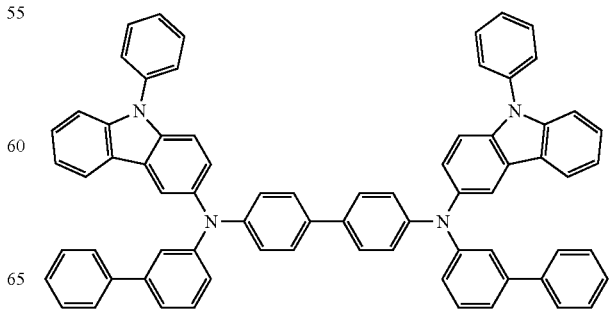

CP5

-continued

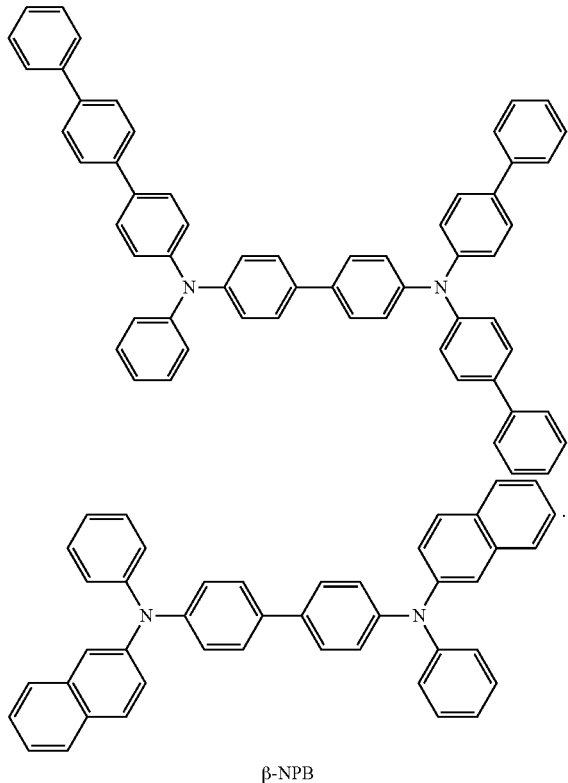

β-NPB

Electronic Apparatus

The light-emitting device 10 may be included in various electronic apparatuses. In an embodiment, the electronic apparatus including the light-emitting device 10 may be a light-emitting apparatus, an authentication apparatus, or the like.

The electronic apparatus (for example, light-emitting apparatus) may further include, in addition to the light-emitting device 10, i) a color filter, ii) a color conversion layer, or iii) a color filter and a color conversion layer. The color filter and/or the color conversion layer may be located in at least one traveling direction of light emitted from the light-emitting device 10. In an embodiment, the light emitted from the light-emitting device 10 may be blue light or white light. The light-emitting device 10 may be the same as described above. In an embodiment, the color conversion layer may include quantum dots. The quantum dot may be, for example, a quantum dot as described herein.

The electronic apparatus may include a first substrate. The first substrate may include a plurality of subpixel areas, the color filter may include a plurality of color filter areas respectively corresponding to the plurality of subpixel areas, and the color conversion layer may include a plurality of color conversion areas respectively corresponding to the plurality of subpixel areas.

A pixel-defining film may be located among the plurality of subpixel areas to define each of the subpixel areas. The color filter may further include a plurality of color filter areas and light-shielding patterns located among the plurality of color filter areas, and the color conversion layer may include a plurality of color conversion areas and light-shielding patterns located among the plurality of color conversion areas.

The plurality of color filter areas (or the plurality of color conversion areas) may include a first area emitting first-color light, a second area emitting second-color light, and/or a third area emitting third-color light, and the first-color light, the second-color light, and/or the third-color light may have different maximum emission wavelengths from one another. In an embodiment, the first-color light may be red light, the second-color light may be green light, and the third-color light may be blue light. In an embodiment, the plurality of color filter areas (or the plurality of color conversion areas) may include quantum dots. In detail, the first area may include a red quantum dot, the second area may include a green quantum dot, and the third area may not include a quantum dot. The quantum dot is the same as described herein. Each of the first area, the second area, and/or the third area may further include a scatterer.

In an embodiment, the light-emitting device 10 may emit a first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths from one another. In detail, the first light may be blue light, the first first-color light may be red light, the second first-color light may be green light, and the third first-color light may be blue light.

The electronic apparatus may further include a thin-film transistor in addition to the light-emitting device 10 as described above. The thin-film transistor may include a source electrode, a drain electrode, and an activation layer, wherein any one of the source electrode and the drain electrode may be electrically connected to any one of the first electrode and the second electrode of the light-emitting device 10.

The thin-film transistor may further include a gate electrode, a gate insulating film, or the like. The activation layer may include a crystalline silicon, an amorphous silicon, an organic semiconductor, an oxide semiconductor, or the like.

The electronic apparatus may further include a sealing portion for sealing the light-emitting device 10. The sealing portion and/or the color conversion layer may be located between the color filter and the light-emitting device 10. The sealing portion allows light from the light-emitting device 10 to be extracted to the outside, while simultaneously preventing ambient air and moisture from penetrating into the light-emitting device 10. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various functional layers may be additionally located on the sealing portion, in addition to the color filter and/or the color conversion layer, according to the use of the electronic apparatus. Examples of the functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.). The authentication apparatus may further include, in addition to the light-emitting device 10, a biometric information collector.

The electronic apparatus may take the form of or be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
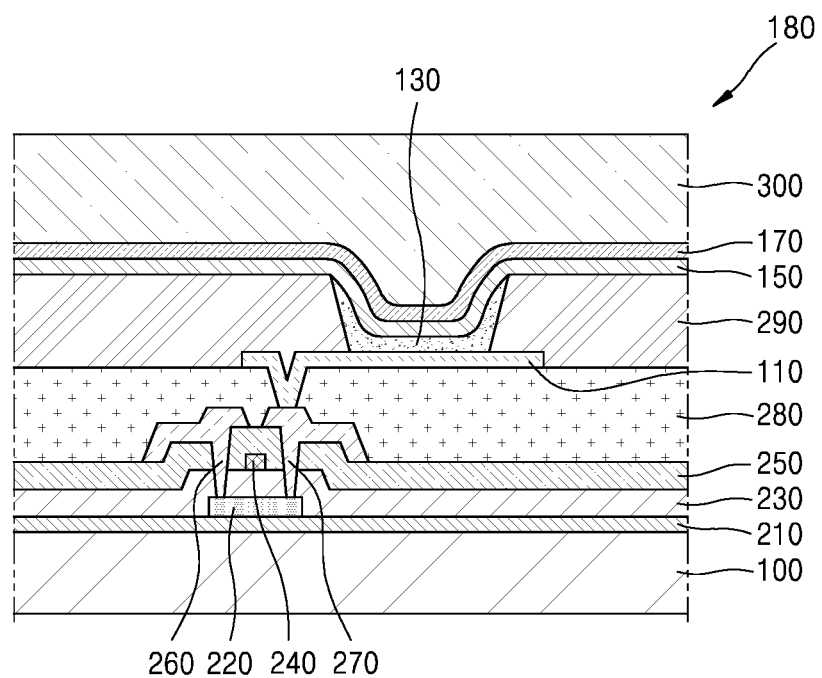
FIG. 2 is a schematic cross-sectional view of an embodiment of a light-emitting apparatus including a light-emitting device constructed according to the principles of the invention.
Figure 3:
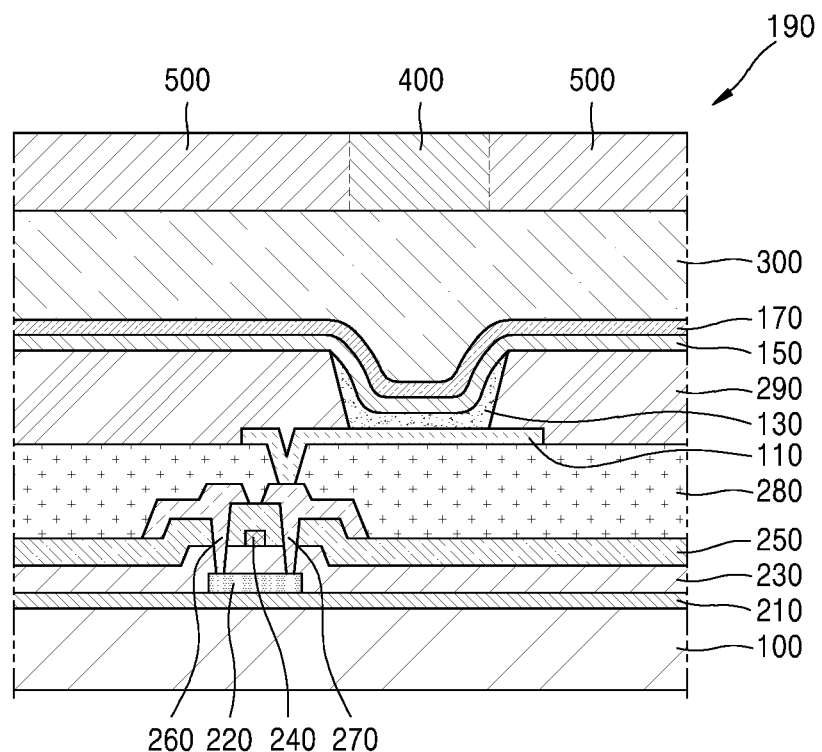
FIG. 3 is a schematic cross-sectional view of another embodiment of a light-emitting apparatus including a light-emitting device constructed according to the principles of the invention.

Description of FIGS. 2 and 3

FIG. 2 is a schematic cross-sectional view of an embodiment of a light-emitting apparatus including a light-emitting device constructed according to the principles of the invention.

The light-emitting apparatus 180 of FIG. 2 includes a substrate 100, a thin-film transistor (TFT) 200, a light-emitting device, and an encapsulation portion 300 that seals the light-emitting device 10.

The substrate 100 may be a flexible substrate, a glass substrate, or a metal substrate. A buffer layer 210 may be located on the substrate 100. The buffer layer 210 may prevent penetration of impurities through the substrate 100 and may provide a substantially flat surface on the substrate 100.

The TFT 200 may be located on the buffer layer 210. The TFT 200 may include an activation layer 220, a gate electrode 240, a source electrode 260, and a drain electrode 270. The activation layer 220 may include an inorganic semiconductor such as a silicon or a polysilicon, an organic semiconductor, or an oxide semiconductor, and may include a source region, a drain region and a channel region. A gate insulating film 230 for insulating the activation layer 220 from the gate electrode 240 may be located on the activation layer 220, and the gate electrode 240 may be located on the gate insulating film 230.

An interlayer insulating film 250 may be located on the gate electrode 240. The interlayer insulating film 250 may be located between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT 200 is electrically connected to a light-emitting device 10 to drive the light-emitting device 10, and is covered by a passivation layer 280. The passivation layer 280 may include an inorganic insulating film, an organic insulating film, or any combination thereof. The light-emitting device 10 is provided on the passivation layer 280. The light-emitting device 10 may include a first electrode 110, an interlayer 130, and a second electrode 150.

The first electrode 110 may be located on the passivation layer 280. The passivation layer 280 may not completely cover the drain electrode 270 and may expose a portion of the drain electrode 270, and the first electrode 110 may be connected to the exposed portion of the drain electrode 270.

A pixel defining layer 290 containing an insulating material may be located on the first electrode 110. The pixel defining layer 290 may expose a portion of the first electrode 110, and the interlayer 130 may be formed in the exposed portion of the first electrode 110. The pixel defining layer 290 may be a polyimide or polyacrylic organic film. At least some layers of the interlayer 130 may extend beyond the upper portion of the pixel defining layer 290 to be located in the form of a common layer. The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device 10 to protect the light-emitting device from moisture or oxygen. The encapsulation portion 300 may include: an inorganic film including a silicon nitride ($SiN_x$), a silicon oxide ($SiO_x$), an indium tin oxide, an indium zinc oxide, or any combination thereof; an organic film including a polyethylene terephthalate, a polyethylene naphthalate, a polycarbonate, a polyimide, a polyethylene sulfonate, a polyoxymethylene, a polyarylate, a hexamethyldisiloxane, an acrylic resin (for example, a polymethyl methacrylate, a polyacrylic acid, or the like), an epoxy-based resin (for example, an aliphatic glycidyl ether (AGE), or the like), or any combination thereof; or any combination of the inorganic film and the organic film.

FIG. 3 is a schematic cross-sectional view of another embodiment of a light-emitting apparatus including a light-emitting device constructed according to the principles of the invention.

The light-emitting apparatus 190 of FIG. 3 is the same as the light-emitting apparatus 180 of FIG. 2, except that a light-shielding pattern 500 and a functional region 400 are additionally located on the encapsulation portion 300. The functional region 400 may be a combination of i) a color filter area, ii) a color conversion area, or iii) a combination of the color filter area and the color conversion area. In an embodiment, the light-emitting device 10 included in the light-emitting apparatus 190 of FIG. 3 may be a tandem light-emitting device.

Manufacture Method

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When respective layers included in the hole transport region, the emission layer, and respective layers included in the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

DEFINITION OF TERMS

The term "an interlayer" as used herein refers to a single layer and/or a plurality of layers located between the first electrode and the second electrode of an organic light-emitting device. A material included in the "interlayer" is not limited to an organic material.

The term "first host" may be abbreviated "H1," the term "second host" may be abbreviated "H2," the term "dopant" may be abbreviated "D," the term "lowest unoccupied molecular orbital" may be abbreviated "LUMO," the term "highest occupied molecular orbital" may be abbreviated "HOMO," and the term "$T_1$ energy" of the dopant or host may be abbreviated "$T_1$ energy". The full phrase may be used interchangeably with the abbreviation or vice-versa throughout the specification, including the claims, for the sake of understanding and brevity. Moreover, a plurality of first hosts or second hosts may be abbreviated, respectively, "H1 s" and "H2s".

As used herein, the term "atom" may mean an element or its corresponding radical bonded to one or more other atoms.

The terms "hydrogen" and "deuterium" refer to their respective atoms and corresponding radicals with the deuterium radical abbreviated "-D", and the terms "—F, —Cl, —Br, and —I" are radicals of, respectively, fluorine, chlorine, bromine, and iodine.

As used herein, a substituent for a monovalent group, e.g., alkyl, may also be, independently, a substituent for a corresponding divalent group, e.g., alkylene.

The term "$C_3$-$C_{60}$ carbocyclic group" as used herein refers to a cyclic group consisting of carbon only as a ring-forming atom and having 3 to 60 carbon atoms, and the term "$C_1$-$C_{60}$ heterocyclic group" as used herein refers to a cyclic group that has 1 to 60 carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are fused with each other. In an embodiment, the $C_1$-$C_{60}$ heterocyclic group may have 3 to 61 ring-forming atoms.

The "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has 3 to 60 carbon atoms and does not include *—N=*' as a ring-forming moiety, and the term "π electron-deficient nitrogen-containing $C_1$-$C_{60}$ cyclic group" as used herein refers to a heterocyclic group that has 1 to 60 carbon atoms and includes *—N=*' as a ring-forming moiety.

In an embodiment, the $C_3$-$C_{60}$ carbocyclic group may be i) a group T1G or ii) a fused cyclic group in which two or more groups TIG are fused with each other, for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group.

The $C_1$-$C_{60}$ heterocyclic group may be i) a group T2G, ii) a fused cyclic group in which two or more groups T2G are fused with each other, or iii) a fused cyclic group in which at least one group T2G and at least one group T1G are fused with each other, for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The π electron-rich $C_3$-$C_{60}$ cyclic group may be i) a group T1G, ii) a fused cyclic group in which two or more groups T1G are fused with each other, iii) a group T3G, iv) a fused cyclic group in which two or more groups T3G are fused with each other, or v) a fused cyclic group in which at least one group T3G and at least one group T1G are fused with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.

The π electron-deficient nitrogen-containing $C_1$-$C_{60}$ cyclic group may be i) a group T4G, ii) a fused cyclic group in which two or more groups T4G are fused with each other, iii) a fused cyclic group in which at least one group T4G and at least one group T1G are fused with each other, iv) a fused cyclic group in which at least one group T4G and at least one group T3G are fused with each other, or v) a fused cyclic group in which at least one group T4G, at least one group T1G, and at least one group T3G are fused with one another, for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The group T1G may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group.

The group T2G may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group.

The group T3G may be a furan group, a thiophene group, a 1H-pyrrole group, a silole group, or a borole group.

The group T4G may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{60}$ heterocyclic group, the π electron-rich $C_3$-$C_{60}$ cyclic group, or the π electron-deficient nitrogen-containing $C_1$-$C_{60}$ cyclic group" as used herein refer to a group fused to any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic fused polycyclic group, and a monovalent non-aromatic fused heteropolycyclic group, and examples of the divalent $C_3$-$C_{60}$ carbocyclic group and the monovalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic fused polycyclic group, and a substituted or unsubstituted divalent non-aromatic fused heteropolycyclic group.

The term "$C_1$-$C_{60}$ alkyl group" as used herein refers to a linear or branched aliphatic hydrocarbon monovalent group that has 1 to 60 carbon atoms, and examples thereof include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having a structure corresponding to the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having a structure corresponding to the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom as a ring-forming atom and has 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to the $C_1$-$C_{10}$ heterocycloalkyl group.

The term "$C_3$-$C_{10}$ cycloalkenyl group" as used herein refers to a monovalent cyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom as a ring-forming atom, 1 to 10 carbon atoms, and at least one double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having a structure corresponding to the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be fused with each other.

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be fused with each other.

The term "monovalent non-aromatic fused polycyclic group" as used herein refers to a monovalent group (for example, having 8 to 60 carbon atoms) having two or more rings fused to each other, only carbon atoms as ring-forming atoms, and no aromaticity in its entire molecular structure. Examples of the monovalent non-aromatic fused polycyclic group include an indenyl group, a fluorenyl group, a spirobifluorenyl group, a benzofluorenyl group, an indenophenanthrenyl group, and an indeno anthracenyl group. The term "divalent non-aromatic fused polycyclic group" as used herein refers to a divalent group having a structure corresponding to a monovalent non-aromatic fused polycyclic group.

The term "monovalent non-aromatic fused heteropolycyclic group" as used herein refers to a monovalent group (for example, having 1 to 60 carbon atoms) having two or more rings fused to each other, at least one heteroatom other than carbon atoms, as a ring-forming atom, and non-aromaticity in its entire molecular structure. Examples of the monovalent non-aromatic fused heteropolycyclic group include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indeno carbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphtho silolyl group, a benzofurodibenzofuranyl group, a benzofurodibenzothiophenyl group, and a benzothienodibenzothiophenyl group. The term "divalent non-aromatic heterofused polycyclic group" as used herein refers to a divalent group having a structure corresponding to a monovalent non-aromatic heterofused polycyclic group.

The term "$C_6$-$C_{60}$ aryloxy group" as used herein indicates —O$A_{102}$ (wherein $A_{102}$ is the $C_6$-$C_{60}$ aryl group), and the term "$C_6$-$C_{60}$ arylthio group" as used herein indicates —S$A_{103}$ (wherein $A_{103}$ is the $C_6$-$C_{60}$ aryl group).

The term "$C_7$-$C_{60}$ aryl alkyl group" used herein refers to -$A_{104}A_{105}$ (where $A_{104}$ may be a $C_1$-$C_{54}$ alkylene group, and $A_{105}$ may be a $C_6$-$C_{59}$ aryl group), and the term $C_2$-$C_{60}$ heteroaryl alkyl group" used herein refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:
  deuterium (-D), —F, —Cl, —Br, —I, a hydroxyl group, a cyano group, or a nitro group;
  a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;
  a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or
  —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

The variables $Q_1$ to $Q_3$, $Q_{11}$ to $Q_{13}$, $Q_{21}$ to $Q_{23}$, and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom include O, S, N, P, Si, B, Ge, Se, or any combination thereof The term "the third-row transition metal" used herein includes hafnium (Hf), tantalum (Ta), tungsten (W), rhenium (Re), osmium (Os), iridium (Ir), platinum (Pt), or gold (Au).

As used herein, the term "Ph" refers to a phenyl group, the term "Me" refers to a methyl group, the term "Et" refers to an ethyl group, the term "ter-Bu" or $Bu^t$ refers to a tert-butyl group, and the term "OMe" refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

The number of carbon atoms in this substituent definition section is an example only. In an embodiment, the maximum carbon number of 60 in the $C_1$-$C_{60}$ alkyl group is an example, and the definition of the alkyl group is equally applied to a $C_1$-$C_{20}$ alkyl group. In an embodiment, the minimum carbon number of 12 in the $C_{12}$-$C_{60}$ heteroaryl group is an example, and the definition of the heteroaryl group is equally applied. Other cases are the same.

The symbols * and *' as used herein, unless defined otherwise, each refer to a binding site to a neighboring atom in a corresponding formula or moiety.

Hereinafter, a compound made according to the principles and embodiments of the invention and a light-emitting device including the same will be described in detail with reference to Synthesis Examples and Examples. The wording "B was used instead of A" used in describing Synthesis Examples refers to that an identical molar equivalent of B was used in place of A.

EXAMPLES

Example 1

As an anode, a glass substrate (product of Corning Inc. of Corning, N.Y.) with 15 Ω/cm² (1,200 Å) ITO formed thereon was cut to a size of 50 mm×50 mm×0.7 mm, sonicated with isopropyl alcohol and pure water each for 5 minutes, and then cleaned by exposure to ultraviolet rays and ozone for 30 minutes. Then, the resultant structure was mounted on a vacuum deposition apparatus.

2-TNATA was vacuum-deposited on the anode to form a hole injection layer having a thickness of 600 Å, and 4,4'-bis[N-(1-naphthyl)-N-phenylamino]biphenyl (hereinafter referred to as NPB) was vacuum-deposited on the hole injection layer to form a hole transport layer having a thickness of 300 Å. m-MTDATA was vacuum-deposited on the hole transport layer to form an electron-blocking layer having a thickness of 100 Å.

Compound PD26 as a first host, Compound HTH1 as a second host, and Compound DF8 as a dopant were vacuum deposited on the electron blocking layer to form an emission layer having a thickness of 400 Å. In this regard, the amount of the dopant compound DF8 was 10 wt % with respect to the total weight of the host (100 wt %), and the weight ratio of Compound PD26 to Compound HTH1 was 3:7.

Compound T2T was vacuum-deposited on the emission layer to form a hole-blocking layer having a thickness of 50 Å, the compound $Alq_3$ was vacuum-deposited on the hole-blocking layer to form an electron transport layer having a thickness of 300 Å, the compound LiF was vacuum-deposited on the electron transport layer to form an electron injection layer having a thickness of 10 Å, and then, the element Al was vacuum-deposited thereon to form a cathode having a thickness of 3,000 Å, thereby completing the manufacture of an organic light-emitting device.

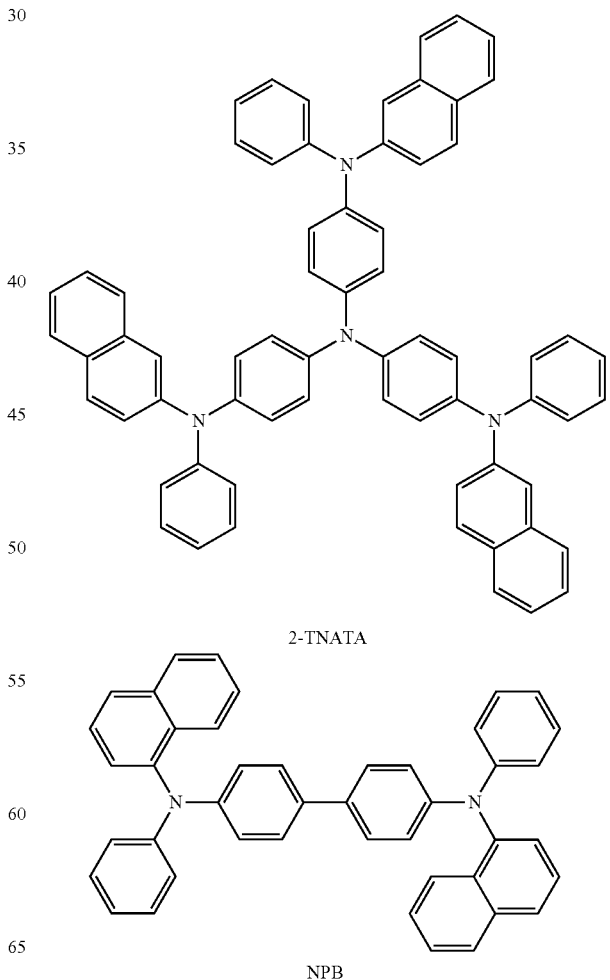

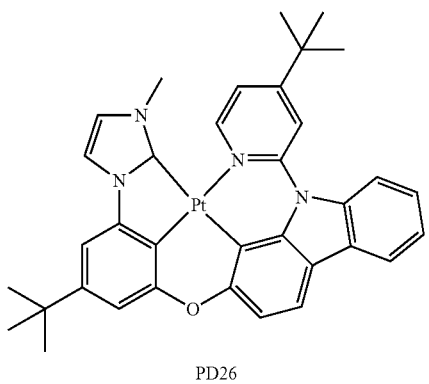

PD26

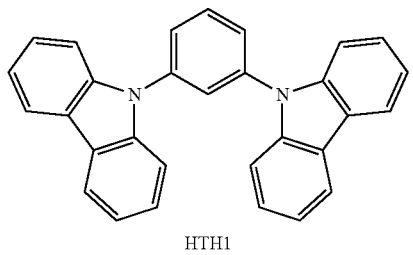

HTH1

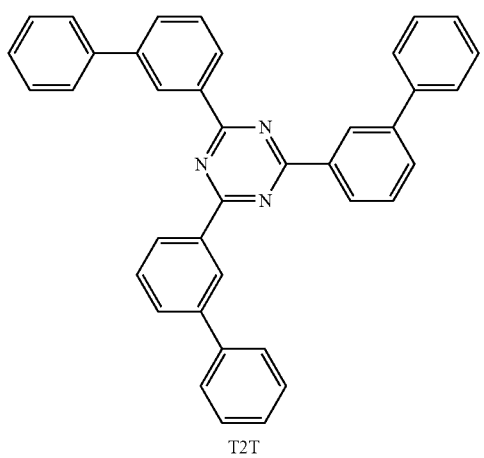

T2T

Comparative Example 1

An organic light-emitting device was manufactured in the same manner as in Example 1, except that, in forming an emission layer, Compound TCTA was used as a first host.

Comparative Example 2

An organic light-emitting device was manufactured in the same manner as in Example 1, except that, in forming an emission layer, (1,3,5-triazine-2,4,6-triyl)tris(benzene-3,1-diyl)tris(diphenylphosphine oxide) (Compound PO-T2T) was used as a second host.

Comparative Example 3

An organic light-emitting device was manufactured in the same manner as in Example 1, except that, in forming an emission layer, bis[2-(4,6-difluorophenyl)pyridinato-C2,N](picolinato)iridium (Compound Firpic) was used as a first host.

Compositions of the emission layers, electron-blocking layers, and hole-blocking layers of the organic light-emitting devices manufactured according to Example 1 and Comparative Examples 1 to 3 and the molecular orbital energy and $T_1$ values of corresponding compounds are shown in Table 1.

TABLE 1

| | First host (H1) | | Second host (H2) | | Dopant | Electron-blocking layer | | Hole-blocking layer | |
|---|---|---|---|---|---|---|---|---|---|
| | HOMO | LUMO | HOMO | LUMO | $T_1$ | HOMO | LUMO | HOMO | LUMO |
| Example 1 | PD26 | | HTH1 | | DF8 | m-MTDATA | | T2T | |
| | −5.2 | −2.0 | −6.4 | −2.4 | 2.7 | −5.2 | −2.0 | −6.5 | −3.0 |
| Comparative Example 1 | TCTA | | HTH1 | | DF8 | m-MTDATA | | T2T | |
| | −5.5 | −2.0 | −6.4 | −2.4 | 2.7 | −5.2 | −2.0 | −6.5 | −3.0 |
| Comparative Example 2 | PD26 | | PO-T2T | | DF8 | m-MTDATA | | T2T | |
| | −5.2 | −2.0 | −7.5 | −2.9 | 2.7 | −5.2 | −2.0 | −6.5 | −3.0 |
| Comparative Example 3 | Firpic | | HTH1 | | DF8 | m-MTDATA | | T2T | |
| | −5.8 | −3.1 | −6.4 | −2.4 | 2.7 | −5.2 | −2.0 | −6.5 | −3.0 |

The unit of numerical values in Table 1 is eV.

The characteristics of the organic light-emitting devices manufactured according to Example 1 and Comparative Examples 1 to 3 were evaluated by measuring the driving voltage (V) at the luminance of 1,000 cd/m$^2$, efficiency, and maximum emission wavelength (nm).

TABLE 2

| | Driving voltage (V) | EQE (%) | $T^{95}$ (hr) |
|---|---|---|---|
| Example 1 | 3.5 | 17 | 60 |
| Comparative Example 1 | 4.5 | 18 | 50 |
| Comparative Example 2 | 3.9 | 16 | 40 |
| Comparative Example 3 | 4.6 | 15 | 35 |

Table 2 shows that the organic light-emitting device manufactured according to Example 1 has a significantly and unexpectedly low driving voltage and improved lifespan compared to the organic light-emitting devices manufactured according to Comparative Examples 1 to 3.

Light-emitting devices constructed according to the principles and embodiments of the invention have a low driving voltage and excellent lifespan.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light-emitting device comprising:
a first electrode;
a second electrode facing the first electrode; and
an interlayer between the first electrode and the second electrode and comprising an emission layer,
wherein the emission layer comprises:
a first host, a second host, and a dopant,
at least one of the first host and the second host is an organometallic compound, and
the first host, the second host, and the dopant satisfy the following Equation (1):

|LUMO energy of $H2$–HOMO energy of $H1$|≥0.9× $T_1$ energy of $D$.

2. The light-emitting device of claim 1, wherein the first electrode comprises an anode,
the second electrode comprises a cathode, and
the light-emitting device further comprises a hole transport region between the first electrode and the emission layer and comprising an electron-blocking layer; and a hole injection layer, a hole transport layer, or any combination thereof.

3. The light-emitting device of claim 2, wherein the electron-blocking layer comprises an electron-blocking material, and
the first host and the electron-blocking material satisfy the following Equation (2):

|HOMO energy of electron-blocking material– HOMO energy of $H1$|≤0.2 eV.

4. The light-emitting device of claim 2, wherein the electron-blocking layer comprises an electron-blocking material, and
an absolute value of LUMO energy of the electron-blocking material is equal to or less than an absolute value of LUMO energy of the first host.

5. The light-emitting device of claim 1, wherein the first electrode comprises an anode,
the second electrode comprises a cathode, and
the light-emitting device further comprises an electron transport region between the second electrode and the emission layer and comprising a hole-blocking layer; and an electron transport layer, an electron injection layer, or any combination thereof.

6. The light-emitting device of claim 5, wherein the hole-blocking layer comprises a hole-blocking material, and
the second host and the hole-blocking material satisfy the following Equation (3):

|LUMO energy of hole-blocking material–LUMO energy of $H2$|≤0.2 eV.

7. The light-emitting device of claim 5, wherein the hole-blocking layer comprises a hole-blocking material, and
an absolute value of HOMO energy of the hole-blocking material is greater than an absolute value of HOMO energy of the second host.

8. The light-emitting device of claim 1, wherein the first host comprises a hole-transporting host.

9. The light-emitting device of claim 1, wherein the second host comprises an electron-transporting host.

10. The light-emitting device of claim 1, wherein an absolute value of LUMO energy of the first host is less than an absolute value of LUMO energy of the second host.

11. The light-emitting device of claim 1, wherein an absolute value of HOMO energy of the second host is greater than an absolute value of HOMO energy of the first host.

12. The light-emitting device of claim 1, wherein the first host and the second host have a weight ratio of about 1:9 to about 9:1.

13. The light-emitting device of claim 1, wherein the dopant is a fluorescent dopant.

14. The light-emitting device of claim 1, wherein the light-emitting device comprises a plurality of the first hosts and a plurality of the second hosts, at least one of the first hosts and at least one of the second hosts form excitons, and others of the first hosts or others of the second hosts that do not form excitons are capable of transferring energy of the excitons to the dopant.

15. The light-emitting device of claim 1, wherein the organometallic compound is a compound of Formula 401:

Formula 401

Formula 402

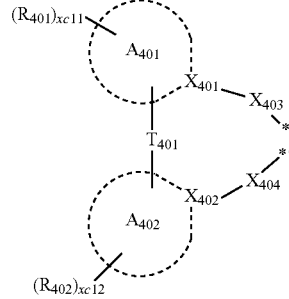

wherein, in Formulae 401 and 402,
M is a transition metal,
$L_{401}$ is a ligand of Formula 402, and xc1 is 1, 2, or 3, wherein when xc1 is 2 or 3, two or more of $L_{401}$(s) are identical to or different from each other,
$L_{402}$ is an organic ligand, and xc2 is 0, 1, 2, 3, or 4, wherein when xc2 is 2, 3, or 4, two or more of $L_{402}$(s) are identical to or different from each other,
$X_{401}$ and $X_{402}$ are each, independently from one another, nitrogen or carbon,
ring $A_{401}$ and ring $A_{402}$ are each, independently from one another, a $C_3$-$C_{60}$ carbocyclic group or a $C_1$-$C_{60}$ heterocyclic group,
$T_{401}$ is a single bond, *—O—*', *—S—*', *—C(=O)—*', *—N($Q_{411}$)—*', *—C($Q_{411}$)($Q_{412}$)-*', *—C($Q_{411}$)=C($Q_{412}$)-*', *—C($Q_{411}$)=*', or *=C=*',
$X_{403}$ and $X_{404}$ are each, independently from one another, a chemical bond, O, S, N($Q_{413}$), B($Q_{413}$), P($Q_{413}$), C($Q_{413}$)($Q_{414}$), or Si($Q_{413}$)($Q_{414}$),
$R_{401}$ and $R_{402}$ are each, independently from one another, hydrogen, deuterium, —F, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), xc11 and xc12 are each, independently from one another, an integer from 0 to 10, $Q_{411}$ to $Q_{414}$ and $Q_{401}$ to $Q_{403}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group, and

* and *' in Formula 402 are each a binding site to M in Formula 401.

16. The light-emitting device of claim 1, wherein each of the first host and the second host is not the organometallic compound, wherein the first host is a compound of Formula 1, and the second host is a compound of Formula 2:

Formula 1

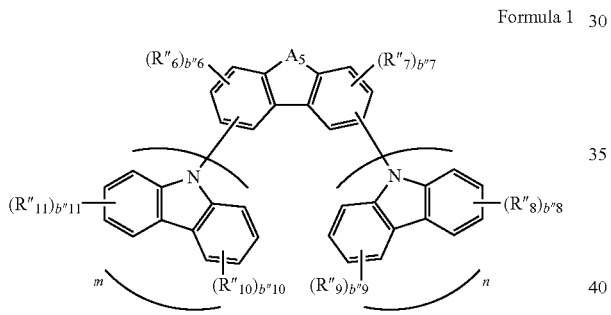

wherein, in Formula 1,
$A_5$ is O, S, NR"$_{12}$, or CR"$_{13}$R"$_{14}$,
m and n are each, independently from one another, 0 to 4,
R"$_6$ to R"$_{14}$ are each, independently from one another, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_8$-$C_{60}$ monovalent non-aromatic fused polycyclic group unsubstituted or substituted with at least one $R_{10a}$, a $C_1$-$C_{60}$ monovalent non-aromatic fused heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q$), —S(=O)$_2$($Q_1$), —P(=O)($Q_1$)($Q_2$), and —P(=S)($Q_1$)($Q_2$), b"6 to b"11 are each, independently from one another, an integer from 0 to 4, when b"6 is 2, 3, or 4, a plurality of R"$_6$(s) are identical to or different from each other, when b"7 is 2, 3, or 4, a plurality of R"$_7$(s) are identical to or different from each other, when b"8 is 2, 3, or 4, a plurality of R"$_8$(s) are identical to or different from each other, when b"9 is 2, 3, or 4, a plurality of R"$_9$(s) are identical to or different from each other, when b"10 is 2, 3, or 4, a plurality of R"$_{10}$(s) are identical to or different from each other, and when b"11 is 2, 3, or 4, a plurality of R"$_{11}$(s) are identical to or different from each other, two neighboring substituents among R"$_6$ to R"$_{14}$ are optionally linked to each other to form a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, Formula 2

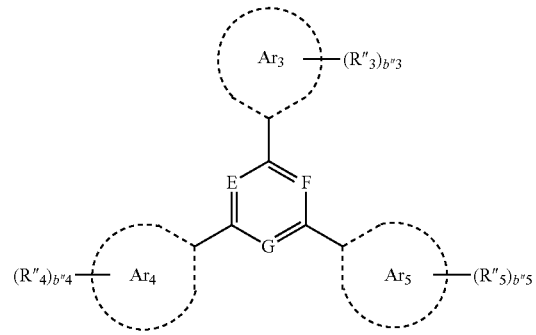

wherein, in Formula 2,
ring Ar$_3$ to ring Ar$_5$ are each, independently from one another, a $C_5$-$C_{60}$ carbocyclic group or a $C_1$-$C_{60}$ heterocyclic group,
E is N or CR"$_6$, F is N or CR"$_7$, and G is N or CR"$_8$,
R"$_3$ to R"$_8$ are each, independently from one another, hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_8$-$C_{60}$ monovalent non-aromatic fused polycyclic group unsubstituted or substituted with at least one $R_{10a}$, a $C_1$-$C_{60}$ monovalent non-aromatic fused heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), b"3 to b"5 are each, independently from one another, an integer from 1 to 5, when b"3 is 2, 3, 4, or 5, a plurality of R"$_3$(s) are identical to or different from each other, when b"4 is 2, 3, 4, or 5, a plurality of R"$_4$(s) are identical to or different from each other, and when b"5 is 2, 3, 4, or 5, a plurality of R"$_5$(s) are identical to or different from each other, two neighboring substituents among R"$_3$ to R"$_8$ are optionally linked to each other to form a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, and $Q_1$ to $Q_3$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

17. The light-emitting device of claim 1, wherein the dopant is one of the following compounds:

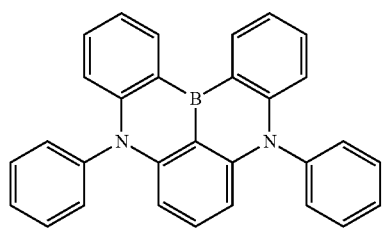

(DABNA-1)

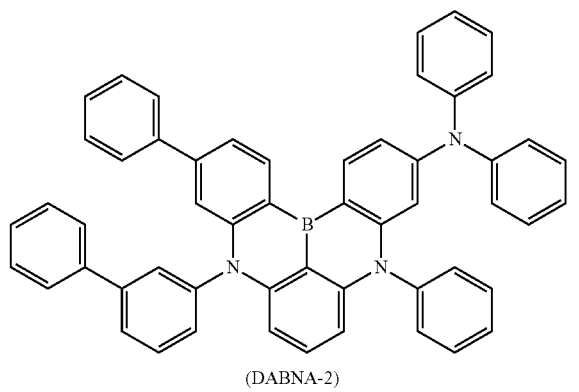

(DABNA-2)

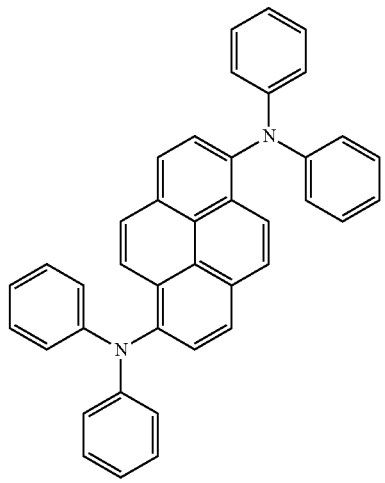

FD1

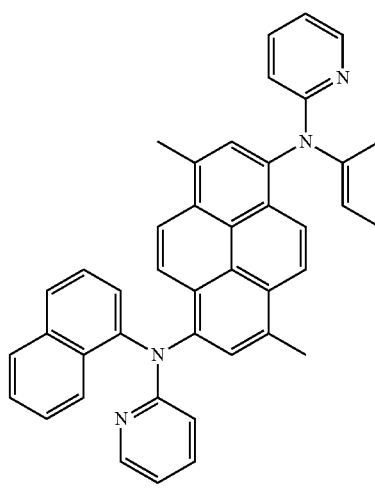

FD2

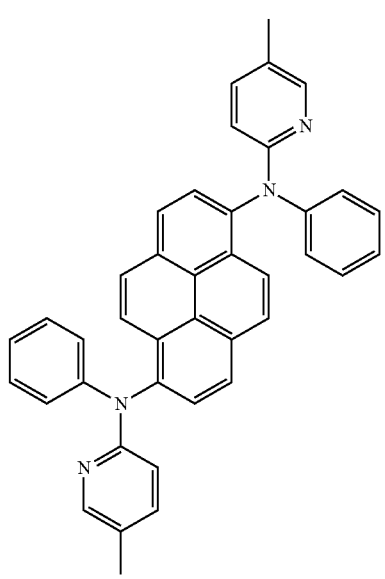

FD3

FD4

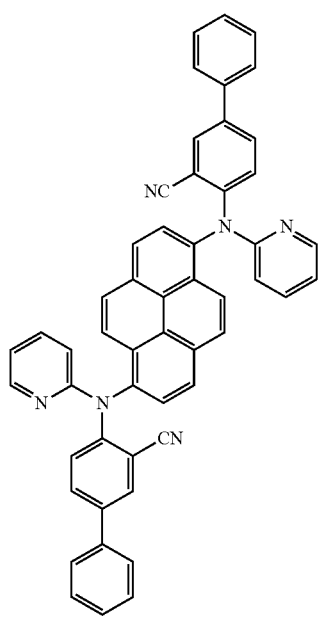

FD7

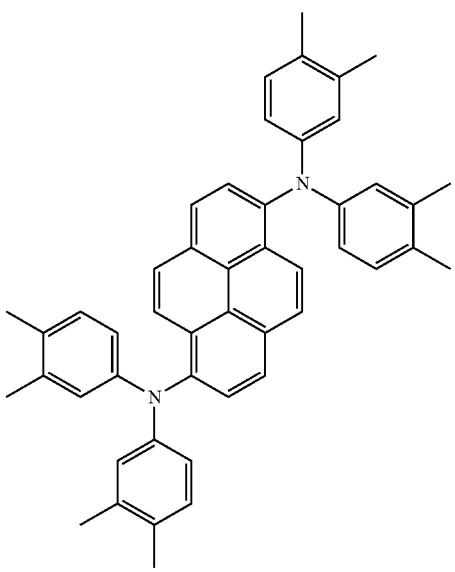

FD5

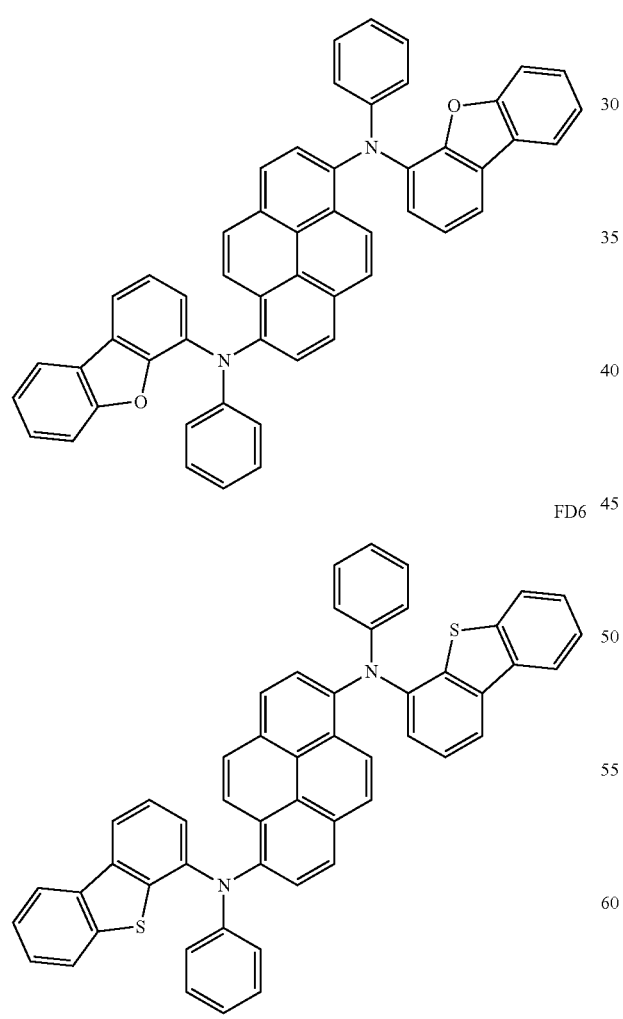

FD6

FD8

18. An electronic apparatus comprising the light-emitting device of claim 1.

19. The electronic apparatus of claim 18, further comprising a thin-film transistor,
wherein the thin-film transistor comprises a source electrode and a drain electrode, and
the first electrode of the light-emitting device is electrically connected to at least one of the source electrode and the drain electrode of the thin-film transistor.

20. The electronic apparatus of claim 18, further comprising a color filter, a color conversion layer, a touch screen layer, a polarizing layer, or any combination thereof.

* * * * *